US006949355B2

(12) United States Patent
Yamanishi et al.

(10) Patent No.: US 6,949,355 B2
(45) Date of Patent: Sep. 27, 2005

(54) METHODS, COMPOSITIONS, AND AUTOMATED SYSTEMS FOR SEPARATING RARE CELLS FROM FLUID SAMPLES

(75) Inventors: Douglas Yamanishi, San Diego, CA (US); Paul Hujsak, San Diego, CA (US); Zhaohuai Yang, San Diego, CA (US); Jùnquan Xu, San Diego, CA (US); Xiaobo Wang, San Diego, CA (US); Lei Wu, San Diego, CA (US); Mingxian Huang, San Diego, CA (US); Guoliang Tao, San Diego, CA (US); Jing Cheng, Beijing (CN)

(73) Assignee: AVIVA Biosciences, San Diego, CA (US)

(*) Notice: Subject to any disclaimer, the term of this patent is extended or adjusted under 35 U.S.C. 154(b) by 63 days.

(21) Appl. No.: 10/268,312

(22) Filed: Oct. 10, 2002

(65) Prior Publication Data

US 2003/0134416 A1 Jul. 17, 2003

Related U.S. Application Data

(60) Provisional application No. 60/394,517, filed on Jul. 9, 2002, provisional application No. 60/348,228, filed on Oct. 29, 2001, and provisional application No. 60/328,724, filed on Oct. 11, 2001.

(51) Int. Cl.$^7$ .................................................. C12Q 1/04
(52) U.S. Cl. ................... 435/34; 435/286.5; 435/288.5; 435/288.6; 435/288.7; 435/308.1
(58) Field of Search ................................ 435/34, 286.5, 435/288.5, 288.6, 288.7, 308.1

(56) References Cited

U.S. PATENT DOCUMENTS

| 5,437,987 A | 8/1995 | Teng et al. |
| 5,482,829 A | 1/1996 | Kass et al. |
| 5,626,734 A | 5/1997 | Decoslis et al. |
| 5,726,026 A | 3/1998 | Wilding et al. |
| 5,837,115 A | 11/1998 | Austin et al. |
| 5,883,760 A | 3/1999 | Yamada et al. |
| 5,928,880 A | 7/1999 | Wilding et al. |
| 6,355,491 B1 | 3/2002 | Zhou et al. |
| 2002/0022276 A1 | 2/2002 | Zhou et al. |
| 2002/0076825 A1 | 6/2002 | Cheng et al. |

FOREIGN PATENT DOCUMENTS

| WO | WO 02/12896 A1 | 2/2002 |
| WO | WO 02/28523 A2 | 4/2002 |
| WO | WO 02/30562 A1 | 4/2002 |
| WO | WO 02/31505 A1 | 4/2002 |
| WO | WO 02/31506 A1 | 4/2002 |

OTHER PUBLICATIONS

Gazdar et al., J. Natl. Cancer Inst., 91:299–301 (1999).
Decoslis et al., Biotechnology and Bioengineering, 54(3) 239–250 (1997).
Wang et al., Biophysical Journal, 74:2689–2701(1998).
Wang et al., IEEE Transactions on Industry Applications, 33(3):660–669 (1997).
Huang et al., J. Phys. D.: Appl. Phys., 26:1528–1535 (1993).
Wang et al., Biophys. J., 72:1887–1899 (1997).
Yasuda et al., J. Acoust. Soc. Am., 102(1):642–645 (1997).
Yasuda et al., J. Acoust. Soc. Am., 99(2):1248–1251 (1996).
Yasuda et al., J. Acous. Soc. Am., 99(4):1965–1970 (1996).
Yasuda and Kamakura, Appl. Phys. Lett., 71(13):1771–1773 (1997).
Pui et al., Biotachno. Prog., 11:146–152 (1995).

(Continued)

*Primary Examiner*—James Ketter
(74) *Attorney, Agent, or Firm*—David R. Preston & Associates; Elizabeth Orr

(57) ABSTRACT

The present invention recognizes that diagnosis and prognosis of many conditions can depend on the enrichment of rare cells from a complex fluid sample. In particular, the enrichment of fetal cells from maternal samples, such as maternal blood samples, can greatly aid in the detection of fetal abnormalities or a variety of genetic conditions. In addition, the present invention recognizes that the enrichment of rare malignant cells from patient samples, can aid in diagnosis, prognosis, and development of therapeutic modalities for patients.

A first aspect of the present invention is a microfabricated filter for filtering a fluid sample. A microfabricated filter of the present invention comprises at least one tapered pore, and preferably comprises at least two tapered pores whose variation in size is 20% or less. The present invention also includes a method of enriching rare cells of a fluid sample using a microfabricated filter of the present invention.

Another aspect of the invention is solutions for the selective sedimentation of red blood cells (RBCs) from a blood sample comprising a red blood cell aggregating agent and at least one specific binding member that selectively binds RBCs. Solutions of the present invention include a combined solution for rare cell enrichment that comprise RBC aggregating agents, at least one specific binding member that selectively binds RBCs, and at least one additional specific binding member for the removal of undesirable sample components other than RBCs. The invention also includes methods of using selective RBC sedimentation solutions and combined solutions for enriching rare cells of a fluid sample.

Yet another aspect of the invention is an automated system for processing a fluid sample that includes: at least one filtration chamber that comprises or engages one or more microfabricated filters of the present invention; automated means for directing fluid flow through the one or more filtration chambers of the automated system, and means for collecting enriched rare cells. The present invention also includes methods of using an automated system for separating rare cells from a fluid sample. Preferred fluid samples are effusion, blood, or urine samples, and rare cells that can be enriched from such sample include nucleated red blood cells and cancer cells.

39 Claims, 28 Drawing Sheets

OTHER PUBLICATIONS

Wu and Du, J. Acoust. Soc. Am., 87:997–1003 (1990).
Wu, J. Acoust. Soc. Am., 89:2140–2143 (1991).
Collins, Journal of Immunological Methods, 243:125–145 (2000).
Miller, Pediatric Cardiology, 20(4):287–289 (1999).
Ahn et al., J. Microelectromechanical Systems, 5:151–158 (1996).
Ahn et al., IEEE Trans. Magnetics, 30:73–79 (1994).
Safarik and Safarikova, J. of Chromotography 722(B):33–53 (1999).
Huang et al., Phys. Med. Biol., 37:1499–1517 (1992).
Yang et al., Biophys. J., 76:3307–3314 (1999).
Huang et al., Biochim. Biophys. Acta., 1417:51–56 (1999).
De Gasperis et al., Meas. Sci. Technol., 9:518–529 (1998).
Huang et al., Biochim. Biophys. Acta., 1282:76–84 (1996).
Becker et al., Proc. Natl. Acad. Sci. USA, 92:860–864 (1995).
Huang et al., J. Hematotheraphy and Stem Cell Research 8:481–490 (1999).
Liakopoulos et al., Transducers 97, pp. 484–488, presented in 1997 International Conference on Solid State Sensors and Actuators, Chicago, Jun. 16, 1997.

Fig. 2A
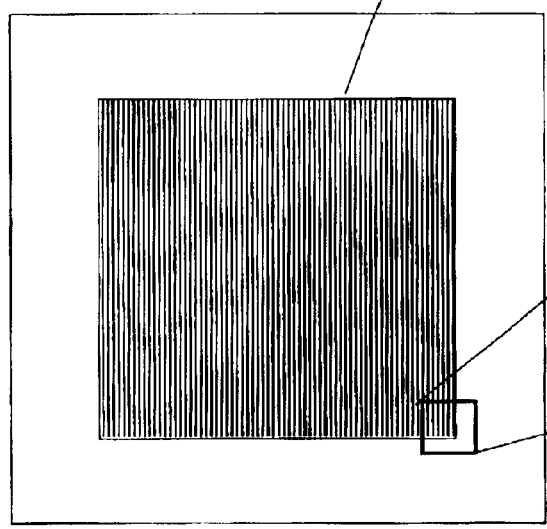
Fig. 2B
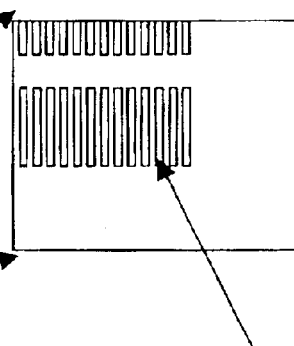
Fig. 2C 627    622

727    722

METHODS, COMPOSITIONS, AND AUTOMATED SYSTEMS FOR SEPARATING RARE CELLS FROM FLUID SAMPLES

CROSS-REFERENCE TO RELATED APPLICATIONS

This application claims benefit of priority to the following patent applications: U.S. Provisional Patent application No. 60/348,228, filed on Oct. 29, 2001, entitled "Methods and automated systems for separating rare cells from fluid samples", U.S. Provisional Patent application No. 60/328,724, filed Oct. 11, 2001, entitled "Methods and automated systems for separating rare cells from fluid samples", and U.S. Provisional Patent application No. 60/394,517, filed on Jul. 9, 2002, entitled "Methods and automated systems for separating rare cells from fluid samples", each of which is incorporated by reference herein in its entirety.

BACKGROUND OF THE INVENTION

The present invention relates generally to the field of bioseparation, and in particular to the field of biological sample processing.

Sample preparation is a necessary step for many genetic, biochemical, and biological analyses of biological and environmental samples. Sample preparation frequently requires the separation of sample components of interest from the remaining components of the sample. Such separations are often labor intensive and difficult to automate.

In many cases it is necessary to analyze relatively rare components of a sample. In this case, it may be necessary both to increase the concentration of the rare components to be analyzed, and to remove undesirable components of the sample that can interfere with the analysis of the components of interest. Thus, a sample must be "debulked" to reduce its volume, and in addition subjected to separation techniques that can enrich the components of interest. This is particularly true of biological samples, such as ascites fluid, lymph fluid, or blood, that can be harvested in large amounts, but that can contain minute percentages of target cells (such as virus-infected cells, anti-tumor T-cells, inflammatory cells, cancer cells, or fetal cells) whose separation is of critical importance for understanding the basis of disease states as well as for diagnosis and development of therapies.

Filtration has been used as a method of reducing the volume of samples and separating sample components based on their ability to flow through or be retained by the filter. Typically membrane filters are used in such applications in which the membrane filters have interconnected, fiber-like, structure distribution and the pores in the membrane are not discretely isolated; instead the pores are of irregular shapes and are connected to each other within the membrane. The so-called "pore" size really depends on the random tortuosity of the fluid-flow patches (e.g. pores) in the membrane. While the membrane filters can be used for a number of separation applications, the variation in the pore size and the irregular shapes of the pores prevent them being used for precise filtration based on particle size and other properties.

Microfabricated filters have been made for certain cellular or molecular separation. These microfabricated structures do not have pores, but rather include channels that are microetched into one or more chips, by using "bricks" (see, for example, U.S. Pat. No. 5,837,115 issued Nov. 17, 1998 to Austin et al., incorporated by reference) or dams see, for example, U.S. Pat. No. 5,726,026 issued Mar. 10, 1998 to Wilding et al., incorporated by reference) that are built onto the surface of a chip. While these microfabricated filters have precise geometries, their limitations are that the filtration area of the filter is small, limited by the geometries of these filters, so that these filters can process only small volumes of the fluid sample.

Blood samples provide special challenges for sample preparation and analysis. Blood samples are easily obtained from subjects, and can provide a wealth of metabolic, diagnostic, prognostic, and genetic information. However, the great abundance of non-nucleated red blood cells, and their major component hemoglobin, can be an impediment to genetic, metabolic, and diagnostic tests. The debulking of red blood cells from peripheral blood has been accomplished using different layers of dense solutions (for example, see U.S. Pat. No. 5,437,987 issued Aug. 1, 1995 to Teng, Nelson N. H. et al). Long chain polymers such as dextran have been used to induce the aggregation of red blood cells resulting in the formation of long red blood cell chains (Sewchand L S, Canham P B. Modes of rouleaux formation of human red blood cells in polyvinylpyrrolidone and dextran solutions 1979 57(11):1213–22). However, the efficiency of these solutions in removing red blood cells is less than optimal, especially where the separation or enrichment of rare cells, such as, for example, fetal cells from maternal blood or cancer cells from a patient, is desirable.

Exfoliated cells in body fluids (e.g. sputum, urine, or even ascetic fluid or other effusions) present a significant opportunity for detection of precancerous lesions and for eradication of cancer at early stages of neoplastic development. For example, urine cytology is universally accepted as the noninvasive test for the diagnosis and surveillance of transitional cell carcinoma (Larsson et al (2001) Molecular Diagnosis 6: 181–188). However, in many cases, the cytologic identification of abnormal exfoliated cells has been limited by the number of abnormal cells isolated. For routine urine cytology (Ahrendt et al. (1999) J. Natl. Cancer Inst. 91: 299–301), the overall sensitivity is less than 50%, which varies with tumor grade, tumor stage, and urine collection and processing methods used. Molecular analysis (e.g. using in situ hybridization, PCR, microarrays, etc) of abnormal exfoliated cells in body fluids based on molecular and genetic biomarkers can significantly improve the cytology sensitivity. Both biomarker studies and use of biomarkers for clinical practice would require a relative pure exfoliated cell population enriched from body fluids comprising not only exfoliated cells but also normal cells, bacteria, body fluids, body proteins and other cell debris. Thus, there is an immediate need for developing an effective enrichment method for enriching and isolating exfoliated abnormal cells from body fluids.

Current approaches for enriching and preparing exfoliated cells from body fluids are through media based separation, antibody capture, centrifugation and membrane filtration. While these techniques are simple and straightforward, they suffer from a number of limitations, including: inadequate efficiency for rare cell enrichment; low sensitivity of rare cell detection; difficulty in handling large volume samples; inconsistency of the enrichment performance; and labor-intensiveness of separation procedure.

There is a need to provide methods of sample preparation that are efficient and automatable that can process relatively large sample volumes, such as large volumes of biological fluid samples, and separate target cells. The present invention provides these and other benefits.

BRIEF SUMMARY OF THE INVENTION

The present invention recognizes that diagnosis, prognosis, and treatment of many conditions can depend on the enrichment of rare cells from a complex fluid sample. Often, enrichment can be accomplished by one or more separation steps. In particular, the separation of fetal cells from maternal blood samples, can greatly aid in the detection of fetal abnormalities or a variety of genetic conditions. In addition, the present invention recognizes that the enrichment or separation of rare malignant cells from patient samples, such as the isolation of cancerous cells from patient body fluid samples, can aid in the detection and typing of such malignant cells and therefore aid in diagnosis and prognosis, as well as in the development of therapeutic modalities for patients.

A first aspect of the present invention is a microfabricated filter for filtering a fluid sample. Filtration of a fluid sample can debulk a sample, can remove undesirable components from a fluid sample, or can separate desirable components from a fluid sample. A microfabricated filter of the present invention comprises at least one tapered pore, and preferably comprises at least two pores whose variation in size is 20% or less.

Another aspect of the present invention is a method for enriching rare cells from a fluid sample using filtration. The method includes: filtering a fluid sample through at least one microfabricated filter of the present invention, such that components of the sample flow through or are retained by the one or more microfabricated filters based on their size, shape, or deformability. The method can further include selectively removing undesirable components of said sample, or separating desirable components of said sample.

Another aspect of the present invention is solutions for enriching rare cells of a blood sample. In one aspect, a red blood cell sedimenting solution of the present invention comprises dextran and at least one specific binding member that can specifically bind red blood cells. In some preferred embodiments, a combined solution for enriching rare cells of a blood sample comprises dextran, at least one specific binding member that can selectively bind red blood cells, and at least one specific binding member that specifically binds undesirable components of a sample. In preferred embodiments, a combined solution includes a specific binding member that specifically binds white blood cells that is bound to or can bind magnetic beads. The present invention also includes methods of using solutions of the present invention for enriching rare cells of a blood sample.

Yet another aspect of the present invention is an automated system for enriching rare cells of a fluid sample. In some preferred embodiments, an automated system includes at least one filtration chamber, where a filtration chamber includes or engages one or more microfabricated filters having one or more tapered pores. An automated system of the present invention also includes automated means for producing fluid flow through the one or more filtration chambers, means for adding at least one solution or reagent to the fluid sample, and a vessel or outlet for collecting enriched rare cells. An automated system of the present invention includes at least one power supply or signal source or control circuit for the automated control and powering fluid flow through the one or more filtration chambers of the automated system and, optionally, at least one power supply or signal source for providing energy to generate physical forces used in at least one separation or mixing of sample components.

In some embodiments, the automated system includes at least one rack that can hold two or more tubes that contain sample, and solutions, reagents, and sample can be transferred into or out of the tubes using fluid uptake and dispensing systems that are connected to a power supply, signal source, or control circuit for automatic fluid transfer within the automated system. Automated systems that include a rack for holding sample tubes also preferably include one or more magnets that can be used in separating undesirable components of the sample and means for mechanical mixing of the tubes.

In some preferred embodiments, the automated system includes at least one separation chamber that can include one or more magnets that can be used in separating undesirable components of the sample, and a pump or negative pressure system for directing fluid flow through the one or more separation chambers. In these embodiments, automated systems for enriching rare cells can also include one or more active chips that can be used for mixing, capturing, or separating one or more sample components.

A further aspect of the present invention is a method of enriching rare cells from a fluid sample using an automated system of the present invention, comprising: introducing a fluid sample into the automated system of the present invention, filtering the fluid sample using at least one filtration chamber of the automated system, and collecting enriched rare cells from at least one outlet or at least one vessel of the automated system. Optionally, the method can also include removing undesirable components from the sample or separating desirable components from the sample in the automated system. A preferred sample is a blood, urine or effusion sample, and rare cells that can be enriched from such samples include nucleated red blood cells and cancer cells.

BRIEF DESCRIPTION OF THE FIGURES

FIG. 2 is a schematic representation of a microfabricated filter of the present invention. A) the top view, showing an 18×18 mm$^2$ microfabricated filter having a filtration area (1) of 10×10 mm$^2$. B) an enlargement of a section of the top view, showing the slots (2) having dimensions of 4 microns× 50 microns, with the center to center distance between slots of 12 microns, and their parallel alignment. C) a cross-sectional view of the microfabricated filter, with the slots extending through the filter substrate.

DETAILED DESCRIPTION OF THE INVENTION

Definitions

Figure 1:
FIG. 1 is the top view of a region of a microfabricated chip of the present invention. The dark areas are the precision manufactured slots in the filter that has a surface area of 1 cm$^2$.

Unless defined otherwise, all technical and scientific terms used herein have the same meaning as commonly understood by one of ordinary skill in the art to which this invention belongs. Generally, the nomenclature used herein and the manufacture procedures for devices and components described below are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

A "component" of a sample or "sample component" is any constituent of a sample, and can be an ion, molecule, compound, molecular complex, organelle, virus, cell, aggregate, or particle of any type, including colloids, aggregates, particulates, crystals, minerals, etc. A component of a sample can be soluble or insoluble in the sample media or a provided sample buffer or sample solution. A component of a sample can be in gaseous, liquid, or solid form. A component of a sample may be a moiety or may not be a moiety.

A "moiety" or "moiety of interest" is any entity whose manipulation is desirable. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules, small organic molecules, or complex organic molecules. A moiety can also be a molecular complex, can be an organelle, can be one or more cells, including prokaryotic and eukaryotic cells, or can be one or more etiological agents, including viruses, parasites, or prions, or portions thereof. A moiety can also be a crystal, mineral, colloid, fragment, mycelle, droplet, bubble, or the like, and can comprise one or more inorganic materials such as polymeric materials, metals, minerals, glass, ceramics, and the like. Moieties can also be aggregates of molecules, complexes, cells, organelles, viruses, etiological agents, crystals, colloids, or fragments. Cells can be any cells, including prokaryotic and eukaryotic cells. Eukaryotic cells can be of any type. Of particular interest are cells such as, but not limited to, white blood cells, malignant cells, stem cells, progenitor cells, fetal cells, and cells infected with an etiological agent, and bacterial cells. Moieties can also be artificial particles such polystyrene microbeads, microbeads of other polymer compositions, magnetic microbeads, and carbon microbeads.

As used herein, "manipulation" refers to moving or processing of the moieties, which results in one-, two- or three-dimensional movement of the moiety, whether within a single chamber or on a single chip, or between or among multiple chips and/or chambers. Moieties that are manipulated by the methods of the present invention can optionally be coupled to binding partners, such as microparticles. Non-limiting examples of the manipulations include transportation, capture, focusing, enrichment, concentration, aggregation, trapping, repulsion, levitation, separation, isolation or linear or other directed motion of the moieties. For effective manipulation of moieties coupled to binding partners, the binding partner and the physical force used in the method must be compatible. For example, binding partners with magnetic properties must be used with magnetic force. Similarly, binding partners with certain dielectric properties, e.g., plastic particles, polystyrene microbeads, must be used with dielectrophoretic force.

"Binding partner" refers to any substances that both bind to the moieties with desired affinity or specificity and are manipulatable with the desired physical force(s). Non-limiting examples of the binding partners include cells, cellular organelles, viruses, microparticles or an aggregate or complex thereof, or an aggregate or complex of molecules.

A "microparticle" or "particle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several thousand microns. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated or micromachined particles, etc.

"Coupled" means bound. For example, a moiety can be coupled to a microparticle by specific or nonspecific binding. As disclosed herein, the binding can be covalent or noncovalent, reversible or irreversible.

As used herein, "the moiety to be manipulated is substantially coupled onto surface of the binding partner" means that a percentage of the moiety to be manipulated is coupled onto surface of the binding partner and can be manipulated by a suitable physical force via manipulation of the binding partner. Ordinarily, at least 0.1% of the moiety to be manipulated is coupled onto surface of the binding partner. Preferably, at least 1%, 5%, 10%, 20%, 30%, 40%, 50%, 60%, 70%, 80% or 90% of the moiety to be manipulated is coupled onto surface of the binding partner.

As used herein, "the moiety to be manipulated is completely coupled onto surface of the binding partner" means that at least 90% of the moiety to be manipulated is coupled onto surface of the binding partner. Preferably, at least 91%, 92%, 93%, 94%, 95%, 96%, 97%, 98%, 99% or 100% of the moiety to be manipulated is coupled onto surface of the binding partner.

A "specific binding member" is one of two different molecules having an area on the surface or in a cavity which specifically binds to and is thereby defined as complementary with a particular spatial and chemical organization of the other molecule. A specific binding member can be a member of an immunological pair such as antigen-antibody or antibody-antibody, can be biotin-avidin, biotin-streptavidin, or biotin-neutravidin, ligand-receptor, nucleic acid duplexes, IgG-protein A, DNA-DNA, DNA-RNA, RNA-RNA, and the like.

An "antibody" is an immunoglobulin molecule, and can be, as nonlimiting example, an IgG, an IgM, or other type of immunoglobulin molecule. As used herein, "antibody" also refers to a portion of an antibody molecule that retains the binding specificity of the antibody from which it is derived (for example, single chain antibodies or Fab fragments).

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

"Homogeneous manipulation" refers to the manipulation of particles in a mixture using physical forces, wherein all particles of the mixture have the same response to the applied force.

"Selective manipulation" refers to the manipulation of particles using physical forces, in which different particles in a mixture have different responses to the applied force.

A "fluid sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample, or a wash of an internal area of the body.

A "blood sample" as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. Another example of a blood sample is a blood sample that has been "washed" to remove serum components by centrifuging the sample to pellet cells, removing the serum supernatant, and resuspending the cells in a solution or buffer. Other blood samples include cord blood samples, bone marrow aspirates, internal blood or peripheral blood. A blood sample can be of any volume, and can be from any subject such as an animal or human. A preferred subject is a human.

A "rare cell" is a cell that is either 1) of a cell type that is less than 1% of the total nucleated cell population in a fluid sample, or 2) of a cell type that is present at less than one million cells per milliliter of fluid sample. A "rare cell of interest" is a cell whose enrichment is desirable.

A "white blood cell" is a leukocyte, or a cell of the hematopoietic lineage that is not a reticulocyte or platelet and that can be found in the blood of an animal or human. Leukocytes can include nature killer cells ("NK cells") and lymphocytes, such as B lymphocytes ("B cells") or T lymphocytes ("T cells"). Leukocytes can also include phagocytic cells, such as monocytes, macrophages, and granulocytes, including basophils, eosinophils and neutrophils. Leukocytes can also comprise mast cells.

A "red blood cell" or "RBC" is an erythrocyte. Unless designated a "nucleated red blood cell" ("nRBC") or "fetal nucleated red blood cell", as used herein, "red blood cell" is used to mean a non-nucleated red blood cell.

"Neoplastic cells" refers to abnormal cells that have uncontrolled cellular proliferation and can continue to grow after the stimuli that induced the new growth has been withdrawn. Neoplastic cells tend to show partial or complete lack of structural organization and functional coordination with the normal tissue, and may be benign or malignant.

A "malignant cell" is a cell having the property of locally invasive and destructive growth and metastasis. Examples of "malignant cells" include, but not limited to, leukemia cells, lymphoma cells, cancer cells of solid tumors, metastatic solid tumor cells (e.g., breast cancer cells, prostate cancer cells, lung cancer cells, colon cancer cells) in various body fluids including blood, bone marrow, ascistic fluids, stool, urine, bronchial washes etc.

A "cancerous cell" is a cell that exhibits deregulated growth and, in most cases, has lost at least one of its differentiated properties, such as, but not limited to, characteristic morphology, non-migratory behavior, cell-cell interaction and cell-signaling behavior, protein expression and secretion pattern, etc.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, fungus, protozoan, virus, parasite or prion that can infect a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that is capable of containing a fluid sample, in which at least one processing step can be performed. The chamber may have various dimensions and its volume may vary between ten microliters and 0.5 liter.

A "filtration chamber" is a chamber through which or in which a fluid sample can be filtered.

A "filter" is a structure that comprises one or more pores or slots of particular dimensions (that can be within a particular range), that allows the passage of some sample components but not others from one side of the filter to the other, based on the size, shape, and/or deformability of the particles. A filter can be made of any suitable material that prevents passage of insoluble particles, such as metal, ceramics, glass, silicon, plastics, polymers, fibers (such as paper or fabric), etc.

A "filtration unit" is a filtration chamber and the associated inlets, valves, and conduits that allow sample and solutions to be introduced into the filtration chamber and sample components to be removed from the filtration chamber. A filtration unit optionally also comprises a loading reservoir.

A "cartridge" is a structure that comprises at least one chamber that is part of a manual or automated system and one or more conduits for the transport of fluid into or out of at least one chamber. A cartridge may or may not comprise one or more chips.

An "automated system for separating rare cells from a fluid sample" or an "automated system" is a device that comprises at least one filtration chamber, automated means for directing fluid flow through the filtration chamber, and at least one power source for providing fluid flow and, optionally, providing a signal source for the generation of forces on active chips. An automated system of the present invention can also optionally include one or more active chips, separation chambers, separation columns, or permanent magnets.

A "port" is an opening in the housing of a chamber through which a fluid sample can enter or exit the chamber. A port can be of any dimensions, but preferably is of a shape and size that allows a sample to be dispensed into a chamber by pumping a fluid through a conduit, or by means of a pipette, syringe, or other means of dispensing or transporting a sample.

An "inlet" is a point of entrance for sample, solutions, buffers, or reagents into a fluidic chamber. An inlet can be a port of a chamber, or can be an opening in a conduit that leads, directly or indirectly, to a chamber of an automated system.

An "outlet" is the opening at which sample, sample components, or reagents exit a fluidic chamber. The sample components and reagents that leave a chamber can be waste, i.e., sample components that are not to be used further, or can be sample components or reagents to be recovered, such as, for example, reusable reagents or target cells to be further analyzed or manipulated. An outlet can be a port of a chamber, but preferably is an opening in a conduit that, directly or indirectly, leads from a chamber of an automated system.

A "conduit" is a means for fluid to be transported from a container to a chamber of the present invention. Preferably a conduit directly or indirectly engages a port in the housing of a chamber. A conduit can comprise any material that permits the passage of a fluid through it. Conduits can comprise tubing, such as, for example, rubber, Teflon, or tygon tubing. Conduits can also be molded out of a polymer or plastic, or drilled, etched, or machined into a metal, glass or ceramic substrate. Conduits can thus be integral to structures such as, for example, a cartridge of the present invention. A conduit can be of any dimensions, but preferably ranges from 10 microns to 5 millimeters in internal diameter. A conduit is preferably enclosed (other than fluid entry and exit points), or can be open at its upper surface, as a canal-type conduit.

A "chip" is a solid substrate on which one or more processes such as physical, chemical, biochemical, biological or biophysical processes can be carried out, or a solid substrate that comprises or supports one or more applied force-generating elements for carrying out one or more physical, chemical, biochemical, biological, or biophysical processes. Such processes can be assays, including biochemical, cellular, and chemical assays; separations, including separations mediated by electrical, magnetic, physical, and chemical (including biochemical) forces or interactions; chemical reactions, enzymatic reactions, and binding interactions, including captures. The micro structures or micro-scale structures such as, channels and wells, bricks, dams, filters, electrode elements, electromagnetic elements, or acoustic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces. A chip can have one or more openings, such as pores or slots.

An "active chip" is a chip that comprises micro-scale structures that are built into or onto a chip that when energized by an external power source can generate at least one physical force that can perform a processing step or task or an analysis step or task, such as, but not limited to, mixing, translocation, focusing, separation, concentration, capture, isolation, or enrichment. An active chip uses applied physical forces to promote, enhance, or facilitate desired biochemical reactions or processing steps or tasks or analysis steps or tasks. On an active chip, "applied physical forces" are physical forces that, when energy is provided by a power source that is external to an active chip, are generated by micro-scale structures built into or onto a chip.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, dams, bricks, filters, scaffolds, electrodes, electromagnetic units, acoustic elements, or microfabricated pumps or valves. A variety of micro-scale structures are disclosed in U.S. patent application Ser. No. 09/679,024, entitled "Apparatuses Containing Multiple Active Force Generating Elements and Uses Thereof" filed Oct. 4, 2000, herein incorporated by reference in its entirety. Micro-scale structures that can, when energy, such as an electrical signal, is applied, generate physical forces useful in the present invention, can be referred to as "physical force-generating elements" "physical force elements", "active force elements", or "active elements".

A variety of micro-scale structures are disclosed in U.S. patent application Ser. No. 09/679,024, entitled "Apparatuses Containing Multiple Active Force Generating Elements and Uses Thereof" filed Oct. 4, 2000, herein incorporated by reference in its entirety. Micro-scale structures that can, when energy, such as an electrical signal, is applied, generate physical forces useful in the present invention, can be referred to as "physical force-generating elements" "physical force elements", "active force elements", or "active elements".

A "multiple force chip" or "multiforce chip" is a chip that generates physical force fields and that has at least two different types of built-in structures each of which is, in combination with an external power source, capable of generating one type of physical field. A full description of the multiple force chip is provided in U.S. application Ser. No. 09/679,024, entitled "Apparatuses Containing Multiple Active Force Generating Elements and Uses Thereof" filed Oct. 4, 2000, herein incorporated by reference in its entirety.

"Acoustic forces" are the forces exerted, directly or indirectly on moieties (e.g., particles and/or molecules) by an acoustic wave field. Acoustic forces can be used for manipulating (e.g., trapping, moving, directing, handling) particles in fluid. Acoustic waves, both standing acoustic wave and traveling acoustic wave, can exert forces directly on moieties and such forces are called "acoustic radiation forces". Acoustic wave may also exert forces on the fluid medium in which the moieties are placed, or suspended, or dissolved and result in so-called acoustic streaming. The acoustic streaming, in turn, will exert forces on the moieties placed, suspended or dissolved in such a fluid medium. In this case, the acoustic wave fields can exert forces on moieties in directly.

"Acoustic elements" are structures that can generate an acoustic wave field in response to a power signal. Preferred acoustic elements are piezoelectric transducers that can generate vibrational (mechanical) energy in response to applied AC voltages. The vibrational energy can be transferred to a fluid that is in proximity to the transducers, causing an acoustic force to be exerted on particles (such as, for example, cells) in the fluid. A description of acoustic forces and acoustic elements can be found in U.S. patent application Ser. No. 09/636,104, filed Aug. 10, 2000, incorporated by reference in its entirety.

"Piezoelectic transducers" are structures capable of generating an acoustic field in response to an electrical signal. Non-limiting examples of the piezoelectric transducers are ceramic disks (e.g. PZT, Lead Zirconium Titinate) covered on both surfaces with metal film electrodes, piezoelectric thin films (e.g. zinc-oxide).

"Mixing" as used herein means the use of physical forces to cause particle movement in a sample, solution, or mixture, such that components of the sample, solution, or mixture become interspersed. Preferred methods of mixing for use in the present invention include use of acoustic forces.

"Processing" refers to the preparation of a sample for analysis, and can comprise one or multiple steps or tasks.

Generally a processing task serves to separate components of a sample, concentrate components of a sample, at least partially purify components of a sample, or structurally alter components of a sample (for example, by lysis or denaturation).

As used herein, "isolating" means separating a desirable sample component from other nondesirable components of a sample, such that preferably, at least 15%, more preferably at least 30%, even more preferably at least 50%, and further preferably, at least 80% of the desirable sample components present in the original sample are retained, and preferably at least 50%, more preferably at least 80%, even more preferably, at least 95%, and yet more preferably, at least 99%, of at least one nondesirable component of the original component is removed, from the final preparation.

"Rare cells" are cells whose abundance in the original sample is either 1) less than 1% of the total nucleated cell population in a fluid sample, or 2) present at less than one million cells per milliliter of fluid sample.

"Enrich" means increase the concentration of a sample component of a sample relative to other sample components (which can be the result of reducing the concentration of other sample components), or increase the concentration of a sample component. For example, as used herein, "enriching" fetal red blood cells from a blood sample means increasing the proportion of fetal red blood cells to all cells in the blood sample, enriching cancer cells of a blood sample can mean increasing the concentration of cancer cells in the sample (for example, by reducing the sample volume) or reducing the concentration of other cellular components of the blood sample, and "enriching" cancer cells in a urine sample can mean increasing their concentration in the sample.

"Separation" is a process in which one or more components of a sample are spatially separated from one or more other components of a sample. A separation can be performed such that one or more sample components of interest is translocated to or retained in one or more areas of a separation apparatus and at least some of the remaining components are translocated away from the area or areas where the one or more sample components of interest are translocated to and/or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. It is also possible to cause one or more sample components to be translocated to one or more areas and one or more sample components of interest or one or more components of a sample to be translocated to one or more other areas. Separations can be achieved through, for example, filtration, or the use of physical, chemical, electrical, or magnetic forces. Nonlimiting examples of forces that can be used in separations are gravity, mass flow, dielectrophoretic forces, traveling-wave dielectrophoretic forces, and electromagnetic forces.

"Separating a sample component from a (fluid) sample" means separating a sample component from other components of the original sample, or from components of the sample that are remaining after one or more processing steps. "Removing a sample component from a (fluid) sample" means removing a sample component from other components of the original sample, or from components of the sample that are remaining after one or more processing steps.

"Capture" is a type of separation in which one or more moieties or sample components is retained in or on one or more areas of a surface, chamber, chip, tube, or any vessel that contains a sample, where the remainder of the sample can be removed from that area.

An "assay" is a test performed on a sample or a component of a sample. An assay can test for the presence of a component, the amount or concentration of a component, the composition of a component, the activity of a component, etc. Assays that can be performed in conjunction with the compositions and methods of the present invention include, but not limited to, immunocytochemical assays, interphase FISH (fluorescence in situ hybridization), karyotyping, immunological assays, biochemical assays, binding assays, cellular assays, genetic assays, gene expression assays and protein expression assays.

A "binding assay" is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the presence, concentration, or activity of one or more components of a sample.

A "cellular assay" is an assay that tests for a cellular process, such as, but not limited to, a metabolic activity, a catabolic activity, an ion channel activity, an intracellular signaling activity, a receptor-linked signaling activity, a transcriptional activity, a translational activity, or a secretory activity.

A "genetic assay" is an assay that tests for the presence or sequence of a genetic element, where a genetic element can be any segment of a DNA or RNA molecule, including, but not limited to, a gene, a repetitive element, a transposable element, a regulatory element, a telomere, a centromere, or DNA or RNA of unknown function. As nonlimiting examples, genetic assays can be gene expression assays, PCR assays, karyotyping, or FISH. Genetic assays can use nucleic acid hybridization techniques, can comprise nucleic acid sequencing reactions, or can use one or more enzymes such as polymerases, as, for example a genetic assay based on PCR. A genetic assay can use one or more detectable labels, such as, but not limited to, fluorochromes, radioisotopes, or signal generating systems.

"FISH" or "fluorescence in situ hybridization" is an assay wherein a genetic marker can be localized to a chromosome by hybridization. Typically, to perform FISH, a nucleic acid probe that is fluorescently labeled is hybridized to interphase chromosomes that are prepared on a slide. The presence and location of a hybridizing probe can be visualized by fluorescence microscopy. The probe can also include an enzyme and be used in conjunction with a fluorescent enzyme substrate.

"Karyotyping" refers to the analysis of chromosomes that includes the presence and number of chromosomes of each type (for example, each of the 24 chromosomes of the human haplotype (chromosomes 1–22, X, and Y)), and the presence of morphological abnormalities in the chromosomes, such as, for example, translocations or deletions. Karyotyping typically involves performing a chromosome spread of a cell in metaphase. The chromosomes can then be visualized using, foe example, but not limited to, stains or genetic probes to distinguish the specific chromosomes.

A "gene expression assay (or "gene expression profiling assay") is an assay that tests for the presence or quantity of one or more gene expression products, i.e. messenger RNAs. the one or more types of mRNAs can be assayed simultaneously on cells of the interest from a sample. For different applications, the number and/or the types of mRNA molecules to be assayed in the gene expression assays may be different.

A "protein expression assay" (or "protein expression profiling assay") is an assay that tests for the presence or quantity of one or more proteins. One or more types of protein can be assayed simultaneously on the cells of the interest from a sample. For different applications, the number and/or the types of protein molecules to be assayed in the protein expression assays may be different.

"Histological examination" refers to the examination of cells using histochemical or stains or specific binding members (generally coupled to detectable labels) that can determine the type of cell, the expression of particular markers by the cell, or can reveal structural features of the cell (such as the nucleus, cytoskeleton, etc.) or the state or function of a cell. In general, cells can be prepared on slides and "stained" using dyes or specific binding members directly or indirectly bound to detectable labels, for histological examination. Examples of dyes that can be used in histological examination are nuclear stains, such as Hoescht stains, or cell viability stains, such as Trypan blue, or cellular structure stains such as Wright or Giemsa, enzyme activity benzidine for HRP to form visible precipitate. Examples of specific binding members that can be used in histological examination of fetal red blood cells are antibodies that specifically recognize fetal or embryonic hemoglobin.

An "electrode" is a structure of highly electrically conductive material. A highly conductive material is a material with a conductivity greater than that of surrounding structures or materials. Suitable highly electrically conductive materials include metals, such as gold, chromium, platinum, aluminum, and the like, and can also include nonmetals, such as carbon and conductive polymers. An electrode can be any shape, such as rectangular, circular, castellated, etc. Electrodes can also comprise doped semi-conductors, where a semi-conducting material is mixed with small amounts of other "impurity" materials. For example, phosphorous-doped silicon may be used as conductive materials for forming electrodes.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip.

A "channel" is a structure in a chip with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

A "pore" is an opening in a surface, such as a filter of the present invention, that provides fluid communication between one side of the surface and the other. A pore can be of any size and of any shape, but preferably a pore is of a size and shape that restricts passage of at least one insoluble sample component from one side of a filter to the other side of a filter based on the size, shape, and deformability (or lack thereof), of the sample component.

A "slot" is an opening in a surface, such as a filter of the present invention. The slot length is longer than its width (slot length and slot width refer to the slots dimensions in the plane or the surface of the filter into which the sample components will go through, and slot depth refers to the thickness of the filter). The term "slot" therefore describes the shape of a pore, which will in most cases be approximately rectangular, ellipsoid, or that of a quadrilateral or parallelogram.

"Bricks" are structures that can be built into or onto a surface that can restrict the passage of sample components between bricks. The design and use of one type of bricks (called "obstacles") on a chip is described in U.S. Pat. No. 5,837,115 issued Nov. 17, 1998 to Austin et al., herein incorporated by reference in its entirety A "dam" is a structure built onto the lower surface of a chamber that extends upward toward the upper surface of a chamber leaving a space of defined width between the top of the dam and the top of the chamber. Preferably, the width of the space between the top of the dam and the upper wall of the chamber is such that fluid sample can pass through the space, but at least one sample component is unable to pass through the space based on its size, shape, or deformability (or lack thereof). The design and use of one type of dam structure on a chip is described in U.S. Pat. No. 5,928,880 issued Jul. 27, 1999 to Wilding et al., herein incorporated by reference in its entirety.

"Continuous flow" means that fluid is pumped or injected into a chamber of the present invention continuously during the separation process. This allows for components of a sample that are not selectively retained in a chamber to be flushed out of the chamber during the separation process.

"Binding partner" refers to any substances that both bind to the moieties with desired affinity or specificity and are manipulatable with the desired physical force(s). Non-limiting examples of the binding partners include microparticles.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, sepharose, agarose, cellulose, cellulose derivatives, or dextran, and/or can comprise metals. Examples of microparticles include, but are not limited to, magnetic beads, magnetic particles, plastic particles, ceramic particles, carbon particles, polystyrene microbeads, glass beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159–185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

Other technical terms used herein have their ordinary meaning in the art that they are used, as exemplified by a variety of technical dictionaries.

Introduction

The present invention recognizes that analysis of complex fluids, such as biological fluid samples, can be confounded by many sample components that can interfere with the analysis. Sample analysis can be even more problematic when the target of the analysis is a rare cell type, for example, when the target cells are fetal cells present in maternal blood or malignant cells present in the blood or urine of a patient. In processing such samples, it is often necessary to both "debulk" the sample, by reducing the volume to a manageable level, and to enrich the population of rare cells that are the target of analysis. Procedures for the processing of fluid samples are often time consuming and inefficient. The present invention provides efficient methods and automated systems for the enrichment of rare cells from fluid samples.

As a non-limiting introduction to the breath of the present invention, the present invention includes several general and useful aspects, including:

1) a microfabricated filter for filtering a fluid sample. A microfabricated filter of the present invention comprises at least one tapered pore, and preferably comprises at least two tapered pores whose variation in size is 20% or less.

2) a method of enriching rare cells of a fluid sample using a microfabricated filter of the present invention.

3) solutions for the selective sedimentation of red blood cells (RBCs) from a blood sample comprising a red blood cell aggregating agent and at least one specific binding member that selectively binds RBCs. Solutions of the present invention include a combined solution for rare cell enrichment that comprise dextran, at least one specific binding member that selectively binds RBCs, and at least one additional specific binding member for the removal of undesirable sample components other than RBCs.

4) methods of using selective RBC sedimentation solutions and combined solutions for enriching rare cells of a fluid sample.

5) an automated system for processing a fluid sample that includes: at least one filtration chamber that comprises or engages one or more microfabricated filters of the present invention; automated means for directing fluid flow through the one or more filtration chambers of the automated system, and means for collecting enriched rare cells.

6) a method of using an automated system for separating rare cells from a fluid sample thal includes: introducing a fluid sample into an automated system of the present invention, filtering the fluid sample using at least one filtration chamber of the automated system; and collecting enriched rare cells from at least one outlet or at least one vessel of the automated system. Preferably, the method also includes removing undesirable components of the fluid sample or separating rare cells of the sample in at least one vessel, chamber, or column of the present invention. A preferred fluid sample is an effusion, blood, or urine sample, and rare cells that can be enriched from such sample include nucleated red blood cells and cancer cells.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Microfabricated Filter

The present invention includes a microfabricated filter that comprises at least one tapered pore, where a pore is an opening in the filter. A pore can be of any shape and any dimensions. For example, a pore can be quadrilateral, rectangular, ellipsoid, or circular in shape, or of other geometric or non-geometric shape. A pore can have a diameter (or widest dimension) of from about 0.1 micron to about 1000 microns, preferably from about 20 to about 200 microns, depending on the filtering application. Preferably, a pore is made during the machining of a filter, and is microetched or bored into the filter material that comprises a hard, fluid-impermeable material such as glass, silicon, ceramics, metal or hard plastic such as acrylic, polycarbonate, or polyimide. It is also possible to use a relatively nonhard surface for the filter that is supported on a hard solid support. Preferably, however, the filter comprises a hard material that is not deformable by the pressure (such as suction pressure) used in generating fluid flow through the filter.

A slot is a pore with a length that is greater than its width, where "length" and "width" are dimensions of the opening in the plane of the filter. (The "depth" of the slot corresponds to the thickness of the filter.) That is, "slot" describes the shape of the opening, which will in most cases be approximately rectangular or ellipsoid, but can also approximate a quadrilateral or parallelogram. In preferred embodiments of the present invention in which slot width is the critical dimension in detennining which sample components flow through or are retained by the filter, the shape of the slot can vary at the ends (for example, be regular or irregular in shape, curved or angular), but preferably the long sides of the slot are a consistent distance from one another for most of the length of the slot, that distance being the slot width. Thus the long sides of a slot will be parallel or very nearly parallel, for most of the length of the slot.

Preferably, the filters used for filtration in the present invention are microfabricated or micromachined filters so that the pores or the slots within a filter can achieve precise and uniform dimensions. Such precise and uniform pore or slot dimensions are a distinct advantage of the microfabricated or micromachined filters of the present invention, in comparison with the conventional membrane filters made of materials such as nylon, polycarbonate, polyester, mixed cellulose ester, polytetrafluoroethylene, polyethersulfone, etc. In the filters of the present invention, individual pores are isolated, have similar or almost identical feature sizes, and are patterned on a filter. Such filters allow precise separation of particles based on their sizes and other properties.

The filtration area of a filter is determined by the area of the substrate comprising the pores. The filtration area for microfabricated filters of the present invention can be between about 0.01 mm$^2$ and about 0.1 m$^2$. Preferably, the filtration area is between about 0.25 mm$^2$ and about 25 cm$^2$, and more preferably is between about 0.5 mm² and about 10 cm². The large filtration areas allow the filters of the invention to process sample volumes from about 100 microliters to about 10 liters. The percent of the filtration area encompassed by pores can be from about 1% to about 70%, preferably is from about 10% to about 50%, and more preferably is from about 15 to about 40%. The filtration area of a microfabricated filter of the present invention can comprise any number of pores, and preferably comprises at least two pores, but more preferably the number of pores in the filtration area of a filter of the present invention ranges from about 4 to about 1,000,000, and even more preferably ranges from about 100 to about 250,000. The thickness of the filter in the filtration area can range from about 10 to about 500 microns, but is preferably in the range of between about 40 and about 100 microns.

The microfabricated filters of the present invention have slots or pores that are etched through the filter substrate itself. The pores or openings of the filters can be made by using microfabrication or micromachining techniques on substrate materials, including, but not limited to, silicon, silicon dioxide, ceramics, glass, polymers such as polyimide, polyamide, etc. Various fabrication methods, as known to those skilled in the art of microlithography and microfabrication (See, for example, Rai-Choudhury P. (Editor), Handbook of Microlithography, Micromachining and Microfabrication, Volume 2: Micromachining and microfabrication. SPIE Optical Engineering Press, Bellingham, Wash., USA (1997)), may be used. In many cases, standard microfabrication and micromachining methods and protocols may be involved. One example of suitable fabrication methods is photolithography involving single or multiple photomasks. The protocols in the microfabrication may include many basic steps, for example, photolithographic mask generation, deposition of photoresist, deposition of "sacrificial" material layers, photoresist patterning with masks and developers, or "sacrificial" material layer patterning. Pores can be made by etching into the substrate under certain masking process so that the regions that have been masked are not etched off and the regions that have not been mask-protected are etched off. The etching method can be dry-etching such as deep RIE (reactive ion etching), laser ablation, or can be wet etching involving the use of wet chemicals.

Figure 4:
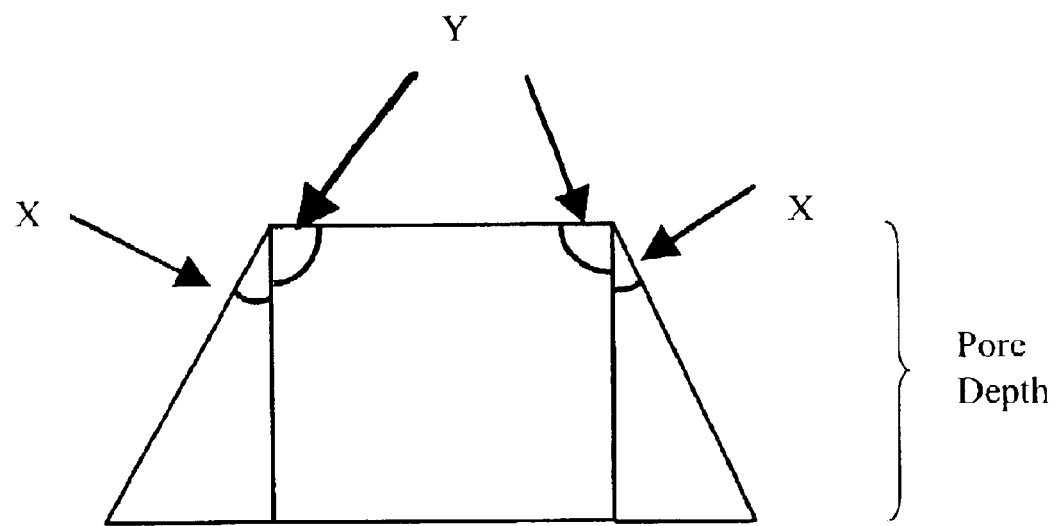
FIG. 4 depicts a cross section of a pore in a microfabricated filter of the present invention. The pore depth corresponds to the filter thickness. Y represents the right angle between the surface of the filter and the side of a pore cut perpendicularly through the filter, while X is the tapering angle by which a tapered pore differs in its direction through the filter from a nontapered pore.

Preferably, appropriate microfabrication or micromachining techniques are chosen to achieve a desired aspect ratio for the filter pores. The aspect ratio refers to the ratio of the slot depth (corresponding to the thickness of the filter in the region of the pores) to the slot width or slot length. The fabrication of filter slots with higher aspect ratios (i.e., greater slot depth) may involve deep etching methods. Many fabrication methods, such as deep RIE, useful for the fabrication of MEMS (micro electronic mechanical systems) devices can be used or employed in making the microfabricated filters. The resulting pores can, as a result of the high aspect ratio and the etching method, have a slight tapering, such that their openings are narrower on one side of the filter than the other. For example, in FIG. 4, the angle Y, of a hypothetical pore bored straight through the filter substrate is 90 degrees, and the tapering angle X by which a tapered pore of a microfabricated filter of the present invention differs from the perpendicular is between about 0 degree and about 90 degrees, and preferably between 0.1 degrees and 45 degrees and most preferably between about 0.5 degrees and 10 degrees, depending on the thickness of the filter (pore depth).

The present invention includes microfabricated filters comprising two or more tapered pores. The substrate on which the filter pores, slots or openings are fabricated or machined may be silicon, silicon dioxide, plastic, glass, ceramics or other solid materials. The solid materials may be porous or non-porous. Those who are skilled in microfabrication and micromachining fabrication may readily choose and determine the fabrication protocols and materials to be used for fabrication of particular filter geometries.

Using the microfabrication or micromachining methods, the filter slots, pores or openings can be made with precise geometries. Depending on the fabrication methods or materials used, the accuracy of a single dimension of the filter slots (e.g. slot length, slot width) can be within 20%, or less than 10%, or less than 5%. Thus, the accuracy of the critical, single dimension of the filter pores (e.g. slot width for oblong or quadrilateral shaped slots) for the filters of the present invention are made within, preferably, less than 2 microns, more preferably, less than 1 micron, or even more preferably less than 0.5 micron.

Preferably, filters of the present invention can be made using the track-etch technique, in which filters made of glass, silicon, silicon dioxides, or polymers such as polycarbonate or polyester with discrete pores having relatively-uniform pore sizes are made. For example, the filter can be made by adapting and applying the track-etch technique described at whatman.com/products/nucleopor.tech frame-.htm for Nucleopore Track-etch membranes to filter substrates. In the technique used to make membrane filters, a thin polymer film is tracked with energetic heavy ions to produce latent tracks on the film. The film is then put in an etchant to produce pores.

Preferred filters for the cell separation methods and systems of the present invention include microfabricated or micromachined filters that can be made with precise geometries for the openings on the filters. Individual openings are isolated with similar or almost identical feature sizes and are patterned on a filter. The openings can be of different shapes such as, for example, circular, quadrilateral, or elliptical. Such filters allow precise separation of particles based on their sizes and other properties.

In a preferred embodiment of a microfabricated filter, individual pores are isolated and of a cylindrical shape, and the pore size is within a 20% variation, where the pore size is calculated by the smallest and largest dimension of the pore (width and length, respectively).

Filter Comprising Electrodes

In some preferred embodiments, traveling-wave dielectrophoretic forces can be generated by electrodes built onto a chip that is part of a filtration chamber, and can be used to move sample components such as cells away from a filter. In this case, the microelectrodes are fabricated onto the filter surfaces and the electrodes are arranged so that the traveling wave dielectrophoresis can cause the sample components such as cells to move on the electrode plane or the filter surface through which the filtration process occur. A full description of the traveling wave dielectrophoresis is provided in U.S. application Ser. No. 09/679,024, entitled "Apparatuses Containing Multiple Active Force Generating Elements and Uses Thereof" filed Oct. 4, 2000, herein incorporated by reference in its entirety.

In one embodiment of the filters, interdigitated microelectrodes are fabricated onto the filter surfaces such as those shown in FIG. 2 or described in "Novel dielectrophoresis-based device of the selective retention of viable cells in cell culture media" by Docoslis et al, in Biotechnology and Bioengineening, Vol. 54, No. 3, pages 239–250, 1997, and in the U.S. Pat. No. 5,626,734, issued to Docoslis et al. on May 7, 1997. For this embodiment, the negative dielectrophoretic forces generated by the electrodes can repel the sample components such as the cells from the filter surface or from the filter slots so that the collected cells on the filters are not clogging the filters during the filtration process. Where traveling-wave dielectrophoresis or negative dielectrophoresis is used to enhance filtration, electrode elements can be energized periodically throughout the filtration process, during periods when fluid flow is halted or greatly reduced.

Filters having slots in the micron range that incorporate electrodes that can generate dielectrophoretic forces are illustrated in FIG. 3 (A and B). For example, filters have been made in which the interdigitated electrodes of 18 micron width and 18 micron gaps were fabricated on the filters, which were made on silicon substrates. Individual filter slots were of rectangular shape with dimensions of 100 micron (length) by 2–3.8 micron (width). Each filter had a unique slot size (e.g. length by width: 100 micron by 2.4 micron, 100 micron by 3 micron, 100 micron by 3.8 micron). Along the length direction, the gap between the adjacent filter slots was 20 micron. Along the width direction, the adjacent slots were not aligned; instead, they were offset. The offset distance between neighboring columns of the filter slots were 50 micron or 30 micron, alternatively. The filter slots were positioned with respect to the electrodes so that the slot center lines along the length direction were aligned with the center line of the electrodes, or the electrode edges, or the center line of the gaps between the electrodes.

The following discussion and references can provide a framework for the design and use of electrodes to facilitate filtration by translocating sample components, such as non-filterable cells, away from a filter:

Dielectrophoresis refers to the movement of polarized particles in a non-uniform AC electrical field. When a particle is placed in an electrical field, if the dielectric properties of the particle and its surrounding medium are different, the particle will experience dielectric polarization. Thus, electrical charges are induced at the particle/medium interface. If the applied field is non-uniform, then the interaction between the non-uniform field and the induced polarization charges will produce net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various publications (e.g., "Non-uniform Spatial Distributions of Both the Magnitude and Phase of AC Electric Fields determine Dielectrophoretic Forces by Wang et al., in *Biochim Biophys Acta* Vol. 1243, 1995, pages 185–194", "Dielectrophoretic Manipulation of Particles by Wang et al, in IEEE Transaction on Industry Applications, Vol. 33, No. 3, May/June, 1997, pages 660–669", "Electrokinetic behavior of colloidal particles in traveling electric fields: studies using yeast cells by Huang et al, in J. Phys. D: Appl. Phys., Vol. 26, pages 1528–1535", "Positioning and manipulation of cells and microparticles using miniaturized electric field traps and traveling waves. By Fuhr et al., in Sensors and Materials. Vol. 7: pages 131–146", "Dielectrophoretic manipulation of cells using spiral electrodes by Wang, X-B. et al., in *Biophys. J.* Volume 72, pages 1887–1899, 1997", "Separation of human breast cancer cells from blood by differential dielectric affinity by Becker et al, in Proc. Natl. Acad. Sci., Vol., 92, January 1995, pages 860–864"). The manipulation of microparticles with dielectrophoresis and traveling wave dielectrophoresis include concentration/aggregation, trapping, repulsion, linear or other directed motion, levitation, separation of particles. Particles may be focused, enriched and trapped in specific regions of the electrode reaction chamber. Particles may be separated into different subpopulations over a microscopic scale. Relevant to the filtration methods of the present invention, particles may be transported over certain distances. The electrical field distribution necessary for specific particle manipulation depends on the dimension and geometry of microelectrode structures and may be designed using dielectrophoresis theory and electrical field simulation methods.

The dielectrophoretic force $F_{DEP\ z}$ acting on a particle of radius r subjected to a non-uniform electrical field can be given by $$F_{DEP\ z} = 2\pi \epsilon_m r^3 \chi_{DEP} \nabla E_{rms}^2 \cdot \vec{a}_z$$

where $E_{rms}$ is the RMS value of the field strength, $\epsilon_m$ is the dielectric permitivity of the medium. $\chi_{DEP}$ is the particle dielectric polarization factor or dielectrophoresis polarization factor, given by $$\chi_{DEP} = \mathrm{Re}\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\epsilon_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEP\ z} = 2\pi \epsilon_m r^3 \chi_{DEP} V^2 p(z) \vec{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive and negative dielectrophoresis depends on whether particles are more or less polarizable than the surrounding medium. In the filtration methods of the present invention, electrode patterns on one or more filters of a filtration chamber can be designed to cause sample components such as cells to exhibit negative dielectrophoresis, resulting in sample components such as cells being repelled away from the electrodes on the filter surfaces.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD}=E\ \cos(2\pi(ft-z/\lambda_0))\bar{a}_x$ (i.e., a x-direction field is traveling along the z-direction) is given by $$F_{TWD} = -2\pi \in_m r^3 \zeta_{TWD} E^2 \cdot \bar{a}_z$$

where E is the magnitude of the field strength, $\in_m$ is the dielectric permittivity of the medium. $\zeta_{TWD}$ is the particle polarization factor, given by $$\zeta_{TWD} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $$\varepsilon_x^* = \varepsilon_x - j\frac{\sigma_x}{2\pi f}$$

is the complex permittivity (of the particle x=p, and the medium x=m). The parameters $\in_p$ and $\sigma_p$ are the effective permittivity and conductivity of the particle, respectively. These parameters may be frequency dependent.

Particles such as biological cells having different dielectric property (as defined by permittivity and conductivity) will experience different dielectrophoretic forces. For traveling-wave DEP manipulation of particles (including biological cells), traveling-wave DEP forces acting on a particle of 10 micron in diameter can vary somewhere between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

Both dielectrophoresis and traveling-wave dielectrophoresis forces acting on particles depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permittivities depending on the applied frequency), particles will experience positive dielectrophoresis forces and are directed towards the strong field regions. The particles that are less polarizable than the surrounding medium will experience negative dielectrophoresis forces and are directed towards the weak field regions. For traveling wave dielectrophoresis, particles may experience dielectrophoresis forces that drive them in the same direction as the field traveling direction or against it, dependent on the polarization factor $\zeta_{TWD}$. The following papers provide basic theories and practices for dielectrophoresis and traveling-wave-dielectrophoresis: Huang, et al., *J. Phys. D: Appl. Phys.* 26:1528–1535 (1993) ;Wang, et al., *Biochim. Biophys. Acta.* 1243:185–194 (1995); Wang, et al., *IEEE Trans. Ind. Appl.* 33:660–669 (1997).

Filtration Chamber

A filtration chamber or the present invention is any chamber that can contain a fluid sample that comprises or engages at least one microfabricated filter of the present invention. A filtration chamber of the present invention can comprise one or more fluid-impermeable materials, such as but not limited to, metals, polymers, plastics, ceramics, glass, silicon, or silicon dioxide. Preferably, a filtration chamber of the present invention has a volumetric capacity of from about 0.01 milliliters to about ten liters, more preferably from about 0.2 milliliters to about two liters. In some preferred embodiments of the present invention, a filtration chamber can have a volume of from about 1 milliliter to about 80 milliliters.

Figure 5:
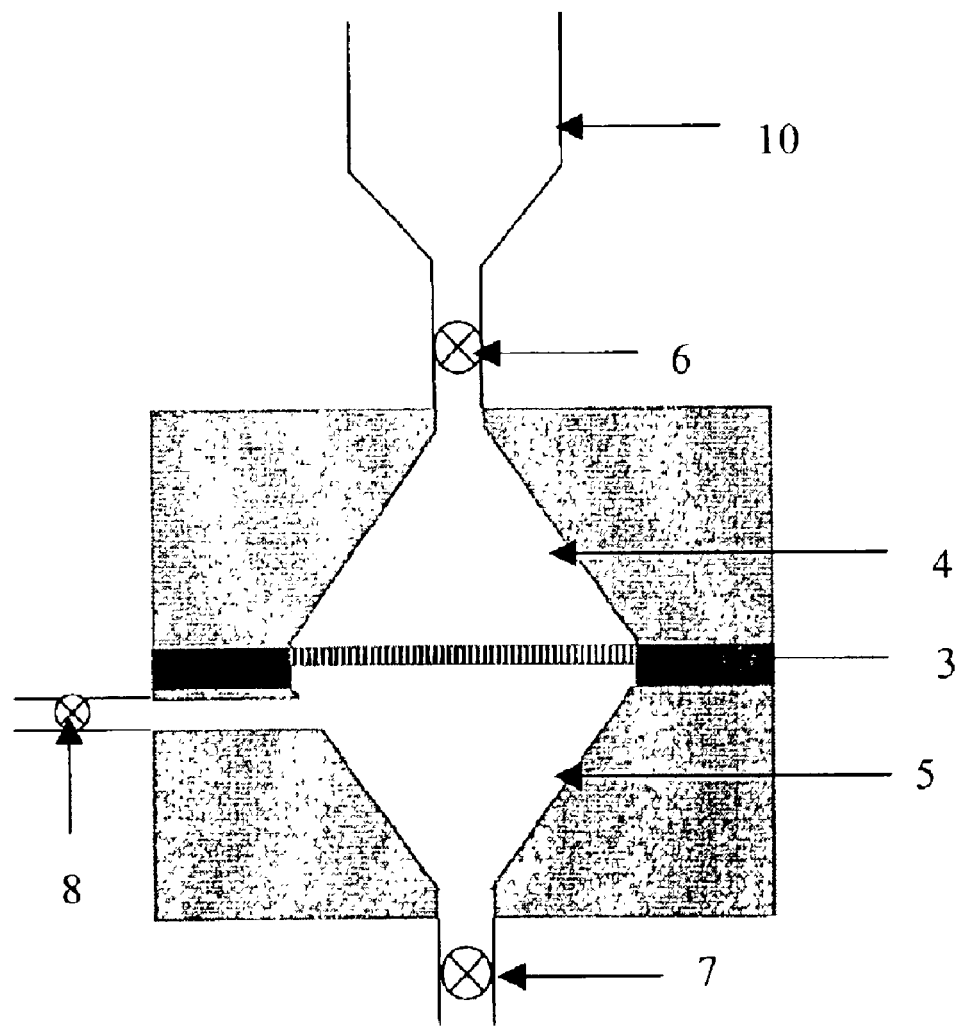
FIG. 5 depicts a filtration unit of the present invention having a microfabricated filter (3) separating the filtration chamber into an upper antechamber (4) and a post-filtration subchamber (5). The unit has valves to control fluid flow into and out of the unit: valve A (6) controls the flow of sample from the loading reservoir (10) into the filtration unit, valve B (7) controls fluid flow through the chamber by connection to a syringe pump, and valve C (8) is used for the introduction of wash solution into the chamber.
Figure 6:
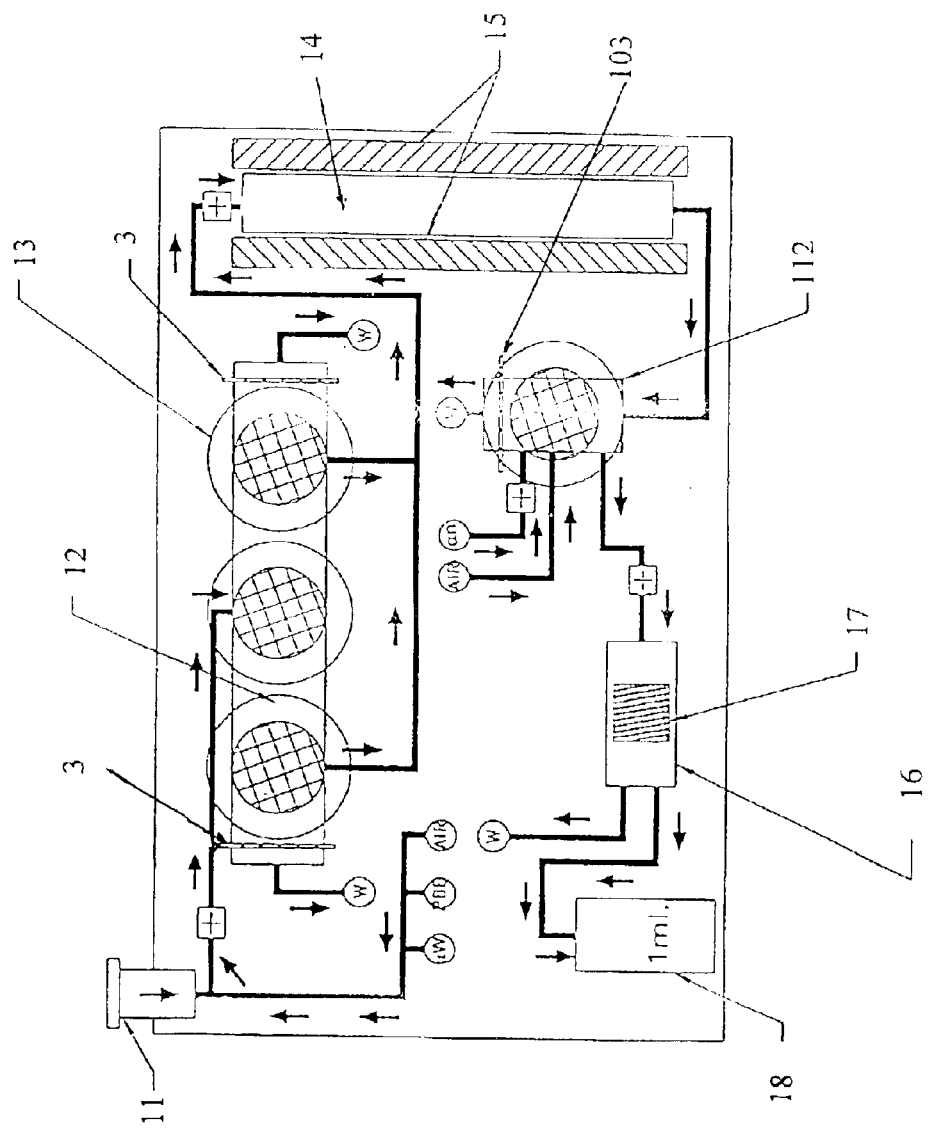
FIG. 6 is a diagram of an automated system of the present invention that comprises an inlet for the addition of a blood sample (11); a filtration chamber (12) that comprises acoustic mixing chips (13) and microfabricated filters (103); a magnetic capture column (14) having adjacent magnets (15); a mixing/filtration chamber (112); a magnetic separation chamber (16) comprising an electromagnetic chip (17), and a vessel for rare cell collection (18).

A filtration chamber of the present invention can comprise or engage any number of filters. In one preferred embodiment of the present invention, a filtration chamber comprises one filter (see, for example FIG. 5 and FIG. 14. In another preferred embodiment of the present invention, a filtration chamber comprises more than one filter, such as the chamber exemplified in FIG. 6 and FIG. 7. Various filter chamber configurations are possible. For example, it is within the scope of the present invention to have a filtration chamber in which one or more walls of the filter chamber comprises a microfabricated filter. It is also within the scope of the present invention to have a filtration chamber in which a filter chamber engages one or more filters. In this case, the filters can be permanently engaged with the chamber, or can be removable (for example, they can be inserted into slots or tracks provided on the chamber). A filter can be provided as a wall of a chamber, or internal to a chamber, and filters can optionally be provided in tandem for sequential filtering. Where filters are inserted into a chamber, they form are inserted to form a tight seal with the walls of a chamber, such that during the filtration operation, fluid flow through the chamber (from one side of a filter to the other) must be through the pores of the filter.

In embodiments in which a filtration chamber of the present invention comprises one or more microfabricated filters that are internal to the chamber, the filter or filters can divide the chamber into subchambers. Where a filtration chamber comprises a single internal microfabricated filter, for example, the filtration chamber can comprise a prefiltration "antechamber", or where appropriate, "upper subchamber" and a "post-filtration subchamber", or, where appropriate, "lower subchamber". In other cases, a microfabricated filter can form a wall of a filtration chamber, and during filtration, filterable sample components exit the chamber via the filter.

In some preferred embodiments of the present invention, a filtration chamber of the present invention has at least one port that allows for the introduction of a sample into the chamber, and conduits can transport sample to and from a filtration chamber of the present invention. When fluid flow commences, sample components that flow through one or more filters can flow into one or more areas of the chamber and then out of the chamber through conduits, and, preferably but optionally, from the conduits into a vessel, such as a waste vessel. The filtration chamber can also optionally have one or more additional ports for the additions of one or more reagents, solutions, or buffers.

In some preferred embodiments, a filtration chamber of the present invention is part of a filtration unit in which valves control fluid flow through the chamber. For example, one preferred filtration unit of the present invention, depicted in FIG. 5, comprises a valve-controlled inlet for the addition of sample (valve A (6)), a valve connected to a conduit through which negative pressure is applied for the filtration of the sample (valve B (7)), and a valve controlling the flow of wash buffer into the filtration chamber for washing the chamber (valve C (8)). In some preferred embodiments of the present invention, a filtration unit can comprise valves that can optionally be under automatic control that allow sample to enter the chamber, waste to exit the chamber, and negative pressure to provide fluid flow for filtration.

In a preferred embodiment of the present invention, a filtration chamber of, for example, approximately one centimeter by one centimeter by ten centimeters in dimensions can have one or more filters comprising from four to 1,000,000 slots, preferably from 100 to 250,000 slots. In this preferred embodiment, the slots are preferably of rectangular shape, with a slot length of from about 0.1 to about 1,000 microns, and slot width is preferably from about 0.1 to about 100 microns, depending on the application.

Figure 7:
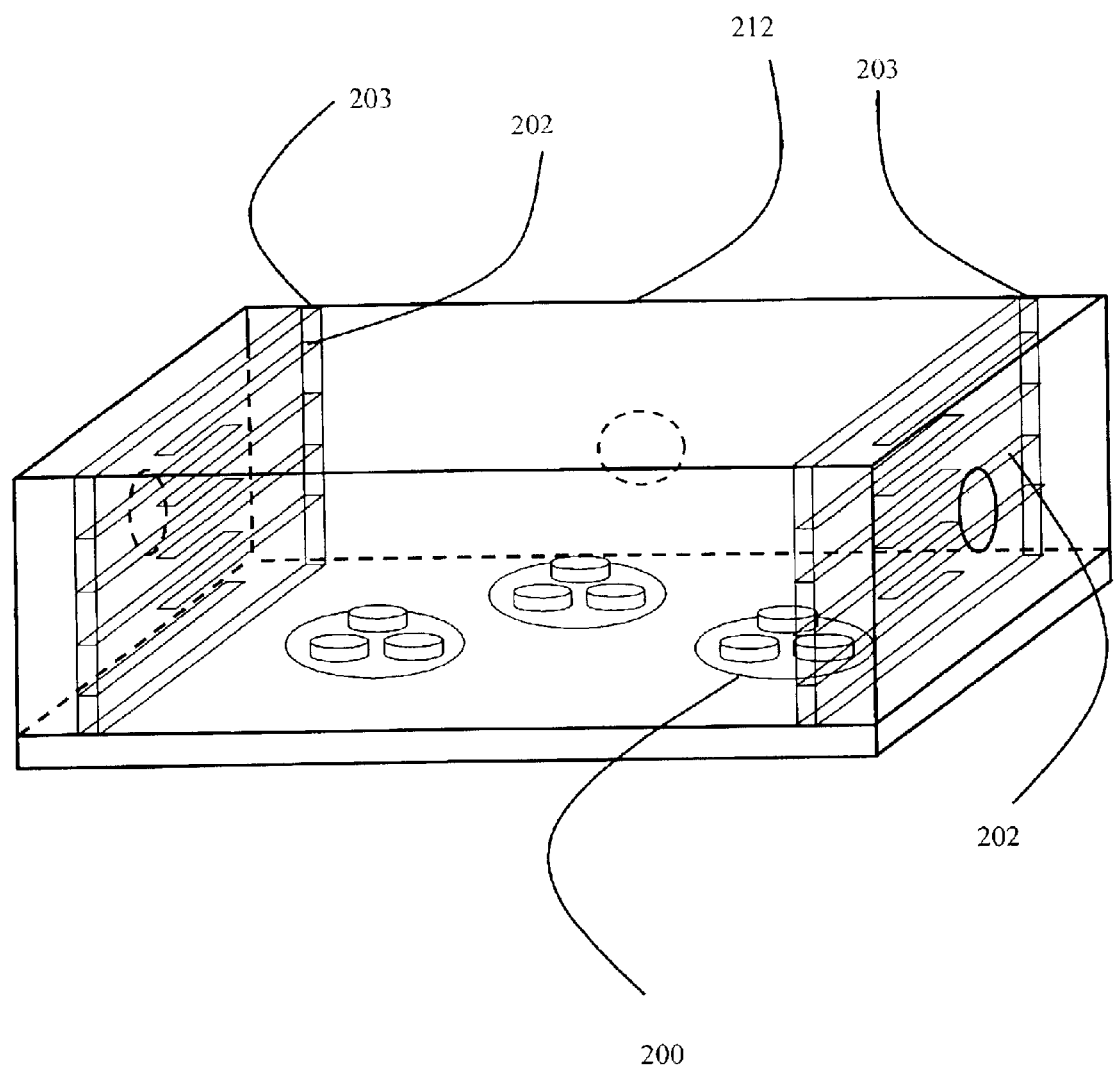
FIG. 7 depicts a three-dimensional perspective view of a filtration chamber of the present invention that has two filters (203) that comprise slots (202) and a chip having acoustic elements (200)(the acoustic elements may not be visible on the chip surface, but are shown here for illustrative purposes). In this simplified depiction, the width of the slots is not shown.
Figure 8:
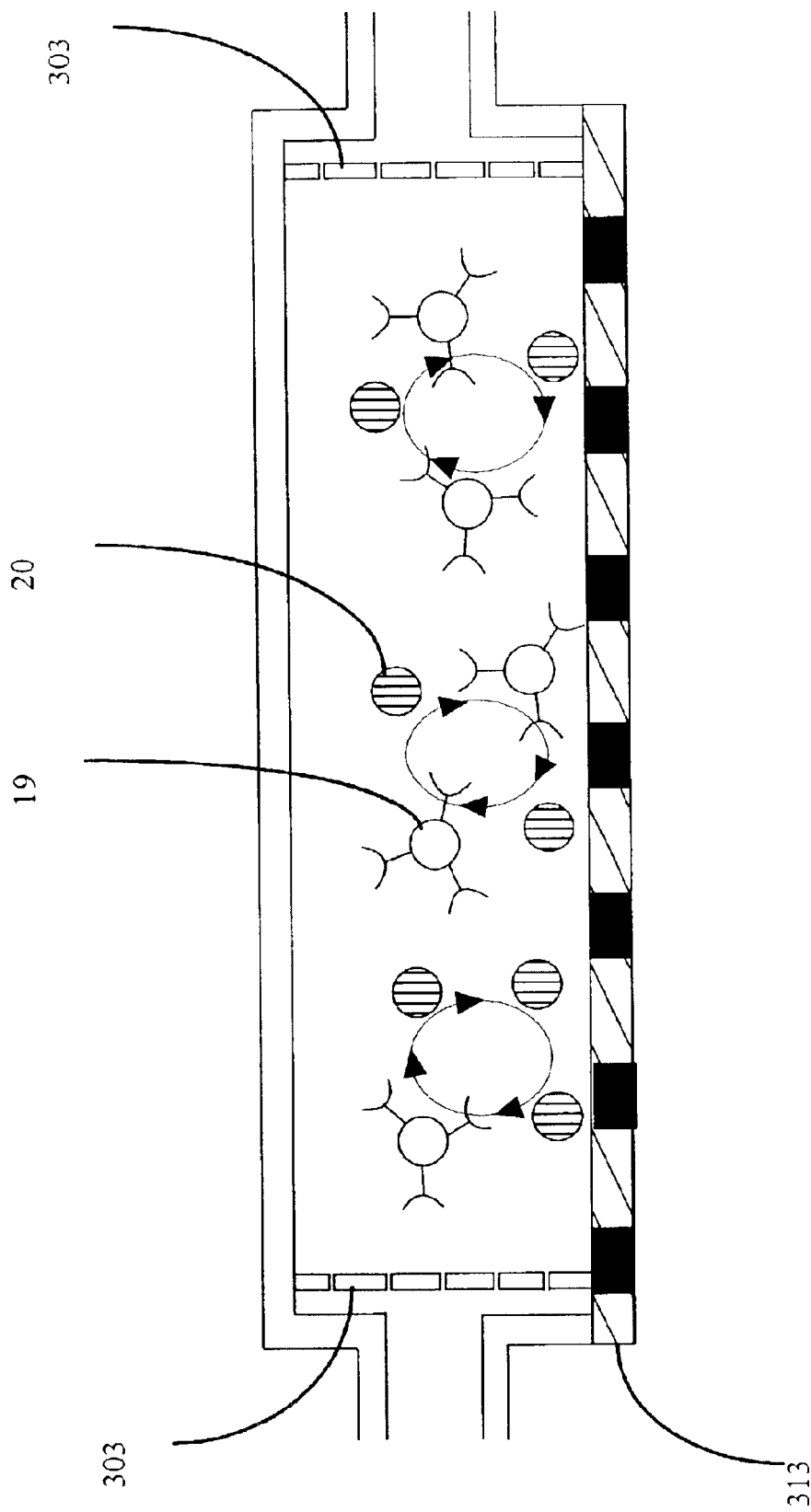
FIG. 8 depicts a cross-sectional view of a filtration chamber of the present invention having two filters (303) after filtering has been completed, and after the addition of magnetic beads (19) to a sample comprising target cells (20). The acoustic elements are turned on during a mixing operation.
Figure 9:
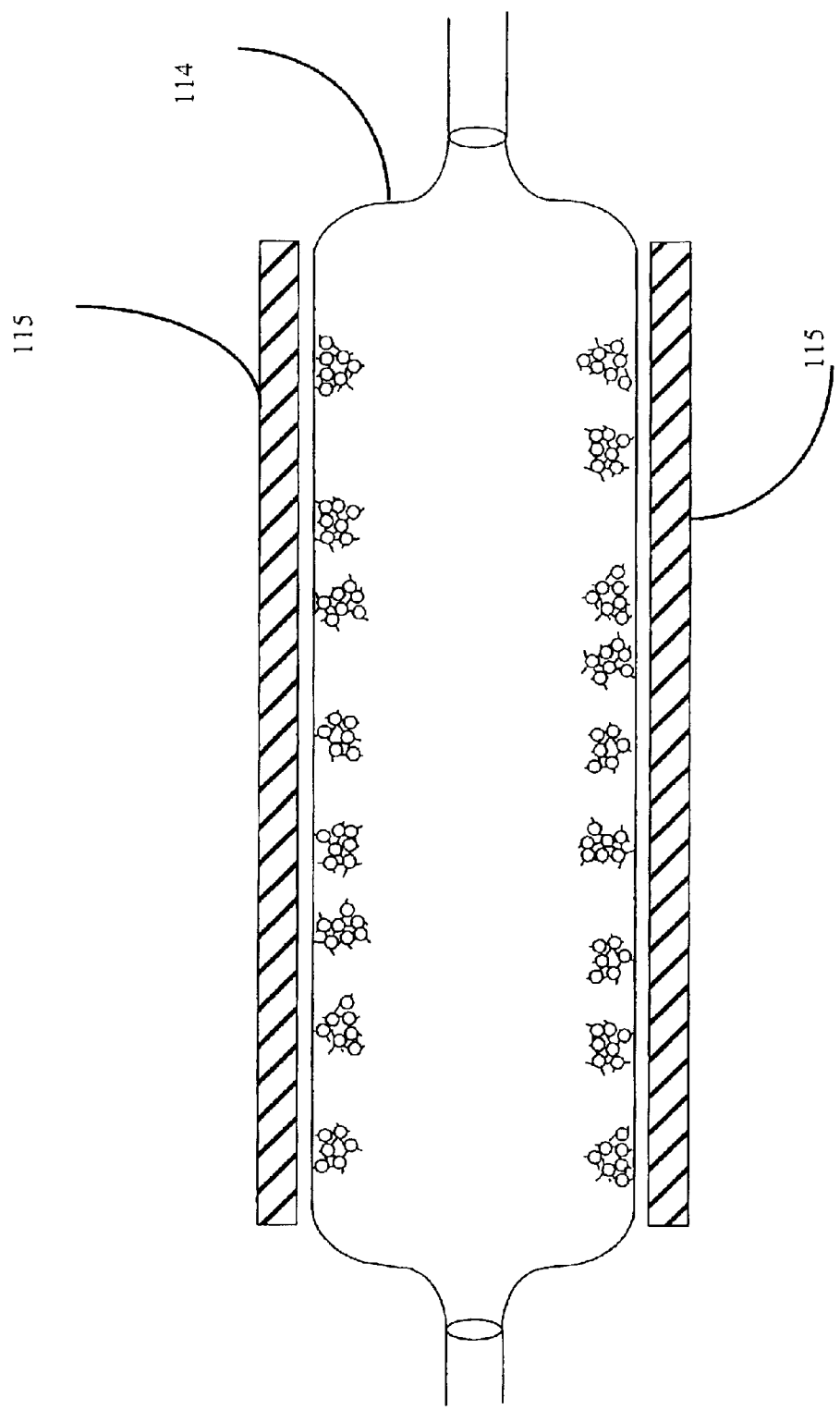
FIG. 9 depicts a cross-sectional view of a feature of an automated system of the present invention: a magnetic capture column (114). Magnets (115) are postioned adjacent to the separation column.
Figure 10:
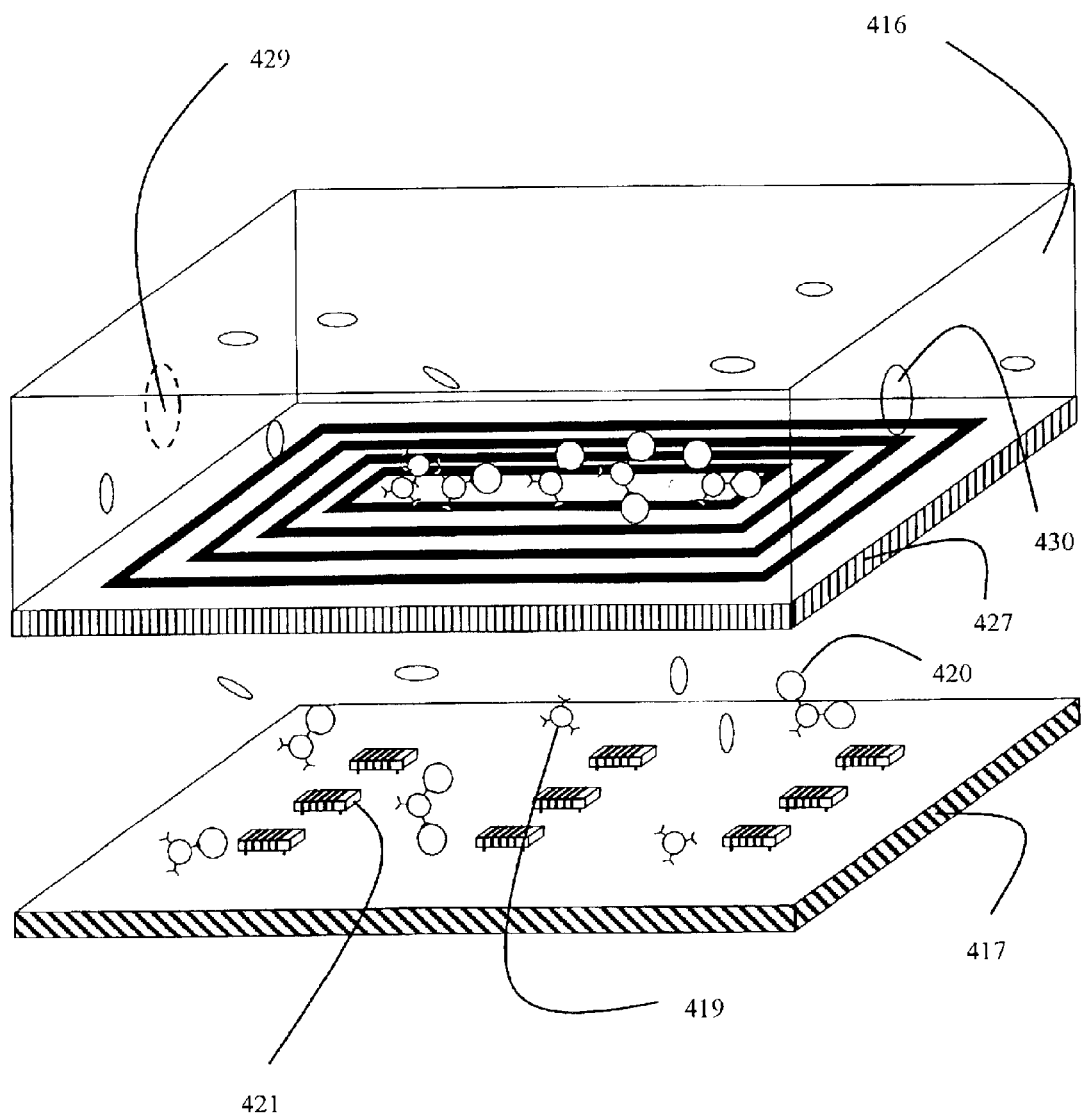
FIG. 10 depicts a three-dimensional perspective view of a chamber (416) of an automated system of the present invention that comprises a multiple force chip that can separate rare cells from a fluid sample. The chamber has an inlet (429) and an outlet (430) for fluid flow through the chamber. A cut-away view shows the chip has an electrode layer (427) that comprises an electrode array for dielectrophoretic separation and an electromagnetic layer (417) that comprises electromagnetic units (421) an electrode array on another layer. Target cells (420) are bound to magnetic beads (419) for electromagnetic capture.
Figure 14:
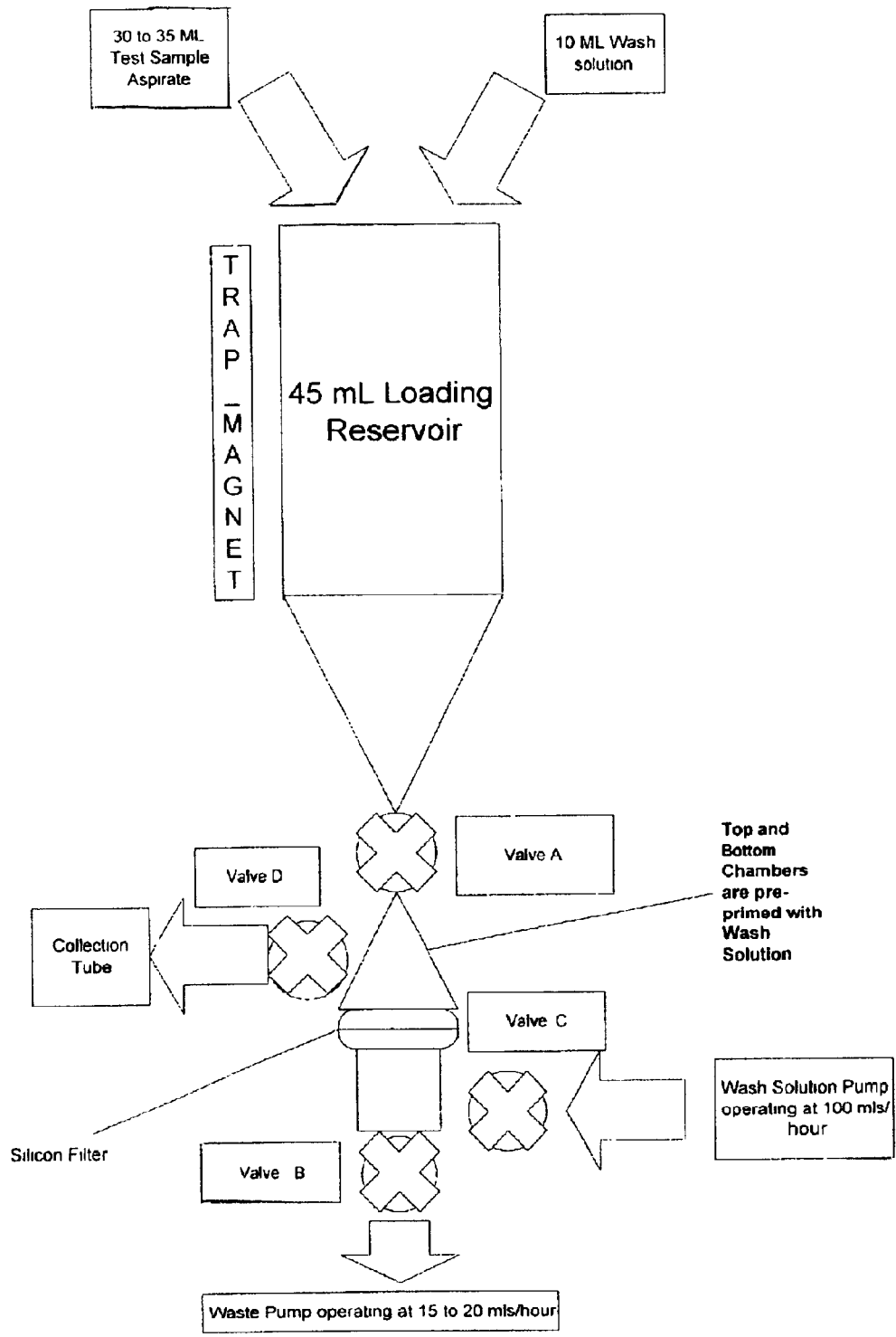
FIG. 14 is a schematic depiction of a filtration unit of the present invention.

Preferably, slots can allow for the passage of mature red blood cells (lacking nuclei) through the channels and thus out of the chamber, while not allowing cells having a greater diameter (for example, white blood cells and nucleated red blood cells) to exit the chamber. A filtration chamber that can allow the removal of red blood cells by fluid flow through the chamber, while retaining other cells of a blood sample, is illustrated in FIG. 7, FIG. 14, and FIG. 16. For example, for removing matured red-blood-cells from nucleated RBCs and white blood cells, slot widths between 2.5 and 6.0 microns, more preferably between 2.5 and 4.0 microns, could be used. Slot length could vary between, for example, 20 and 200 microns. Slot depth (i.e., filter membrane thickness) can vary between 40 and 100 microns. The slot width between 2.5 and 6.0 microns would allow the double-discoid-shaped RBCs to go through the slots while retaining the nucleated RBCs and WBCs with diameters larger than 7 micron.

Filtration Chamber Comprising Active Chip

A filtration chamber can also preferably comprise or engage at least a portion of at least one active chip, where an active chip is a chip that uses applied physical forces to promote, enhance, or facilitate processing or desired biochemical reactions of a sample, or and to decrease or reduce any undesired effects that might otherwise occur to or in a sample. An active chip of a filtration chamber of the present invention preferably comprises acoustic elements, electrodes, or even electromagnetic elements. An active chip can be used to transmit a physical force that can prevent clogging of the slots or around the structures used to create a filter (for example, blocks, dams, or channels, slots etched into and through the filter substrate) by components of the sample that are too large to go through the pores or slots or openings, or become aggregated at the pores or slots or openings. For example, when an electric signal is applied, acoustic elements can cause mixing of the components within the chamber, thereby dislodging nonfilterable components from the slots or pores. In an alternative embodiment, a pattern of electrodes on a chip can provide negative dielectrophoresis of sample components to move the nonfilterable components from the vicinity of the slots, channels, or openings around structures and allow access of filterable sample components to the slots or openings. Example of such electrode arrays fabricated onto a filter under a different operating mechanism of "dielectrophoretic-base selective retention" have been described in "Novel dielectrophoresis-based device of the selective retention of viable cells in cell culture media" by Docoslis et al, in Biotechnology and Bioengineering, Vol. 54, No. 3, pages 239–250, 1997, herein incorporated by reference and in the U.S. Pat. No. 5,626,734, issued to Docoslis et al on May 7, 1997, herein incorporated by reference. Active chips, including chips that can be used to mix samples by acoustic forces and chips that can be used to move moieties, including sample components, by dielectrophoretic forces, are described in U.S. application Ser. No. 09/636,104, filed Aug. 10, 2000, entitled "Methods for Manipulating Moieties in Microfluidic Systems", U.S. provisional application No. 60/239,299, entitled "An Integrated Biochip System for Sample Preparation and Analysis", filed Oct. 10, 2000, and U.S. application Ser. No. 09/686,737, filed Oct.10, 2000 entitled "Compositions and Methods for Separation of Moieties on Chips", all herein incorporated by reference.

The incorporation of electrodes that can be used for traveling wave dielectrophoresis on a filter of the present invention, as well as principles of dielectrophoresis and traveling wave dielectrophoresis, has been described herein in a previous description of microfabricated filters. Electrodes can also be incorporated onto active chips that are used in filtration chambers of the present invention to improve filtration efficiency.

A filtration chamber can also comprise a chip that comprises electromagnetic elements. Such electromagnetic elements can be used for the capture of sample components before or, preferably, after, filtering of the sample. Sample components can be captured after being bound to magnetic beads. The captured sample components can be either undesirable components to be retained in the chamber after the sample containing desirable components has already been removed from the chamber, or the captured sample components can be desirable components captured in the chamber after filtration.

An acoustic force chip can engage or be part of a filtration chamber, or one or more acoustic elements can be provided on one or more walls of a filtration chamber. Mixing of a sample by the activation of the acoustic force chip can occur during the filtration procedure. Preferably, a power supply is used to transmit an electric signal to the acoustic elements of one or more acoustic chips or one or more acoustic elements on one or more walls or a chamber. One or more acoustic elements can be active continuously throughout the filtration procedure, or can be activated for intervals (pulses) during the filtration procedure.

Sample components and, optionally, solutions or reagents added to the sample can be mixed by acoustic forces that act on both the fluid and the moieties, including, but not limited to, molecules, complexes, cells, and microparticles, in the chamber. Acoustic forces can cause mixing by acoustic streaming of fluid that occurs when acoustic elements, when energized by electrical signals generate mechanical vibrations that are transmitted into and through the fluid. In addition, acoustic energy can cause movement of sample components and/or reagents by generating acoustic waves that generate acoustic radiation forces on the sample components (moieties) or reagents themselves.

The following discussion and references can provide a framework for the design and use of acoustic elements to provide a mixing function:

Acoustic force refers to the force that is generated on moieties, e.g., particles and/or molecules, by an acoustic wave field. (It may also be termed acoustic radiation forces.) The acoustic forces can be used for manipulating, e.g., trapping, moving, directing, handling, mixing, particles in fluid. The use of the acoustic force in a standing ultrasound wave for particle manipulation has been demonstrated for concentrating erythrocytes (Yasuda et al, *J. Acoust. Soc. Am.*, 102(1):642–645 (1997)), focusing micron-size polystyrene beads (0.3 to 10 micron in diameter, Yasuda and Kamakura, *Appl. Phys. Lett,* 71(13):1771–1773 (1997)), concentrating DNA molecules (Yasuda et al, *J. Acoust. Soc. Am.*, 99(2):1248–1251, (1996)), batch and semicontinuous aggregation and sedimentation of cells (Pui et al, *Biotechnol. Prog.*, 11:146–152 (1995)). By competing electrostatic and acoustic radiation forces, separation of polystyrene beads of different size and charges have been reported (Yasuda et al, *J. Acoust. Soc. Am.*, 99(4):1965–1970 (1996); and Yasuda et al., *Jpn. J. Appl. Phys.*, 35(1):3295–3299 (1996)). Furthermore, little or no damage or harming effect was observed when acoustic radiation force was used to manipulate mammalian cells, as characterized in terms of ion leakage (for erythrocytes, Yasuda et al, *J. Acoust. Soc. Am.*, 102(1):642–645 (1997)) or antibody production (for hybridoma cells, Pui et al, *Biotechnol. Prog.*, 11:146–152 (1995)).

An acoustic wave can be established by an acoustic transducer, e.g., piezoelectric ceramics such as PZT material. The piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. When AC voltages are applied to the piezoelectric transducers, the vibration occurs to the transducers and such vibration can be coupled into a fluid that is placed in the chamber comprising the piezoelectric transducers.

An acoustic chip can comprise acoustic transducers so that when AC signals at appropriate frequencies are applied to the electrodes on the acoustic transducers, the alternating mechanical stress is produced within the piezoelectric materials and is transmitted into the liquid solutions in the chamber. In a situation where the chamber is set up so that a standing acoustic wave is established along the direction (e.g.: z-axis) of wave propagation and reflection, the standing wave spatially varying along the z axis in a fluid can be expressed as:

$$\Delta p(z) = p_0 \sin(kz)\cos(\omega t)$$

where $\Delta p$ is acoustic pressure at z, $p_0$ is the acoustic pressure amplitude, k is the wave number ($2\pi/\lambda$, where $\lambda$ is the wavelength), z is the distance from the pressure node, $\omega$ is the angular frequency, and t is the time. In one example, the standing-wave acoustic field may be generated by the superimposition of an acoustic wave generated from an acoustic transducer that forms a major surface of a chamber and the reflective wave from another major surface of the chamber that is positioned in parallel with the acoustic transducer and reflects the acoustic wave from the transducer. According to the theory developed by Yosioka and Kawasima (Acoustic Radiation Pressure on a Compressible Sphere by Yosioka K. and Kawasima Y. in Acustica, Volume 5, pages 167–173, 1955), the acoustic force $F_{acoustic}$ acting on a spherical particle in the stationary standing wave field is given by $$F_{acoustic} = -\frac{4\pi}{3} r^3 k E_{acoustic} A \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\rho_m$ and $\rho_p$ are the density of the particle and the medium, $\gamma_m$ and $\gamma_p$ are the compressibility of the particle and medium, respectively. The compressibility of a material is the product of the density of the material and the velocity of acoustic-wave in the material. The compressibility is sometimes termed acoustic impedance. A is termed as the acoustic-polarization-factor.

When A>0, the particle moves towards the pressure node (z=0) of the standing wave.

When A<0, the particle moves away from the pressure node. The acoustic radiation forces acting on particles depend on acoustic energy density distribution and on particle density and compressibility. Particles having different density and compressibility will experience different acoustic-radiation-forces when they are placed into the same standing acoustic wave field. For example, the acoustic radiation force acting on a particle of 10 micron in diameter can vary somewhere between <0.01 and >1000 pN, depending on the established acoustic energy density distribution.

The above analysis considers the acoustic radiation forces exerted on particles in a standing acoustic wave. Further analysis may be extended to the case of the acoustic radiation forces exerted on particles in a traveling-wave case. Generally, an acoustic wave field may consist of both standing and traveling-wave components. In such cases, particles in the chamber will experience acoustic radiation forces in the form other than those described by above equations. The following papers provide detailed analysis of acoustic radiation forces on spherical particles by traveling acoustic wave and standing acoustic waves: "Acoustic Radiation Pressure on a Compressible Sphere" by Yosioka K. and Kawasima Y. in Acustica, Volume 5, pages 167–173, 1955; and "Acoustic-Radiation force on a solid elastic sphere" by Hasegawa T. and Yosioka K. in Journal of Acoustic Society of America.

The acoustic radiation forces on particles may also be generated by various special cases of acoustic waves. For example, acoustic forces may be produced by a focused beam ("Acoustic radiation force on a small compressible sphere in a focused beam" by Wu and Du, *J. Acoust. Soc. Am.*, 87:997–1003 (1990)), or by acoustic tweezers ("Acoustic tweezers" by Wu *J. Acoust. Soc. Am.*, 89:2140–2143 (1991)).

Acoustic wave field established in a fluid can also induce a time-independent fluid flow, as termed acoustic streaming. Such fluid flow may also be utilized in biochip applications or microfluidic applications for transporting or pumping fluids. Furthermore, such acoustic-wave fluid flow may be exploited for manipulating molecules or particles in fluids.

The acoustic streaming depends on acoustic field distributions and on fluid properties ("Nonlinear phenomena" by Rooney J. A. in "Methods of Experimental Physics: Ultrasonics, Editor: P. D. Edmonds", Chapter 6.4, pages 319–327, Academic Press, 1981; "Acoustic Streaming" by Nyborg W. L. M. in "Physical Acoustics, Vol. II-Part B, Properties of Polymers and Nonlinear Acoustics, Chapter 11, pages 265–330).

Thus, one or more active chips, such as one or more acoustic force chips, can also be used to promote mixing of reagents, solutions, or buffers, that can be added to a filtration chamber, before, during, or after the addition of a sample and the filtration process. For example, reagents, such as, but not limited to specific binding members that can aid in the removal of undesirable sample components, or in the capture of desirable sample components, can be added to a filtration chamber after the filtration process has been completed and the conduits have been closed off. The acoustic elements of the active chip can be used to promote mixing of one or more specific binding members with the sample whose volume has been reduced by filtration. One example is the mixing of sample components with magnetic beads that comprise antibodies that can bind particular cell types (for example, white blood cells, or fetal nucleated red blood cells) within the sample. The magnetic beads can be used to selectively remove or separate (capture) undesirable or desirable sample components, respectively, in subsequent steps of a method of the present invention. The acoustic elements can be activated for a continuous mixing period, or in pulses.

II. Method of Enriching Rare Cells of a Fluid Sample Using Microfiltration

The present invention provides methods of enriching rare cells of a fluid sample using filtration through a microfabricated filter of the present invention that comprises at least one tapered pore. The method includes: dispensing a sample into a filtration chamber that comprises or engages at least one microfabricated filter that comprises at least one tapered pore; providing fluid flow of the sample through the filtration chamber, such that components of the fluid sample flow through or are retained by the one or more microfabricated filters based on the size, shape, or deformability of the components; and collecting enriched rare cells from said filtration chamber. In some embodiments, filtration can separate soluble and small components of a sample from at least a portion of the cells that are in the sample, in order to concentrate the retained cells to facilitate further separation and analysis. In some aspects, filtration can remove undesirable components from a sample, such as, but not limited to, undesirable cell types. Where filtration reduces the volume of a sample by at least 50% or removes greater than 50% of the cellular components of a sample, filtration can be considered a debulking step. The present invention contemplates the use of filtration for debulking as well as other functions in the processing of a fluid sample, such as, for example, concentration of sample components or separation of sample components (including, for example, removal of undesirable sample components and retention of desirable sample components).

Sample

A sample can be any fluid sample, such as an environmental sample, including air samples, water samples, food samples, and biological samples, including suspensions, extracts, or leachates of environmental or biological samples. Biological samples can be blood, a bone marrow sample, an effusion of any type, ascites fluid, pelvic wash fluid, or pleural fluid, spinal fluid, lymph, serum, mucus, sputum, saliva, urine, semen, occular fluid, extracts of nasal, throat or genital swabs, cell suspension from digested tissue, or extracts of fecal material. Biological samples can also be samples of organs or tissues, including tumors, such as fine needle aspirates or samples from perfusions of organs or tissues. Biological samples can also be samples of cell cultures, including both primary cultures and cell lines. The volume of a sample can be very small, such as in the microliter range, and may even require dilution, or a sample can be very large, such as up to about two liters for ascites fluid. A preferred sample is a blood sample.

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

The rare cells to be enriched from a sample can be of any cell type present at less than one million cells per milliliter of fluid sample or that constitute less than 1% of the total nucleated cell population in a fluid sample. Rare cells can be, for example, bacterial cells, fungal cells, parasite cells, cells infected by parasites, bacteria, or viruses, or eukaryotic cells such as but not limited to fibroblasts or blood cells. Rare blood cells can be RBCs (for example, if the sample is an extract or leachate containing less than than one million cells per milliliter RBCs), subpopulations of blood cells and blood cell types, such as WBCs, or subtypes of WBCs (for example, T cells or macrophages), or can be nucleated red blood cells, including fetal nucleated red blood cells. Rare cells can be stem cells of any type. Rare cells can also be cancer cells, including neoplastic cells and malignant cells. Rare cells of a blood sample can also be non-hematopoietic cells, such as but not limited to epithelial cells.

Dispensing of Sample into Filtration Chamber

A sample can be dispensed into a filtration chamber of the present invention by any convenient means. As nonlimiting examples, sample can be introduced using a conduit (such as tubing) through which a sample is pumped or injected into the chamber, or can be directly poured, injected, or dispensed or pipeted manually, by gravity feed, or by a machine. Dispensing of a sample into a filtration chamber of the present invention can be directly into the filtration chamber, or can be into a conduit that leads to a filtration chamber, or into a vessel that leads, via one or more conduits, to a filtration chamber.

Filtering

Following the addition to a filtration chamber of the present invention, filtering is effected by providing fluid flow through the chamber. Fluid flow can be provided by any means, including positive or negative pressure (for example, by a manual or machine operated syringe-type system), pumping, or even gravity. The filtration chamber can have ports that are connected to conduits through which a buffer or solution and the fluid sample or components thereof can flow. A filtration unit can also have valves that can control fluid flow through the chamber. When the sample is added to the filtration chamber, and fluid flow is directed through the chamber, filter slots can allow the passage of fluid, soluble components of the samples, and filterable non-soluble components of a fluid sample through a filter, but, because of the slot dimensions, can prevent the passage of other components of the fluid sample through the filter.

Preferably, fluid flow through a filtration chamber of the present invention is automated, and performed by a pump or positive or negative pressure system, but this is not a requirement of the present invention. The optimal flow rate will depend on the sample being filtered, including the concentration of filterable and nonfilterable components in the sample and their ability to aggregate and clog the filter. For example, the flow rate through the filtration chamber can be from less than 1 milliter per hour to more than 1000 milliliters per hour, and flow rate is in no way limiting for the practice of the present invention. Preferably, however, filtration of a blood sample occurs at a rate of from 5 to 500 milliliters per hour, and more preferably at a rate of between about 10 and about 50 milliliters per hour.

In fabricating the filter slots through the filter substrate, slight tapering of the slot along the slot depth direction can occur. Thus a particular slot width may not be maintained constant throughout the entire depth of the filter and the slot width on one surface of the filter is typically larger than the width on the opposite surface. In utilizing such filters with tapered slot width, it is preferred to have the narrow-slot side of the filter facing the sample, so that during filtering the sample goes through the narrow-width side of the slot first and then filtered cells exit at the wide-width side of the slot. This avoids trapping cells that are being filtered within the funnel-shaped slots. However, the orientation of a filter with one or more tapered slots is not a restriction in using the filters of the present invention. Depending on specific applications, the filters can also be used in the orientation such that the wide-width side of the filter slots faces the sample.

In the methods of the present invention, preferably desirable components, such as rare cells whose enrichment is desired, are retained by the filter. Preferably, in the methods of the present invention as rare cells of interest of the sample are retained by the filter and one or more undesirable components of the sample flow through the filter, thereby enriching the rare cells of interest of the sample by increasing the proportion of the rare cells to total cells in the filter-retained portion of the sample, although that is not a requirement of the present invention. For example, in some embodiments of the present invention, filtration can enrich rare cells of a fluid sample by reducing the volume of the sample and thereby concentrating rare cells.

Additional Enrichment Steps

The present invention also contemplates using filtration in combination with other steps that can be used in enriching rare cells of a fluid sample. For example, debulking steps or separation steps can be used prior to or following filtration.

Debulking

For example, in preferred aspects of the present invention in which the fluid sample is a blood sample, a majority of the non-nucleated red blood cells (RBCs) that make up more than 90% of the cellular components of a blood sample can be removed during a debulking step.

A debulking step can be, as nonlimiting examples, a selective sedimentation step, a selective lysis step, a concentration step, a centrifugation step, or a filtration step. Preferred debulking steps are those that reduce the volume of a fluid sample and at the same time allow the technician to select portions of the centrifuged, filtered, or selectively sedimented product that retain desirable components and do not retain at least a portion of some undesirable components.

Centrifugation can reduce the volume of a sample by pelleting insoluble components of a sample, or can separate components on the basis of density, and can make use of density gradients that can also separate components of a sample, such as different cell types. A preferred debulking step used in the methods of the present invention is the application of the collected sample to density equilibrium gradients. When used in the debulking of blood samples, density equilibrium gradient centrifugation can separate erythrocytes (non-nucleated red blood cells or RBCs) from white blood cells (WBCs) and nucleated red blood cells (nRBCs), such as fetal nucleated red blood cells (see, for example, U.S. Pat. No. 6,210,889 issued Apr. 3, 2001 to Drouin et al., herein incorporated by reference). For example, density gradients can be made using components such as Ficoll, Percoll, Ficoll-Hypaque, Nycodenz, Polymorphprep, or Histopaque. When gradients are used as a debulking step in the separation of fetal nucleated red blood cells from maternal blood, the maternal blood sample can be separated after density gradient centrifugation into a supernatant, one or more mononuclear cell layers, and a pellet containing non-nucleated erythrocytes. The one or more mononuclear layers are separated from the other layers to obtain a fraction that is enriched in fetal nucleated red blood cells.

In addition to one or more filtration steps using one or more microfabricated filters of the present invention, other types of filtration can also be employed as debulking steps. In reducing the volume of a sample, filtration can also selectively retain some components of a sample based on size, shape, or degree of deformability, while removing other components. Filtration can be performed by using columns packed with various resins or polymeric materials, by using membranes of pore sizes that allow retention of desirable components, by using channels that are microetched into one or more chips, by using "bricks" or dams that are built onto the surface of a chip, or by using slots or pores that are microetched into a solid surface that can be within a chamber or form a wall of a chamber.

For example, "bricks" (that can be of any shape or dimension) can be built onto a chip that is part of a chamber, and one or more blocks can be of a height that extends from the surface of the chip to the top of the chamber, and can be positioned such that the distance between the bricks (or between a brick and a chamber wall) will allow the passage of fluid and some insoluble components of a sample, but will not allow the passage of insoluble sample components that are larger than a particular size. Examples of the manufacture and use of bricks (called "obstacles") is described in U.S. Pat. No. 5,837,115 issued Nov. 17, 1998 to Austin et al., herein incorporated by reference in its entirety. A fluid sample can be introduced into the chamber, and fluid flow can drive the movement of the fluid through the chamber, thereby removing a significant volume of the fluid sample while retaining at least some of the components of the sample in the chamber. Using a similar strategy, one or more "dams" can be built onto a chip that extend upward from the surface of the chip and leave an opening of a defined width between the top of the dam and the top wall of the chamber (see, for example, U.S. Pat. No. 5,726,026 issued Mar. 10, 1998 to Wilding et al., herein incorporated by reference in its entirety). In yet another strategy, channels or "tunnels" in a chip can be of a certain width or range or widths, and thus act as a sieve through which some components of a sample can pass whereas others are retained when fluid flow through the channels commences.

Another method for debulking of blood is through selective sedimentation of erythrocytes (red blood cells) by using certain reagents. Preferably, such agglutination and sedimentation of erythrocytes does not affect the cells of interest in the blood samples, and the loss of the target cells (i.e. the cells of interest) is as small as possible. For example, PrepaCyte™ cell separation medium (supplied by BioErgonomics, Inc., St. Paul, Minn.) can be used for such purposes. The PrepaCyte™ is a mixture of antibodies in a medium which facilitates the agglutination and sedimentation of erythrocytes, platelets and myeloid components of peripheral blood, resulting in a significant (99% or above) removal of RBCs (see "Cytokine and cytokine receptor expression as a biological indicator of immune activation: important considerations in the development of in vitro model systems", in Journal of Immunological Methods, Volume 243, page 125–145, 2000 by Daniel P. Collins). The PrepaCyte™ was developed for producing separated fractions enriched in T-lymphocytes and hematopoietic progenitor cells from blood samples.

A preferred debulking method using PrepaCyte™ is as follows: 1) a blood sample is mixed and incubated with PrepaCyte™ cell separation medium for a specified length of time (e.g. 30 minutes). The recommended volume ratio of the blood to PrepaCyte™ from the manufacture (BioErgonomics, Inc.) is 1:1. 2) after mixing, the tubes or beakers that hold the blood and PrepaCyte™ sample are placed upright and cells are allowed to settle for certain length of time (for example 30 minutes). The majority of erythrocytes, the majority of platelets, and some other cells (for example mature myeloid cells, some B-cells, some NK-cells) are agglutinated and precipitated in the tubes or beakers while remaining the cells remain in the suspension. This simple procedure can remove 99% or above of erythrocytes from original blood samples. After processing with PrepaCyte™ medium, the cells in the suspension can be harvested via centrifugation and then resuspended, resulting in a significantly reduced sample volume (because RBCs have been removed). The volume reduction can be about 50%, or as high as 90%, depending on the final cell concentration in the suspension. Although PrepaCyte™ was developed for producing separated fractions enriched in T-lymphocytes and hematopoictic progenitor cells from blood samples, PrepaCyte™ can also be used to remove RBCs from maternal blood samples, as the majority of the nucleated red blood cells (of either maternal or fetal origin) remain in suspension after the RBCs are agglutinated and precipitated (see Example 5). Thus, PrepaCyte™ medium can be used for debulking of blood samples in the applications of separating and enriching fetal nucleated RBCs from maternal blood samples.

Other mediums containing different reagents such as certain cell types, certain proteins, or antibodies, used with different or similar procedures, can also be used. For example, wheat germ agglutinin (e.g., see "Erythrocyte agglutination by wheat germ agglutinin: ionic strength dependence of the contact seam topology" in Mol. Membr. Biol. Volume 18(2), pages 169–176, 2001, by Rolfe M, Parmar A, Hoy T G, Coakley W T.) and some RBC antibodies (see, e.g., "Antibody-mediated red blood cell agglutination resulting in spontaneous echocardiographic contrast", in Pediatric Cardiology, Volume 20(4), pages 287–289, 1999, by Miller M R, Thompson W R, Casella J F, Spevak P J.) can also facilitate agglutination and precipitation of red blood cells. The present invention also includes solutions for sedimenting RBCs that combine specific binding members that bind RBCs with dextran, described herein, that can be used in methods that also use filtration to enrich rare cells from a blood sample.

Another method for debulking blood sample is the use of hypotonic solutions. By treating blood samples with hypotonic solutions, red blood cells can be selectively lysed, or red blood cells can be altered significantly so that they become readily separable from white blood cells and other nucleated cells. Alternatively, certain biochemical reagents may be used to selectively lyse red blood cells. Some solutions that selectively lyse red blood cells are described in U.S. patent application Ser. No. 09/973,629 incorporated by reference in their entireties.

Preferably, at least one debulking step is performed before a filtration step (that also optionally but preferably performs a debulking function), although this is not a requirement of the present invention. More than one debulking step can be employed in the methods of the present invention. For example, in some applications, undesirable components of the sample can be removed in steps subsequent to a first debulking step. It can then practical and advantageous to further reduce the volume of the remaining sample. This can be done through any of the described debulking methods, using scaled down volumes and areas where appropriate.

Separation Steps

The methods of the present invention can include filtration through a microfabricated filter of the present invention in combination with one or more separation steps. In general, a separation step will selectively remove one or more undesirable components from a sample, or selectively separate one or more desirable components of a sample. These steps will depend on the properties of the particular cells to be removed or separated from the sample, such as their binding properties, physical properties such as size or density, and electrical properties.

Filtration Plus Selectively Removing Undesirable Components

The present invention includes methods in which filtration is combined with the selective removal of one or more undesirable components of a fluid sample.

Preferably, in the methods of the present invention, selective removal of one or more undesirable components of a fluid sample makes use of specific recognition of one or more undesirable components by one or more specific binding members. A specific binding member used to remove undesirable components of a sample can be any type of molecule or substrate that can specifically bind one or more undesirable components. Receptor ligands (either naturally occurring, modified, or synthetic), antibodies, and lectins are nonlimiting examples of specific binding members that can be used in the methods of the present invention. More than one different specific binding member can be used to capture one or more undesirable components to a solid support. Preferably, a specific binding member used in the methods of the present invention to selectively remove one or more undesirable components does not appreciably bind to desirable components, such as rare cells, of the fluid sample. In most applications of the present invention, a specific binding member used in the methods of the present invention to selectively remove one or more undesirable components does not appreciably bind to the rare cells of the fluid sample that are to be enriched. By "does not appreciably bind" is meant that not more than 30%, preferably not more than 20%, more preferably not more than 10%, and yet more preferably not more than 1.0% of the rare cells of the fluid sample that are to be enriched using the methods of the present invention are bound by the specific binding member used to selectively remove undesirable components of the fluid sample. Preferred specific binding members used in the methods of the present invention include antibodies, particularly antibodies that recognize and bind cell surface epitopes.

Specific binding members that bind to one or more undesirable components of the present invention can be used to capture one or more undesirable components, such that one or more desirable components of the fluid sample can be removed from the area or vessel where the undesirable components are bound. In this way, the undesirable components are separated from other components of the sample that include the rare cells to be separated. The capture can be effected by attaching antibodies that recognize the undesirable component or components to a solid support, or by binding secondary specific binding members that recognize the antibodies that bind the undesirable component or components, to a solid support, such that the undesirable components become attached to the solid support and become fixed at a particular location. A solid support can be, as nonlimiting examples, a surface, such as a plastic or polymeric surface, a gel or polymer, a membrane, the surface of a chip, or a bead. In the present invention, magnetic beads are preferred solid supports for the capture and selective removal of undesirable components of a sample.

The capture of undesirable components of a sample can be direct or indirect. For direct capture, a first specific binding member that binds to one or more undesirable components of a sample can be attached to a solid support. The one or more undesirable components, when contacted with the solid support, then bind to the solid support. For indirect capture, a primary specific binding member that binds to one or more undesirable components of a sample can be contacted with the one or more undesirable components, and a secondary specific binding member that can bind the primary specific binding member can be attached to a solid support. When the undesirable components that have bound the primary specific binding member are contacted with the solid support, the one or more undesirable components of the sample can bind the solid support via the primary and secondary specific binding members. In certain preferred embodiments of the present invention where selective removal of one or more undesirable components of a sample is performed, direct capture is preferred, as direct capture can comprise fewer steps, including washing procedures.

Magnetic beads are preferred solid supports for use in the methods of the present invention. Magnetic beads are known in the art, and are available commercially. Magnetic beads can be purchased that are coated with secondary specific binding members, for example secondary antibodies or streptavidin. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are coated with either a secondary binding member such as streptavidin or a primary specific binding member such as an antibody that can bind a cell that is to removed from the sample. Where streptavidin coated beads are used, the primary specific binding member is preferably biotinylated (for example a biotinylated antibody) such that the streptavidin coated bead will bind a sample component that is bound to the biotinylated antibody through a streptavidin-biotin link. Methods of using magnetic beads in the capture of directly or indirectly bound cells are well known in the art, and are also described in the examples provided.

In preferred embodiments of the present invention, the fluid sample is a maternal blood sample, the rare cells whose separation is desirable are fetal cells, and the undesirable components of the sample to be removed from the sample are white blood cells. In these embodiments, a specific binding member that selectively binds white blood cells is used to remove the white blood cells from the sample by magnetic capture. Preferably, the specific binding member is either used to coat magnetic beads for direct capture, or is used in biotinylated form for indirect capture of white blood cells by streptavidin-coated magnetic beads.

Preferably, a specific binding member that selectively binds white blood cells is an antibody that binds white blood cells but does not appreciably bind fetal nucleated red blood cells, such as, for example, CD3, CD11b, CD14, CD17, CD31, CD45, CD50, CD53, CD63, CD69, CD81, CD84, CD102, or CD166. Antibodies can be tested for their ability to bind an efficiently remove white blood cells and allow for the enrichment or rare cells of interest from a sample using capture assays well known in the art.

A debulked sample, such as a debulked blood sample, can be incubated with one or more specific binding members, such as, but not limited to, antibodies, that specifically recognize one or more undesirable components of a fluid sample. Where a filtration chamber has been used for debulking the sample, mixing and incubation of one or more specific binding members with the sample can optionally be performed in a filtration chamber. The one or more undesirable components can be captured, either directly or indirectly, via their binding to the specific binding member. For example, a specific binding member can be bound to a solid support, such as a bead, membrane, or column matrix, and following incubation of the fluid sample with the specific binding member, the fluid sample, containing unbound components, can be removed from the solid support. Alternatively, one or more primary specific binding members can be incubated with the fluid sample, and, preferably following washing to remove unbound specific binding members, the fluid sample can be contacted with a secondary specific binding member that can bind or is bound to a solid support. In this way the one or more undesirable components of the sample can become bound to a solid support, enabling separation of the undesirable components from the fluid sample.

In a preferred aspect of the present invention, a debulked blood sample from a pregnant individual is incubated with magnetic beads that are coated with antibody that specifically binds white blood cells and does not appreciably bind fetal nucleated red blood cells. The magnetic beads are collected using capture by activated electromagnetic units (such as on an electromagnetic chip), or capture by at least one permanent magnet that is in physical proximity to a vessel, such as a tube or column, that contains the fluid sample. After capture of the magnetic beads by the magnet, the remaining fluid sample is removed from the vessel. The sample can be removed manually, such as by pipeting, or by physical forces such as gravity, or by fluid flow through a separation column. In this way, undesirable white blood cells can be selectively removed from a maternal blood sample. The sample can optionally be further filtered using a microfabricated filter of the present invention. Filtration preferably removes residual red blood cells from the sample and can also further concentrate the sample.

In one preferred embodiment, after incubation of magnetic beads that comprise a specific binding member that specifically bind undesirable components with a sample, the sample is transported through a separation column that comprises or engages at least one magnet. As the sample flows through the column, undesirable components that are bound to the magnetic beads adhere to one or more walls of the tube adjacent to the magnet or magnets. An alternative embodiment uses a magnetic separator, such as the magnetic separator manufactured by Immunicon. Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343 having, filed Sep. 18, 2001, entitled "Individually Addressable Micro-Electromagnetic Unit Array Chips"and U.S. application Ser. No. 09/685,410, filed Oct. 10, 2000, entitled "Individually Addressable Micro-Electromagnetic Unit Array Chips in Horizontal Configurations". In yet another preferred embodiment, a tube that contains the sample and magnetic beads is positioned next to one or more magnets for the capture of nondesirable components bound to magnetic beads. The supernatant, depleted of the one or more nondesirable components, can be removed from the tube after the beads have collected at the tube wall.

In some preferred embodiments of the present invention, removal of white blood cells from a sample is performed simultaneously with debulking the blood sample by selective sedimentation of red blood cells. In these embodiments, a solution that selectively sediments red blood cells is added to a blood sample, and a specific binding member that specifically binds white blood cells that is bound to a solid support, such as magnetic beads, is added to the blood sample. After mixing, red blood cells are allowed to settle, and white blood cells are captured, such as by magnetic capture. This can be conveniently performed in a tube to which a sedimenting solution and the specific binding member, preferably bound to magnetic beads, can be added. The tube can be rocked for a period of time for mixing the sample, and then positioned next to one or more magnets for the capture of the magnetic beads. In this way, in a single incubation and separation step, approximately 99% of RBCs and 99% of WBCs can be removed from a sample. The supernatant can be removed from the tube and subjected to filtration using a microfabricated filter of the present invention. Filtration removes remaining RBCs, resulting in a sample in which rare cells, such as, for example, fetal cells, cancer cells, or stem cells, have been enriched.

Figure 22:
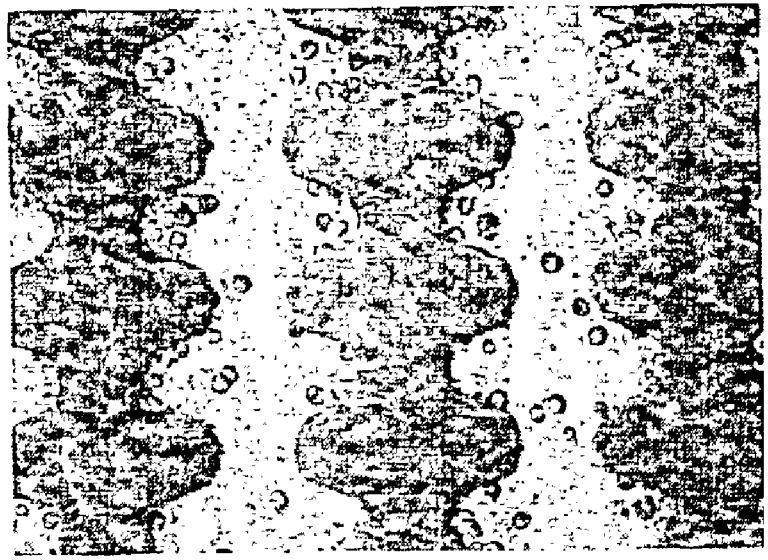
FIG. 22 depicts white blood cells of a blood sample retained on electrodes of a dielectrophoresis chip.

Undesirable components of a sample can be removed by methods other than those using specific binding members. For example, the dielectrical properties of particular cell types can be exploited to separate undesirable components dielectrophoretically. For example, FIG. 22 depicts white blood cells of a diluted blood sample retained on electrodes of a dielectrophoresis chip after red blood cells have been washed through the chamber.

Filtering Plus Separating Desirable Components

The present invention also includes methods in which filtration is combined with the separation of one or more desirable components, such as rare cells whose enrichment is desired, from a fluid sample. Preferably, separation of rare cells from a fluid sample occurs after at least one filtration step, but this is not a requirement of the present invention.

In some preferred embodiments of the present invention, separating rare cells uses at least one specific binding member that specifically binds the one or more rare cells and capture of the rare cells to a solid support. Receptor ligands (either of natural sources, modified, or synthetic), antibodies, and lectins are nonlimiting examples of specific binding members that can be used in the methods of the present invention. More than one different specific binding member can be used to capture one or more rare cells to a solid support.

Capture of cells, viruses, molecules, and other moieties to solid supports is well known in the arts of cell biology, biochemistry, and antibody technology, and can use a variety of formats. For example, a specific binding member that binds rare cells can be added to the sample. In a subsequent step, the specific binding member can be specifically bound by a secondary specific binding member that is used to bind the undesirable component to a solid support. For example, the specific binding member can be biotinylated, and can be bound by streptavidin that is coupled to a solid support etc.). The solid support can be of any type, but is preferably a bead or particle, a membrane, a polymeric surface (for example of a well or dish), or a column matrix. After adding the specific binding member to the sample and allowing the specific binding member to bind the rare cells, the fluid sample comprising unbound components is removed.

In many cases it can be preferable to provide the specific binding member that binds the rare cells already bound to a solid support. For example, beads, such as magnetic beads, to which one or more specific binding members that bind the rare cells are attached can be added to the sample, or the sample can be passed over a solid support such as a membrane or the surface of a plate that comprises a specific binding member, or through a solid support such as a column matrix that comprises a specific binding member. Using specific binding members that are directly bound to a solid support can increase the efficiency of the enrichment procedure.

In preferred embodiments, separation of one or more rare cells of the sample using specific binding members to capture the rare cells to a solid support, and can be performed in a dish, well, tube, column, or other vessel. Preferably, the solid support comprises magnetic beads. A magnet can be used to capture the magnetic beads to at least one side of a tube or separation column, or the magnetic beads can be captured using an active chip comprising electromagnetic elements, such as the chips described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". All are incorporated by reference in their entireties.

A specific binding member can be any type of molecule or substrate that can specifically bind one or more rare cell types. Preferably, a specific binding member used in the methods of the present invention to separate one or more rare cell types does not appreciably bind to undesirable components of the fluid sample. By "does not appreciably bind" is meant that not more than 30%, preferably not more than 20%, more preferably not more than 10%, and yet more preferably not more than 1.0% of one or more undesirable components are bound by the specific binding member used to separate rare cells from the fluid sample. Preferred specific binding members used in the methods of the present invention include antibodies, particularly antibodies that recognize and bind antigens on the surface of rare cells.

In a particularly preferred embodiment, the fluid sample is a blood sample and fetal nucleated red blood cells are the rare cells to be enriched. In this case, specific binding members such as lectins and antibodies can be used to bind and remove white blood cells. For example, lectins such as but not limited to concanavalin A, Dolichos biforus agglutinin, Datura Stramonium lectin, Sambucus Nigra lectin, Erythrina Cristagalli lectin, Griffonia Simplicifolia lectin I, Griffonia Simplicifolia lectin II, Lens culinaris agglutinin, Lycopersicon esculentum lectin, Maackia amurensis lectin, phaseolus vulgaris lectin, phaseolus vulgaris agglutinin leucoagglutinin, phaseolus vulgaris agglutinin erythroagglutinin, peanut agglutinin, Pisum Sativum Agglutinin, Ricinus Communis Agglutinin I, Soybean Agglutinin, Sophora Japonica Agglutinin, Solanum Tuberosum lectin, Succinylated wheat germ agglutinin, Ulex europaeous agglutinin I, wheat germ agglutinin, or Artocarpus integrifolia agglutinin.

Antibodies can also be used as specific binding members to capture fetal nucleated red blood cells from a blood sample. For example, a CD71 antibody can be used (see Example 7 and Table 5). An antibody or antibodies can also be used to enrich other rare cells such as, for example, cancer cells or stem cells from fluid samples such as urine or blood samples. Antibodies, lectins, or other specific binding members can be tested for their ability to bind an efficiently separate particular rare cell types from a sample using capture assays well known in the art.

A filtered or debulked sample, such as a debulked or filtered blood sample, can be incubated with one or more specific binding members, such as antibodies, that specifically recognize one or more rare cell types of a fluid sample. The one or more rare cell types can be captured, via their direct or indirect binding to the specific binding member, and the remainder of the fluid sample can be removed from the area, surface, or vessel where the rare cells being isolated are bound. For example, a specific binding member can be bound to a solid support, such as a membrane or column matrix, and following incubation of the fluid sample with the specific binding member, the fluid sample, containing unbound components, can be removed from the solid support. Alternatively, one or more primary specific binding members can be incubated with the fluid sample, and following washing to remove unbound primary specific binding members, the fluid sample can be contacted with a secondary specific binding member that can bind or is bound to a solid support. In this way the one or more rare cell types of the sample can become bound to a solid support, enabling separation of rare cells from the fluid sample. A solid support can be, as nonlimiting examples, a surface, such as a plastic surface, a gel or polymer, a membrane, the surface of a chip, or a bead. In the present invention, magnetic beads are preferred solid supports for the separation and capture of rare cells of a sample.

The capture of rare cells of a sample can be direct or indirect. For direct capture, a first specific binding member that binds to one or more rare cells of a sample can be attached to a solid support. The rare cells, when contacted with the solid support, then bind to the solid support. For indirect capture, a primary specific binding member that binds to the desirable rare cells of a sample can be contacted with the one or more rare cells, and a secondary specific binding member that can bind the primary specific binding member can be attached to a solid support. When the rare cells that have bound the primary specific binding member are contacted with the solid support, the one or more rare cells of the sample can bind the solid support via the primary and secondary specific binding members.

Magnetic beads are preferred solid supports for use in the methods of the present invention. Magnetic beads are known in the art, and are available commercially. Magnetic beads can be purchased that are coated with secondary specific binding members, for example secondary antibodies or streptavidin. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are coated with either streptavidin, a secondary antibody, or a primary antibody that can bind a cell that is to separated from the sample. Where streptavidin coated beads are used, the primary specific binding member is preferably biotinylated (for example a biotinylated primary antibody) such that the streptavidin coated bead will bind a sample component that is bound to the biotinylated antibody through a streptavidin-biotin link. Methods of using magnetic beads in the capture of directly or indirectly bound cells are well known in the art, and are also described in the examples provided. The methods of capture can use permanent magnets, such as permanent magnets positioned within or alongside a tube, dish, or vessel that contains the target cell-magnetic bead complexes, or commercially available magnetic separators that include permanent magnets (Immunicon). Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations".

The following discussion and references can provide a framework for the design and use of electromagnetic chips to facilitate separation of rare cells coupled to magnetic microparticles,:

Magnetic forces refer to the forces acting on a moiety, e.g., a particle, due to the application of a magnetic field. In general, particles have to be magnetic or paramagnetic when sufficient magnetic forces are needed to manipulate particles. We consider the example of a typical magnetic particle made of super-paramagnetic material. When the particle is subjected to a magnetic field $\overline{B}$, a magnetic dipole $\overline{\mu}$ is induced in the particle $$\overline{\mu} = V_p(\chi_p - \chi_m)\frac{\overline{B}}{\mu_m},$$
$$= V_p(\chi_p - \chi_m)\overline{H}_m$$

where $V_p$ is the particle volume, $\chi_p$ and $\chi_m$ are the volume susceptibility of the particle and its surrounding medium, $\mu_m$ is the magnetic permeability of medium, $\overline{H}_m$ is the magnetic field strength. The magnetic force $\overline{F}_{magnetic}$ acting on the particle is determined by the magnetic dipole moment and the magnetic field gradient:

$$\overline{F}_{magnetic} = -0.5\ V_p(\chi_p - \chi_m)\overline{H}_m \cdot \nabla \overline{B}_m,$$

where the symbols "•" and "∇" refer to dot-product and gradient operations, respectively. Clearly, whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{F_{magnetic}}{6\pi r \eta_m}$$

where r is the particle radius and $\eta_m$ is the viscosity of the surrounding medium. Thus to achieve sufficiently large magnetic manipulation force, the following factors should be considered: (1) the volume susceptibility of the magnetic particles should be maximized; (2) magnetic field strength should be maximized; and (3) magnetic field strength gradient should be maximized.

Magnetic fields can be established in fluidic chambers by applying electric currents to microelectromagnetic elements or by placing a permanent magnet in close proximity of a chamber or column. Each microelectromagnetic element is capable of producing magnetic field upon applying DC and/or AC electric currents. An electromagnetic element may be an electric wire wrapped as a loop, or an electric coil wrapped around a magnetic core. A number of types of electromagnetic elements are described in the co-pending U.S. patent application Ser. No. 09/399,299, filed on Sep. 16, 1999, and co-pending U.S. patent application Ser. No. 09/685,410 filed on Oct. 10, 2000, both of which are incorporated by reference in their entireties. Those electromagnetic elements can be incorporated in the system of the present invention. Other examples of electromagnetic units that can be incorporated include, but are not limited to, the following. Ahn, C., et al., *J. Microelectromechanical Systems.* Volume 5: 151–158 (1996); Ahn, C., et al., *IEEE Trans. Magnetics.* Volume 30: 73–79 (1994); Liakopoulos et al., in *Transducers* 97, pages 485–488, presented in 1997 International Conference on Silid-State Sensors and Actuators, Chicago, Jun. 16–19, 1997; U.S. Pat. No. 5,883,760 by Naoshi et al.

As an exemplary embodiment, the electromagnetic chip may incorporate an array of individually addressable electromagnetic units. These units are positioned or structurally arranged in certain order so that when each of or some of or all of electromagnetic units are energized (=magnetized), desired magnetic field distributions can be established to produce magnetic forces acting on magnetic particles. In another example, the electromagnetic chip may comprise multiple, interconnected electromagnetic units so that these units can be turned on or off in a synchronized order. Yet, in another example, the electromagnetic chip may comprise only one electromagnetic unit that can be energized to produce magnetic fields.

Manipulation of magnetic particles includes the directed movement, focusing and trapping of magnetic particles. The motion of magnetic particles in a magnetic field is termed "magnetophoresis". Theories and practice of magnetophoresis for cell separation and other applications may be found in various literatures (e.g., Magnetic Microspheres in Cell Separation, by Kronick, P. L. in Methods of Cell Separation, Volume 3, edited by N. Catsimpoolas, 1980, pages 115–139; Use of magnetic techniques for the isolation of cells, by Safarik I. And Safarikova M., in J. of Chromatography, 1999, Volume 722(B), pages 33–53; A fully integrated micromachined magnetic particle separator, by Ahn C. H. et al., in J. of Microelectromechanical systems, 1996, Volume 5, pages 151–157)

In preferred embodiments of the present invention, the fluid sample is a maternal blood sample, and the rare cells whose separation from the sample is desired are fetal nucleated red blood cells. In these embodiments, a specific binding member that specifically binds nucleated red blood cells is used to separate the nucleated red blood cells from the remainder of the blood sample by magnetic capture. Preferably, the specific binding member is either used to coat magnetic beads for direct capture, or is used in biotinylated form for indirect capture of nucleated red blood cells by streptavidin-coated magnetic beads. Preferably, a specific binding member that selectively binds nucleated red blood cells is an antibody that binds nucleated red blood cells but does not appreciably bind non-nucleated red blood cells or white blood cells. A preferred antibody for the separation of nucleated red blood cells from a blood sample is an anti-CD71 antibody.

In a preferred aspect of the present invention, a debulked blood sample is incubated with magnetic beads coated with an antibody, such as, but not limited to, an anti-CD71 antibody, that recognizes fetal nucleated red blood cells. The fetal nucleated red blood cells are captured using an electromagnetic chip, such as that described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". The remaining fluid sample is then removed from the captured beads that adhere to the surface of the chip, such as by fluid flow, leaving a preparation of enriched fetal red blood cells.

Alternatively, the fetal nucleated red blood cells are captured using a permanent magnet. A permanent magnet can be positioned alongside or within a tube, dish, or vessel that contains the debulked sample. The fluid sample is removed from the tube, dish, or vessel by, for example, aspiration or pipeting, leaving the magnetically separated cells in the tube, dish, or vessel.

Magnetic capture strategies can be used in isolating other types of rare cells, such as but not limited to cancer cells, from bodily fluid samples such as blood or urine, using specific binding members that specifically bind the rare cells.

Rare cells of the present invention can also be separated from a fluid sample using dielectrophoretic forces. The use of dielectrophoretic forces can be employed where the rare target cells have dielectrophoretic properties than are significantly different than other components that remain in the sample. That is, the difference in dielectrophoretic properties between rare target cells and nondesirable sample components must be sufficient to allow dielectrophoretic separation using micro-scale electrodes that can be built into or onto a chip. In most cases in which the fluid sample is a biological fluid sample, the other components of the sample whose dielectric properties must be taken into account are cells, such as cells that are not rare target cells. The feasibility of using dielectrophoresis for the separation of rare target cells can therefore depend on whether nondesirable components having similar dielectrophoretic properties as the target cells. Preferably, then, in applications of the method where a sample comprises a type of non-target cells that have similar dielectrophoretic properties as the target cells, selective removal of the type of non-target cells using methods other than dielectrophoresis has been performed prior to dielectrophoretic separation of target cells. Preferably in such instances, the selective removal of the non-target cells with similar dielectric properties using methods other than dielectrophoresis has been efficient, where efficiency refers to the percentage of non-target cells removed. The level of efficiency can vary with the application, but preferably the efficiency of selective removal of non-target cells with similar dielectric properties is greater than 30% of the non-target cells removed, more preferably greater than 50% of the non-target cells removed, and more preferably yet, greater than 90% of the non-target cells removed, and even more preferably, greater than 99% of the non-target cells removed in the selective removal step.

The previous discussion and references provided for the design and use of micro-electrodes to facilitate filtration by translocating sample components, such as nonfilterable cells, away from a filter using dielectrophoresis are also relevant to the use of micro-electrodes to facilitate dielectrophoretic separation of rare target cells. Various dielectrophoresis separation methods, such as those described in U.S. application Ser. No. 09/686,737, filed Oct. 10, 2000 entitled "Compositions and Methods for Separation of Moieties on Chips", in U.S. application Ser. No. 09/636,104, filed Aug. 10, 2000, entitled "Methods for Manipulating Moieties in Microfluidic Systems", and in U.S. application Ser. No. 09/679,024, entitled "Apparatuses Containing Multiple Active Force Generating Elements and Uses Thereof" filed Oct. 4, 2000, all herein incorporated by reference in their entireties, may be employed for separating rare target cells.

A preferred embodiment of the present invention is the separation of fetal nucleated red blood cells from a blood sample using a chip or chamber that comprises microelectrodes. The following discussion and references can provide a framework for the dielectrophoretic separation of nucleated red blood cells (nRBC) and red blood cells (RBCs):

Cell dielectric properties depend on cell structure composition. Non-nucleated red blood cells (RBCs) and nucleated red blood cells (nRBCs) will have different dielectric properties because of their differences in lacking and having a cell nucleus. The cell nucleus has an electrically poorly-conducting nuclear membrane surrounding the conductive interior of the nucleus. A theoretical analysis was used to determine whether the dielectric properties between RBCs and nRBCs are sufficiently large to allow dielectrophoretic separation of the two populations.

So-called dielectric shell models (e.g., Huang et al., Phys. Med. Biol. 37: 1499–1517 (1992)) have been employed for this analysis. For an RBC without a nucleus, a single shell model is used where the single shell represents the cell membrane. Thus, RBCs are modeled as conducting spheres (corresponding to cell interiors) surrounded by poorly-conducting thin shells (corresponding to cell membranes). Because of the double-discoid shape of the RBCs, we have used an ellipshere model (Kakuutani et al, Bioelectrochemistry & Bioenergetics 31: 131–145 (1993)) to simulate RBCs. For an nRBC, a three shell model is used where the three shells represent the cell membrane, cytoplasm, and nuclear membrane, respectively.

Figure 11:
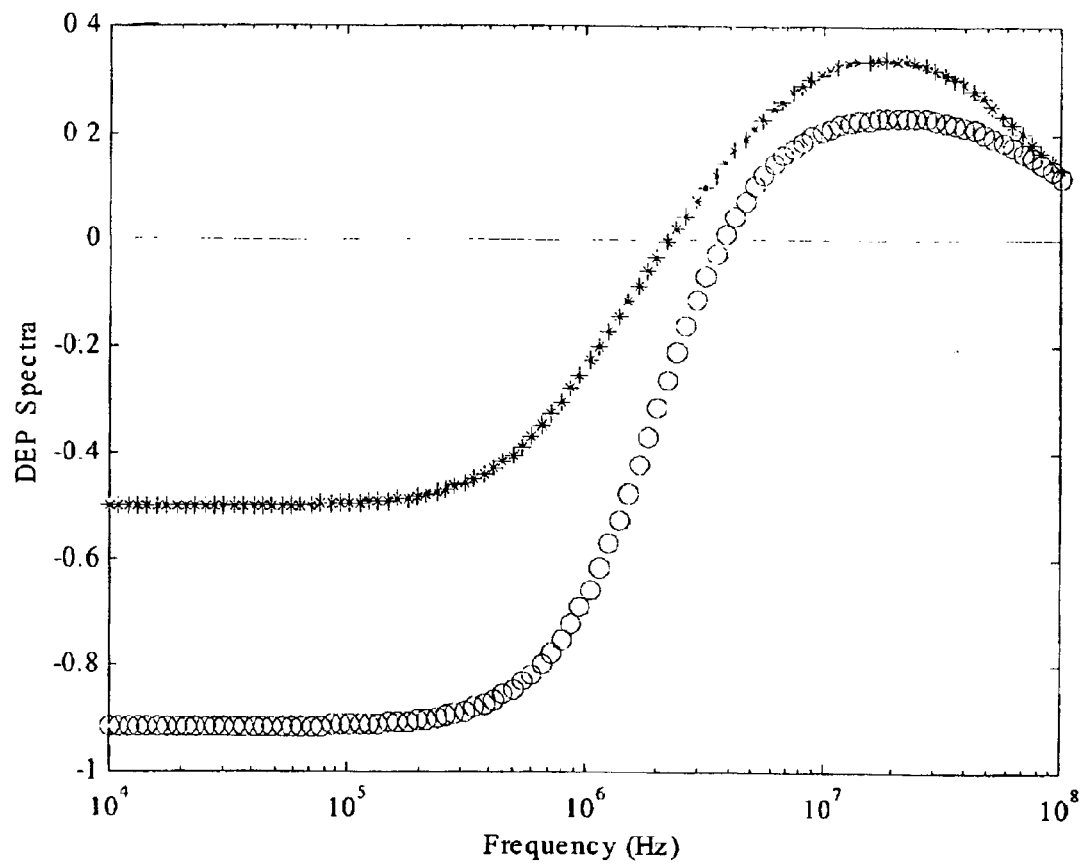
FIG. 11 shows a graph illustrating the theoretical comparison between the DEP spectra for an nRBC (Xs) and a RBC (circles) when the cells are suspended in a medium of electrical conductivity of 0.2 S/m.

FIG. 11 illustrates the theoretical DEP spectra for an RBC and an nRBC under two different suspension conditions. It is evident that nRBC and RBC exhibit different dielectrophoretic responses, especially in the frequency range of 1–10 MHz. For a suspending medium of electrical conductivity of approximately 0.2 S/m, nRBCs exhibit positive DEP at frequencies higher than 2.2 MHz whilst RBCs do not exhibit positive DEP until frequencies are higher than 3.6 MHz. Thus at frequency around 3 MHz, RBC and nRBC will have dielectrophoretic responses of opposite polarities.

Under these conditions, RBCs would exhibit negative DEP forces and be repelled from the electrodes whilst nRBCs would exhibit positive DEP forces and be collected to and trapped by the electrodes.

In some applications of the present invention, separation of rare cells from a fluid sample may exploit the differences in cell physical properties. For example, as discussed above, dielectrophoresis may be used to separate nucleated red blood cells from maternal red blood cells (non-nucleated). By exploiting the differences in their dielectric properties, nucleated red blood cells and mature red blood cells (and reticulocytes) are caused to exhibit positive and negative (or small positive) dielectrophoresis forces, respectively, under certain cell suspension and electric field conditions. When the cell suspension is introduced to a chamber containing microelectrodes on the bottom surface, nucleated red blood cells can be collected and retained on the electrodes whilst the red blood cells are carried away from the chamber together with the fluid stream.

Dielectrophoresis or traveling-wave dielectrophoresis can also be used to separate other cell types, such as but not limited to cancer cells, from fluid samples. Theoretical calculations and simulation of dielectrophoresis spectra based on dielectric property parameters of different cells types, such as, for example, particular cancer cells, red blood cells, white blood cells, and nucleated red blood cells, can be used to calculate the effective, complex dielectric permittivities. Dielectric property parameters can be determined empirically or values for particular cell types can be taken from the literature (see, for example, Yang et al. (1999) Biophys. J. 76:3307–3314; Huang et al (1999) Biochim Biophys Acta 1417: 51–62; De Gasperis et al (1998) Meas. Sci. Technol. 9: 518–529; Huang et al. (1996) Biochim. Biophys Acta 1282:76–84; Becker et al. (1995) Proc. Natl. Acad.Sci USA 29: 860–864; Huang et al. (1999) J. Hematotherapy and Stem Cell Research 8: 481–490). Dielectrophoresis migration experiments on particular cell types can also be performed to observe their behavior on a dielectrophoresis chip as a function of field frequency. Based on determination of the frequency dependence of the dielectrophoretic responses of the two or more types of cells to be separated (for example, normal cells and cancer cells that are present in a sample), the frequency at which maximum difference between DEP behaviors between cell types can be determined and used as the frequency for cell separation.

Figure 20:
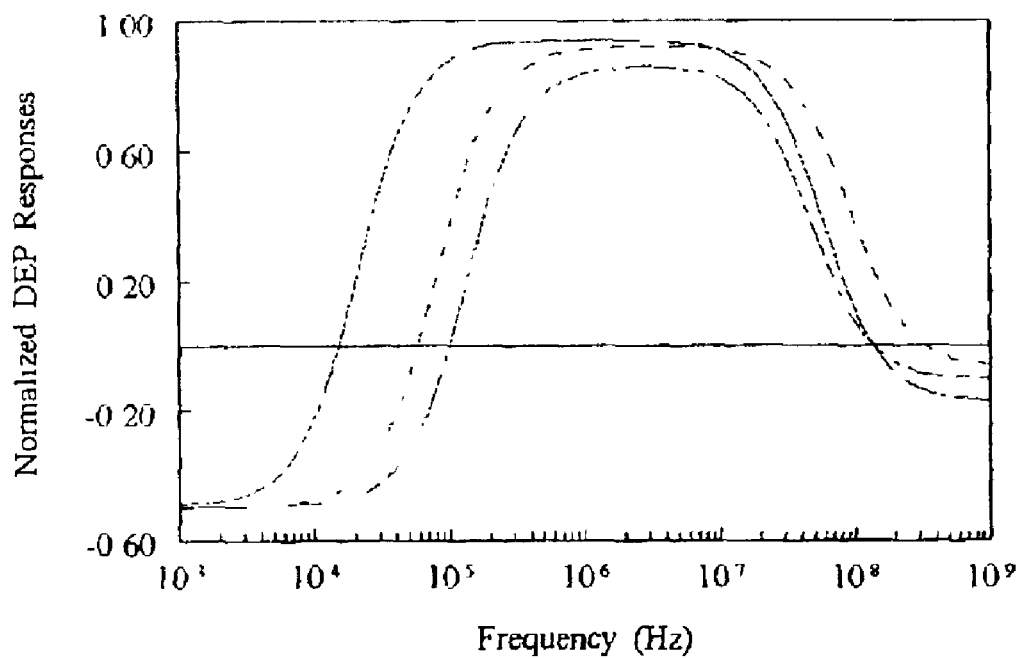
FIG. 20 is a graph illustrating the theoretical comparison between the DEP spectra for MDA231 cancer cells (solid line) T-lymphocytes (dashed line) and erythrocytes (small dashes) when the cells are suspended in a medium of electrical conductivity of 10 mS/m.
Figure 21A:
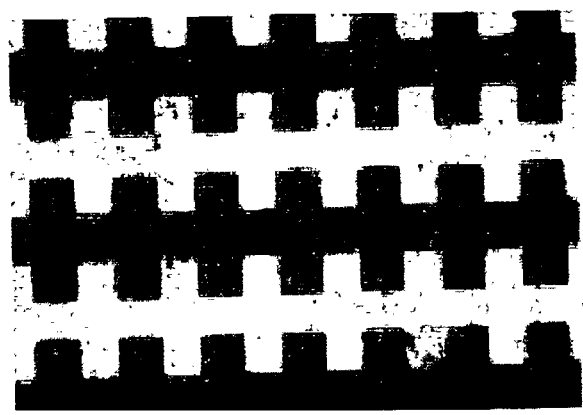
FIG. 21 depicts breast cancer cells from a spiked blood sample retained on electrodes of a dielectrophoresis chip.
Figure 21B:
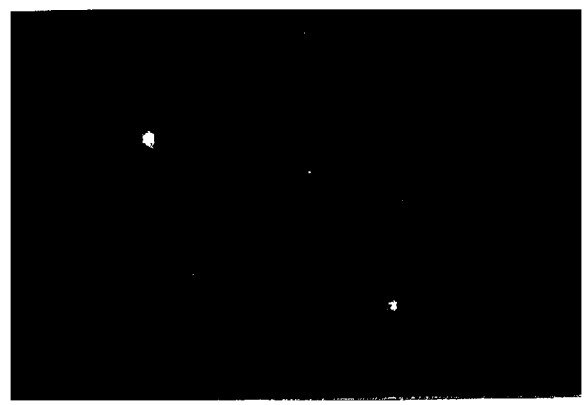

FIG. 20 shows the theoretical DEP spectra of MDA231 cancer cells, T-lymphocytes, and erythrocytes, when the cells are suspended in a medium of electrical conductivity of 10 mS/m. This information can be used to determine the optimal conditions for their separation. FIG. 21B, for example, is an image of fluorescently labeled breast cancer cells that were spiked into a blood sample and then separated by dielectrophoretic retention on a dielectrophoresis chip (shown in FIG. 21A) after microfiltration of the blood sample.

A method for enriching rare cells of the present invention that comprises at least one filtration step using a microfabricated filter of the present invention and separation of desirable sample components (such as enriched cells) can also include other steps, such as, but not limited to: selectively removing undesirable components from said fluid sample, additional filtration steps, one or more debulking steps, such as, for example, gradient centrifugation, selective sedimentation of one or more sample components, or selective lysis of one or more sample components.

Where the fluid sample is a blood sample, selectively removing undesirable components from a blood sample can comprises separating white blood cells from a blood sample, as described in a prior section. Where the fluid sample is a blood sample, debulking can comprises gradient centrifugation of the blood sample, selective sedimentation of red blood cells, or selective lysis of red blood cells. The rare cells whose enrichment is desired can be, as nonlimiting examples, fetal red blood cells, stem cells, or cancer cells.

In a particularly preferred embodiment, a blood sample can be processed to enrich rare cells such as fetal red blood cells or cancer cells. The blood sample can be debulked and red blood cells can be removed by gradient centrifugation, selective sedimentation of RBCs, or selective lysis of RBCs. The blood sample can then be dispensed into a filtration chamber that comprises at least one microfabricated filter of the present invention that comprises slots having dimension that allow RBCs to pass through the filter. Magnetic beads that are coated with one or more specific binding members that specifically bind white blood cells are then added to the sample components that are retained in the filtration chamber. The sample and beads are mixed and incubated, and then transferred to a separation column that engages a permanent magnet that extends along the length of the column. The beads adhere to the column wall, while the unbound portion of the sample is allowed to flow through. The unbound portion of the sample can then enter or be dispensed into a second filtration chamber that comprises at least one microfabricated filter of the present invention that comprises slots having dimension that allow RBCs to pass through the filter. Fluid flow through the chamber removes additional residual red blood cells and further reduces sample volume.

Magnetic beads that comprise one or more specific binding members that specifically bind the rare cells to be enriched are added to and mixed with the sample. The sample is then transferred or transported to a chamber that comprises a chip having electromagnetic units, where rare cells of interest are captured. After washing unbound cells and sample components from the chamber, the rare cells can be collected after turning off the electromagnetic units. In an alternative to magnetic separation, rare cells may be separated from other sample components dielectrophoretically on a dielectrophoresis chip.

III. Solutions for Sedimenting Red Blood Cells

The present invention includes solutions for sedimenting red blood cells of a blood sample. Red blood cell sedimenting solutions of the present invention comprise a chemical agent that induces red blood cell aggregation and at least one specific binding member that selectively binds red blood cells. When added to a blood sample, a solution for sedimenting red blood cells (an "RBC sedimenting solution") causes red blood cells to agglutinate and sediment, and preferably does not result in the agglutination or sedimentation of substantial numbers of rare cells of interest that may be present in a blood sample. Preferably, an RBC sedimenting solution of the present invention induces the agglutination and sedimentation of red blood cells while allowing at least 10% of rare cells whose enrichment is desired to remain in the supernatant. More preferably, an RBC sedimenting solution of the present invention induces the agglutination and sedimentation of red blood cells while allowing at least 20% of rare cells whose enrichment is desired to remain in the supernatant, and more preferably yet, an RBC sedimenting solution of the present invention allows at least 40% of rare cells whose enrichment is desired to remain in the supernatant. In the most preferred embodiments of the present invention, greater than 50% of rare cells whose enrichment is desired can be recovered from the supernatant after sedimenting RBCs with an RBC sedimenting solution of the present invention.

RBC Aggregation Inducing Agent

Certain chemical agents can induce red blood cell (RBC) aggregation and sedimentation. For example, dextran, hespan, pentaspan, ficoll, gum ararbic, poyvinylpyrrolidone, other natural or synthetic polymers, nucleic acids, and even some proteins can be used to induce aggregation of red blood cells (see, for example, U.S. Pat. No. 5,482,829, herein incorporated by reference). The optimal molecular weight and concentration of a chemical agent RBC aggregation inducer for aggregating red blood cells can be determined empirically.

A preferred chemical RBC aggregation inducing agent for use in a sedimenting solution of the present invention is a polymer such as dextran. Preferably the molecular weight of dextran in a red blood cell sedimenting solution of the present invention is between about 50 and about 2000 kilodaltons more preferably between about 65 and about 500 kilodaltons. Some preferred embodiments of the present invention are solutions comprising dextran having a molecular weight of between 110 and 114 kilodaltons. Preferably, the concentration of dextran in a red blood cell sedimenting solution of the present invention is between about 0.1% and about 20%, more preferably between about 0.2% and about 10%, and more preferably yet between about 1% and about 6%. Some examples include 5% Dextran (MW: 68 k) with 1% BSA and 2 microgram/ml Glycophorin-A antibody, or 1.4% Dextran (MW: 500 k) with 0.64 M oxalate. Example 10 of the present application summarizes the use of various dextran solutions for inducing RBC aggregation and precipitation.

Specific Binding Member that Binds RBCs

Specific binding members suitable for use in a red blood cell sedimenting solution of the present invention include, as nonlimiting examples, receptor ligands or molecules comprising receptor ligands, lectins, and antibodies that can agglutinate red blood cells. One or more specific binding members that can selectively bind RBCs can be used. By "selectively binds" is meant that a specific binding member used in an RBC sedimenting solution of the present invention to does not appreciably bind to rare cells of interest of the fluid sample. By "does not appreciably bind" is meant that not more than 30%, preferably not more than 20%, more preferably not more than 10%, and yet more preferably not more than 1.0% of one or more rare cells of interest are bound by the specific binding member that binds RBCs. In many cases, it is advantageous if a specific binding member that specifically binds red blood cells is multivalent, that it, that a single specific binding member molecule or complex can specifically bind to two or more red blood cells. Where molecules such as ligands are used as specific binding members, therefore, it can be advantageous to engineer a molecule with more that one, and preferably several, ligand moieties that can bind a receptor or other red blood cell surface-exposed molecule. The optimal concentration of such a molecule in a solution of the present invention can be tested empirically.

Antibodies, especially multivalent antibodies, such as but not limited to IgG and IgM antibodies, can be preferred for use in a sedimenting solution of the present invention. Antibodies that specifically bind red blood cells are preferably antibodies that recognize one or more cell surface epitopes on red blood cells and do not appreciably bind rare cells of interest that are present in the blood sample. Concentrations of antibodies used in a solution of the present invention can vary widely, depending at least in part on the avidity of the particular antibody, from less than 0.01 microgram per milliliter to up to one milligram per milliliter of sedimenting solution. Preferably, however, an antibody used in a solution of the present invention is present at a concentration of 200 micrograms per milliliter or less. The optimal concentration of antibody used can be dependent in part on the presence and concentration of other components of the solution, including but not limited to dextran and, optionally, other specific binding members, enhancers such as oxalate, etc. (see, for example, U.S. Pat. No. 5,482,829, herein incorporated by reference). One type of antibody that can be used in a sedimenting solution of the present invention is an antibody to glycophorin A. In one preferred embodiment of the present invention, a sedimenting solution comprises an IgM antibody to glycophorin A.

Lectins can also be used as specific binding members in a sedimenting solution of the present invention. Lectins can be tested for their ability to agglutinate and sediment red blood cells from a blood sample without sedimenting desirable rare cells, such that the desirable rare cells can be recovered from the sample supernatant after sedimentation. A wide variety of lectins from various plant sources can be tested for usefulness in a sedimenting solution of the present invention. As nonlimiting examples, ConA (Concanavalin A), DBA (Dolichos biforus agglutinin), DSL (Datura Stramonium lectin), EBL (Sambucus Nigra lectin), ECL (Erythrina Cristagalli lectin), GSLI (Griffonia Simplicifolia lectin I), GSLII (Griffonia Simplicifolia lectin II), jacalin (Artocarpus integrifolia agglutinin), LCA (Lens culinaris agglutinin), LEL (Lycopersicon esculentum lectin), MALII (Maackia amurensis lectin II), PHA (phaseolus vulgaris agglutinin), PHA-L (phaseolus vulgaris agglutinin leucoagglutinin), PHA-E (phaseolus vulgaris agglutinin erythroagglutinin), PNA (peanut agglutinin), PSA (Pisum Sativum Agglutinin), RCAI (Ricinus Communis Agglutinin I), SBA (Soybean Agglutinin), SJA (Sophora Japonica Agglutinin), STL (Solanum Tuberosum lectin), sWGA (Succinylated wheat germ agglutinin), URAI (Ulex europaeous agglutinin I), or WGA (wheat germ agglutinin) can be used in a sedimenting solution of the present invention.

The degree of RBC aggregation in lectin solutions varies, depending on lectin concentrations, lectin types and buffer solutions used. In most cases, the concentration of lectins used in the methods of the present invention will range from about one to about one hundred micrograms per milliliter. The efficacy of various lectins in agglutinating red blood cells and promoting their sedimentation can also be tested empirically. While some lectins (e.g., 10–50 $\mu$g/ml PHA-E in PBS, phosphate buffered saline) work well in achieving RBC aggregation and settlement, other lectins (e.g., 10–100 $\mu$g/ml ConA in PBS) may result in little aggregation. Example 8 summarizes the results of RBC aggregation with a number of lectin solutions.

It is within the scope of the present invention to include more than one specific binding member in a sedimenting solution of the present invention. For example, a sedimenting solution of the present invention can include two or more antibodies, each of which binds a different cell surface epitope, two or more lectins, or two or more ligands (or ligand-comprising molecules). It is also possible to have any combination of specific binding members. For example, a sedimenting solution can include one or more antibodies and one or more lectins, or one or more lectins and one or more ligands, etc.

Sedimenting solutions can be made and tested for their ability to sediment red blood cells and allow rare cells of interest to be recovered from the supernatant by adding the solutions to blood cells, mixing the blood sample and sedimenting solution, and incubating the blood sample for a period of time, after which the supernatant (unsedimented portion) is examined for the presence and amount of red blood cells. The volume of sedimenting solution added to the blood sample and the time of incubation can be varied in the testing of a potential sedimenting solution. For example, in Example 8, sedimenting solution is added to blood sample at a 1:1 ratio, and the incubation (settling time) is thirty minutes. Because the present invention seeks to increase the efficiency of enriching rare cells of a blood sample, incubation times of less than an hour are preferred. Preferably, a red blood cell sedimenting solution of the present invention removes at least 90% of the red blood cells of a sample, more preferably, at least 95% of the red blood cells of a sample, and more preferably yet, at least 99% of the red blood cells of a sample after a mixing period of 30 minutes followed by a settling time of 30 minutes.

A red blood cell sedimenting solution of the present invention can also include other components, such as, but not limited to, salts, buffering agents, agents for maintaining a particular osmolality, chelators, proteins, lipids, small molecules, anticoagulants, etc. For example, in some preferred aspects of the present invention, a red blood cell sedimenting solution comprises physiological salt solutions, such as PBS, PBS lacking calcium and magnesium or Hank's balanced salt solution. In some preferred aspects of the present invention, EDTA or heparin are present to red blood cell prevent clotting.

Combined Solution for Sedimenting Red Blood Cells and Selectively Removing Undesirable Sample Components of a Blood Sample In preferred embodiments of the present invention, a solution that sediments red blood cells can also include one or more additional specific binding members that can be used to selectively remove undesirable sample components other than red blood cells from the blood sample. In this regard, the present invention includes a combined sedimenting solution for enriching rare cells of a blood sample that sediments red blood cells and provides reagents for the removal of other undesirable components of the sample. Thus a combined solution for processing a blood sample comprises: dextran; at least one specific binding member that can induce agglutination of red blood cells; and at least one additional specific binding member that can specifically bind undesirable components of the sample other than RBCs.

Specific Binding Member for Removing Undesirable Components

In addition to the components of a sedimenting solution of the present invention, a combined solution of the present invention can comprise at least one specific binding member that can selectively bind undesirable components of a blood sample other than RBCs. One or more specific binding members that can selectively bind non-RBC undesirable components of a blood sample can be used to remove the undesirable components of the sample, increasing the relative proportion of rare cells in the sample, and thus contribute to the enrichment of rare cells of the sample. By "selectively binds" is meant that a specific binding member used in the methods of the present invention to remove one or more undesirable sample components does not appreciably bind to rare cells of interest of the fluid sample. By "does not appreciably bind" is meant that not more than 30%, preferably not more than 20%, more preferably not more than 10%, and yet more preferably not more than 1.0% of one or more rare cells of interest are bound by the specific binding member used to remove non-RBC undesirable components from the fluid sample. In many cases, the undesirable components of a blood sample will be white blood cells. In preferred embodiments of the present invention, a combined solution of the present invention can be used for sedimenting red blood cells and selectively removing white blood cells from a blood sample.

A specific binding member that can specifically bind white blood cells can be as nonlimiting examples, an antibody, a ligand for a receptor, transporter, channel or other moiety of the surface of a white blood cell, or a lectin or other protein that can specifically bind particular carbohydrate moieties on the surface of a white blood cell (for example, a selectin).

Preferably, a specific binding member that selectively binds white blood cells is an antibody that binds white blood cells but does not appreciably bind fetal nucleated red blood cells, such as, for example, an antibody to CD3, CD11b, CD14, CD17, CD31, CD45, CD50, CD53, CD63, CD69, CD81, CD84, CD102, or CD166. Antibodies can be purchased commercially from suppliers such as, for example Dako, BD Pharningen, Antigenix America, Neomarkers, Leinco Technologies, Research & Diagnostic Systems, Serotec, United States Biological, Bender Medsystems Diagnostics, Ancell, Leinco Technologies, Cortex Biochem, CalTag, Biodesign, Biomeda, Accurate Chemicals & Scientific and Chemicon International. Antibodies can be tested for their ability to bind an efficiently remove white blood cells and allow for the enrichment of rare cells of interest from a sample using capture assays well known in the art.

Specific binding members that selectively bind to one or more undesirable components of the present invention can be used to capture one or more non-RBC undesirable components, such that one or more desirable components of the fluid sample can be removed from the area or vessel where the undesirable components are bound. In this way, the undesirable components can be separated from other components of the sample that include the rare cells to be separated. The capture can be effected by attaching the specific binding members that recognize the undesirable component or components to a solid support, or by binding secondary specific binding members that recognize the specific binding members that bind the undesirable component or components, to a solid support, such that the undesirable components become attached to the solid support. In preferred embodiments of the present invention, specific binding members that selectively bind undesirable sample components provided in a combined solution of the present invention are coupled to a solid support, such as microparticles, but this is not a requirement of the present invention.

Magnetic beads are preferred solid supports for use in the methods of the present invention to which specific binding members that selectively bind undesirable sample components can be coupled. Magnetic beads are known in the art, and are available commercially. Methods of coupling molecules, including proteins such as antibodies and lectins, to microparticles such as magnetic beads are known in the art. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are preferably provided in a combined solution of the present invention coated with a primary specific binding member, such as an antibody that can bind a cell that is to be removed from the sample, or a secondary specific binding member, such as sreptavidin, that can bind primary specific binding members that bind undesirable sample components (such as biotinylated primary specific binding members).

In preferred embodiments of the present invention, the fluid sample is a maternal blood sample, the rare cells whose separation is desirable are fetal cells, and the undesirable components of the sample to be removed from the sample are white blood cells. In these embodiments, a specific binding member that selectively binds white blood cells is used to remove the white blood cells from the sample by magnetic capture. Preferably, the specific binding member provided is attached to magnetic beads for direct capture, or, is provided in biotinylated form for indirect capture of white blood cells by streptavidin-coated magnetic beads.

A combined solution for enriching rare cells of a blood sample of the present invention can also include other components, such as, but not limited to, salts, buffering agents, agents for maintaining a particular osmolality, chelators, proteins, lipids, small molecules, anticoagulants, etc. For example, in some preferred aspects of the present invention, a combined solution comprises physiological salt solutions, such as PBS, PBS lacking calcium and magnesium or Hank's balanced salt solution. In some preferred aspects pf the present invention, EDTA or heparin are present to red blood cell prevent clotting.

IV. Method of Enriching Rare Cells of a Blood Sample Using a Solution that Selectively Sediments Red Blood Cells The present invention also includes a method of enriching rare cells of a blood sample using a solution that selectively sediments red blood cells. The method includes: adding a red blood cell sedimenting solution of the present invention to a blood sample, mixing the blood sample and the red blood cell sedimenting solution, allowing red blood cells to sediment from the sample, and removing a supernatant that comprises enriched rare cells.

Blood Sample

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. In some cases, it can be preferably to use a washed blood sample, in which blood cells have been pelleted and resuspended in a blood-compatible buffer (for example, PBE) at least once. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

Addition of Sedimenting Solution to Sample

A red blood cell sedimenting solution can be added to a blood sample by any convenient means, such as pipeting, automatic liquid uptake/dispensing devices or systems, pumping through conduits, etc. In most cases, the blood sample will be in a tube that provides for optimal separation of sedimented cells, but it can be in any type of vessel for holding a liquid sample, such as a plate, dish, well, or chamber. The amount of sedimenting solution that is added to a blood sample can vary, and will largely be determined by the concentration of dextran and specific binding members in the sedimenting solution (as well as other components), so that their concentrations will be optimal when mixed with the blood sample. Optimally, the volume of a blood sample is assessed, and an appropriate proportional volume of sedimenting solution, ranging from 0.01 to 100 times the sample volume, preferably ranging from 0.1 times to 10 times the sample volume, and more preferably from 0.25 to 5 times the sample volume, and even more preferably from 0.5 times to 2 times the sample volume, is added to the blood sample. (It is also possible to add a blood sample, or a portion thereof, to a red blood cell sedimenting solution. In this case, a known volume of sedimenting solution can be provided in a tube or other vessel, and a measured volume of a blood sample can be added to the sedimenting solution.)

Mixing

The blood sample and red blood cell sedimenting solution are mixed so that the chemical RBC aggregating agent (such as a polymer, such as, for example, dextran) and one or more specific binding members of the sedimenting solution, as well as the components of the blood sample are distributed throughout the sample vessel. Mixing can be achieved means such as electrically powered acoustic mixing, stirring, rocking, inversion, agitation, etc., with methods such as rocking and inversion, that are least likely to disrupt cells, being favored.

Incubation of Blood Sample and Sedimenting Solution

The sample mixed with sedimenting solution is allowed to incubate to allow red blood cells to sediment. Preferably the vessel comprising the sample is stationary during the sedimentation period so that the cells can settle efficiently. Sedimentation can be performed at any temperature from about 5 degrees C. to about 37 degrees C. In most cases, it is convenient to perform the steps of the method from about 15 degrees C. to about 27 degrees C. The optimal time for the sedimentation incubation can be determined empirically for a given sedimenting solution, while varying such parameters as the concentration of dextran and specific binding members in the solution, the dilution factor of the blood sample after adding the sedimenting solution, and the temperature of incubation. Preferably, the sedimentation incubation is from five minutes to twenty four hours in length, more preferably from ten minutes to four hours in length, and most preferably from about fifteen minutes to about one hour in length. In some preferred aspects of the present invention, the incubation period is about thirty minutes.

Collecting Enriched Cells

Removing a supernatant (or a portion thereof) from the sample after the red blood cells have sedimented can be performed by pouring, pipetting, pumping, or a fluid uptake device. The supernatant comprises enriched rare cells of the blood sample, such as, but not limited to, stem cells, fetal cells, nucleated red blood cells, subpopulations of blood cells (e.g. T cells), non-hematopoietic cells (e.g. epithelial cells) cancer cells, virus-infected cells, parasite-infected cells, parasitic cells, or bacterial cells. Following RBC sedimentation with a RBC sedimenting solution of the present invention, the proportion of the rare cells to the other cell types in the sample has increased, thus resulting in enriched rare cells.

Method of Enriching Rare Cells of a Blood Sample Using a Combined Sedimenting Solution The present invention also includes a method of enriching rare cells of a blood sample using a combined solution for enriching rare cells of a blood sample. The method comprises: adding a combined solution for enriching rare cells of the present invention to a blood sample in a tube or vessel; mixing the blood sample and combined solution of the present invention; allowing red blood cells to sediment from the blood sample; allowing undesirable components to bind a solid support; and removing a supernatant from said blood sample that comprises enriched rare cells.

Blood Sample

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. In some cases, it can be preferably to use a washed blood sample, in which blood cells have been pelleted and resuspended in a blood-compatible buffer (for example, PBE) at least once. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

Addition of Sedimenting Solution to Sample

A combined sedimenting solution can be added to a blood sample by any convenient means, such as pipeting, automatic liquid uptake/dispensing devices or systems, pumping through conduits, etc. In most cases, the blood sample will be in a tube that provides for optimal separation of sedimented cells, but it can be in any type of vessel for holding a liquid sample, such as a plate, dish, well, or chamber. The amount of combined sedimenting solution that is added to a blood sample can vary, and will largely be determined by the concentration of dextran and specific binding members in the combined solution (as well as other components), so that their concentrations will be optimal when mixed with the blood sample. Optimally, the volume of a blood sample is assessed, and an appropriate proportional volume of combined solution, preferably ranging from 0.1 times to 10 times the sample volume, and more preferably from 0.25 to 5 times the sample volume, and even more preferably from 0.5 times to 2 times the sample volume, is added to the blood sample. (It is also possible to add a blood sample, or a portion thereof, to a combined solution. In this case, a known volume of combined solution can be provided in a tube or other vessel, and a measured volume of a blood sample can be added to the combined solution.)

Mixing

The blood sample and combined sedimenting solution are mixed so that the dextran and specific binding members of the combined solution, as well as the components of the blood sample, are distributed throughout the sample vessel, and specific binding members can bind to sample components. Mixing can be achieved means such as electrically powered acoustic mixing, stirring, rocking, inversion, agitation, etc., with methods such as rocking and inversion, that are least likely to disrupt cells, being favored.

Incubation of Blood Sample and Combined Solution

The sample mixed with combined sedimenting solution is allowed to incubate to allow red blood cells to sediment. Preferably the vessel comprising the sample is stationary during the sedimentation period so that the red blood cells can settle efficiently. Sedimentation can be performed at any temperature from about 5 degrees C. to about 37 degrees C.

In most cases, it is convenient to perform the steps of the method from about 15 degrees C. to about 27 degrees C. The optimal time for the sedimentation incubation can be determined empirically for a given combined sedimenting solution, while varying such parameters as the concentration of dextran and specific binding members in the solution, the dilution factor of the blood sample after adding the combined solution, and the temperature of incubation. Preferably, the sedimentation incubation is from ten minutes to twenty four hours in length, more preferably from fifteen minutes to one hour in length. In some preferred aspects of the present invention, the incubation period is about thirty minutes.

Allowing Undesirable Sample Components or Rare Cells Bound by Specific Binding Members to Bind a Solid Support Allowing undesirable components or rare cells bound by specific binding members to bind a solid support can be performed in any of several ways, depending on the nature of the specific binding member that binds undesirable sample components, the type of solid support, and the overall format of the enrichments procedure (whether it is performed in one or more vessels, whether fluid flow is involved, etc.). In some embodiments, after the sedimentation step, the supernatant can be passed through or over a solid support that comprises secondary specific binding members that can bind the primary specific binding members (for example, streptavidin, if the primary specific binding member is biotinylated). For example, the supernatant can be pipetted or pumped through a column or over a membrane that can capture the undesirable components or rare cells bound by specific binding members. In other embodiments, one or more specific binding members that can bind undesirable sample components or rare cells can be bound to a solid support, such as beads, that can be sedimented along with the red blood cells, with or without a centrifugation step.

In preferred embodiments of the present invention, magnetic beads are solid supports, and one or more specific binding members that bind undesirable sample components are bound to magnetic beads in a combined sedimenting solution of the present invention. The magnetic beads can be captured using a magnet before, during or after the sedimentation step. In preferred aspects of the present invention, during the sedimentation step magnetic beads comprising primary or secondary specific binding members for the capture of undesirable components or rare cells of the blood sample are collected by placing the vessel that contains the sample next to a magnet. Magnetic capture can also be performed when the combined solution comprises a specific binding member that can specifically bind undesirable components or rare cells or interest can be bound by magnetic beads that are coated with, for example, streptavidin (where the specific binding member is biotinylated).

Preferably, magnetic capture uses one or more permanent magnets, such as permanent magnets positioned within or alongside a tube, dish, or vessel that contains the target cell-magnetic bead complexes, and occurs during the sedimentation step. Commercially available magnetic separators that include permanent magnets (such as those sold by Immunicon (Huntington Valley, Pa.)) can also be used, however, or magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations".

In preferred embodiments, combined solution of the present invention comprises at least one specific binding member that selectively binds white blood cells as undesirable components of the sample. The specific binding member is bound to, or is able to bind to, magnetic beads. The tube containing the sample mixed with the combined solution is positioned next to a magnet during sedimentation of red blood cells, and white blood cells are collected at the wall of the tube as red blood cells settle to the bottom of the tube. The supernatant comprises enriched rare cells.

Collecting Enriched Rare Cells

The process of collecting enriched cells will vary depending on whether a combined sedimenting solution comprises a specific binding member that selectively binds undesirable sample components or a specific binding member that selectively binds rare cells of interest. In embodiments in which a combined sedimenting solution comprises a specific binding member that selectively binds undesirable sample components, removing a supernatant (or a portion thereof) from the sample after the red blood cells have sedimented and undesirable sample components have been separated can be performed by pouring, pipeting, pumping, or a fluid uptake device. The supernatant comprises enriched rare cells of the blood sample, such as, but not limited to, stem cells, fetal cells, nucleated red blood cells, cancer cells, virus-infected cells, parasite-infected cells, parasitic cells, or bacterial cells. The proportion of these cells relative to the total cell population in the collected supernatant has increased over their proportion of the total cell population in the pre-sedimented blood sample.

Further Enrichment Steps

The use of sedimenting solutions of the present invention, including combined solutions for enriching rare cells of a blood sample, can be combined with other processing steps such as debulking, or separation steps. Debulking steps that can be combined with the use of a combined solution include. As nonlimiting examples, selective lysis, filtration, and centrifugation steps. Additional separation steps that can be used include separations that include capture of sample components to solid supports using specific binding members, and separations performed on active chips, such as dielectrophoretic and traveling wave dielectrophoretic separations, and separations using electromagnetic capture on an electromagnetic chip.

The present invention also includes methods of enriching rare cells from a blood sample in which selective sedimentation of RBCs is combined with filtration, such as filtration through a microfabricated filter of the present invention.

A method for enriching rare cells of the present invention that comprises a RBC sedimentation step and at least one filtration step using a microfabricated filter of the present invention can also include other steps, such as, but not limited to: selectively removing further undesirable components from said fluid sample, separating rare cells of the sample, additional filtration steps, or additional debulking steps, such as, for example, selective lysis of one or more sample components.

In a particularly preferred embodiment, a blood sample can be processed to enrich rare cells such as fetal red blood cells or cancer cells. Red blood cells can be removed by selective sedimentation of RBCs using a solution of the present invention. White blood cells can be removed by adding magnetic beads that are coated with one or more specific binding members that specifically bind white blood cells to the post-sedimentation supernatant, or, preferably, a combined solution of the present invention is used to sediment red blood cells and remove white blood cells using magnetic capture. The blood sample can then be dispensed into a filtration chamber that comprises at least one microfabricated filter of the present invention that comprises slots having dimension that allow RBCs to pass through the filter. Fluid flow through the chamber removes additional residual red blood cells and further reduces sample volume, resulting in a sample having enriched rare cells. Depending on the source of the sample, the enriched rare cells can be stem cells, fetal cells, cancer cells, subtypes of white blood cells, bacterial cells, parasite cells, or bacteria-, parasite-, or virus-infected cells.

Additional Debulking Steps

As used herein, "debulking" refers to a step in the processing of a sample in which the volume of the sample is significantly reduced by at least fifty per cent or greater than 50% of the cellular components of a sample are removed. For example, in preferred aspects of the present invention in which the fluid sample is a blood sample, a majority of the non-nucleated red blood cells (RBCs) that make up more than 90% of the cellular components of a blood sample are removed during a debulking step.

Additional debulking steps used before or after sedimenting red blood cells with a solution of the present invention can be, as nonlimiting examples, an additional sedimentation step, a concentration step, a centrifugation step, or a filtration step. Centrifugation and filtration are preferred debulking steps that reduce the volume of a fluid sample and at the same time allow the technician to select fractions of the centrifuged or filtered product that retain desirable components and do not retain at least a portion of some undesirable components.

Filtration using a microfabricated filter of the present invention has been disclosed earlier in the application. Other types of filtration steps can also be used. These include, as nonlimiting examples, filtration using columns packed with various resins or polymeric materials, filtration using membranes of pore sizes that allow retention of desirable components, filtration using channels that are microetched into one or more chips, by using "bricks" or dams that are built onto the surface of a chip, or by using slots or pores that are microetched into a solid surface that can be within a chamber or form a wall of a chamber as disclosed earlier in the application (see, for example, U.S. Pat. No. 5,837,115 issued Nov. 17, 1998 to Austin et al., herein incorporated by reference in its entirety and U.S. Pat. No. 5,726,026 issued Mar. 10, 1998 to Wilding et al., herein incorporated by reference in its entirety).

Another method for debulking blood sample is the use of hypotonic solutions to exploit the differential responses of maternal red blood cells (and reticulocytes) and white blood cells (and nucleated red blood cells). By treating blood samples with hypotonic solutions, red blood cells can be lysed, or red blood cells can be altered significantly so that they become readily separable from white blood cells and other nucleated cells. Alternatively, certain biochemical reagents may be used to selectively lyse red blood cells.

More than one debulking step can be employed in the methods of the present invention. For example, in some applications, undesirable components of the sample can be removed in steps subsequent to a first debulking step. It can then practical and advantageous to further reduce the volume of the remaining sample. This can be done through any of the described debulking methods, using scaled down volumes and areas where appropriate.

Separation Steps

The methods of the present invention can include sedimentation or red blood cells from a blood sample in combination with one or more separation steps. In general, a separation step will selectively remove one or more undesirable components from a sample, or selectively separate one or more desirable components of a sample. These steps will depend on the properties of the particular cells to be removed or separated from the sample, such as their binding properties, physical properties such as size or density, and electrical properties.

Sedimenting RBCs Plus Selectively Removing Undesirable Components

The present invention includes methods in which the selective removal of one or more non-RBC undesirable components of a fluid sample is performed simultaneously with sedimenting red blood cells of a sample. However, in some methods of the present invention, in which a sedimenting solution does not comprise a specific binding member that selectively binds non-RBC undesirable components, removal of one or more undesirable components of a fluid sample can be performed before or after sedimenting red blood cells from the blood sample. It is also possible to remove more than one type of undesirable component from a blood sample, and to perform the separations in separate steps.

Preferably, in the methods of the present invention, selective removal of one or more undesirable components of a fluid sample makes use of specific recognition of one or more undesirable components by one or more specific binding members. The use of specific binding members in removing undesirable components of a sample has been disclosed in earlier sections of the application and also apply here. The specific binding member used in the methods of the present invention can be any type of molecule or substrate that can specifically bind one or more undesirable components. Receptor ligands (either naturally occurring, modified, or synthetic), antibodies, and lectins are nonlimiting examples of specific binding members that can be used in the methods of the present invention. More than one different specific binding member can be used to capture one or more undesirable components to a solid support. Preferably, a specific binding member used in the methods of the present invention to selectively remove one or more undesirable components does not appreciably bind to desirable components of the fluid sample. In most applications of the present invention, a specific binding member used in the methods of the present invention to remove one or more undesirable components does not appreciably bind to the rare cells of the fluid sample that are to be separated. By "does not appreciably bind" is meant that not more than 30%, preferably not more than 20%, more preferably not more than 10%, and yet more preferably not more than 1.0% of the rare cell of the fluid sample that are to be enriched using the methods of the present invention are bound by the specific binding member used to selectively remove undesirable components of the fluid sample. Preferred specific binding members used in the methods of the present invention include antibodies, particularly antibodies that recognize and bind cell surface epitopes.

The capture can be effected by attaching antibodies that recognize the undesirable component or components to a solid support, or by binding secondary specific binding members that recognize the antibodies that bind the undesirable component or components, to a solid support, such that the undesirable components become attached to the solid support and become fixed at a particular location. A solid support can be, as nonlimiting examples, a surface, such as a plastic or polymeric surface, a gel or polymer, a membrane, the surface of a chip, or a bead. In the present invention, magnetic beads are preferred solid supports for the capture and selective removal of undesirable components of a sample.

The capture of undesirable components of a sample can be direct or indirect. For direct capture, a first specific binding member that binds to one or more undesirable components of a sample can be attached to a solid support. The one or more undesirable components, when contacted with the solid support, then bind to the solid support. For indirect capture, a primary specific binding member that binds to one or more undesirable components of a sample can be contacted with the one or more undesirable components, and a secondary specific binding member that can bind the primary specific binding member can be attached to a solid support. When the undesirable components that have bound the primary specific binding member are contacted with the solid support, the one or more undesirable components of the sample can bind the solid support via the primary and secondary specific binding members. In certain preferred embodiments of the present invention where selective removal of one or more undesirable components of a sample is performed, direct capture is preferred, as direct capture comprises fewer steps.

In preferred embodiments of the present invention, the fluid sample is a maternal blood sample, the rare cells whose separation is desirable are fetal cells, and the undesirable components of the sample to be removed from the sample are white blood cells. In these embodiments, a specific binding member that selectively binds white blood cells is used to remove the white blood cells from the sample by magnetic capture. Preferably, the specific binding member is either used to coat magnetic beads for direct capture, or is used in biotinylated form for indirect capture of white blood cells by streptavidin-coated magnetic beads.

A blood sample from which red blood cells have been sedimented can be incubated with one or more specific binding members, such as, but not limited to, antibodies, that specifically recognize one or more undesirable components of a fluid sample. Mixing and incubation of one or more specific binding members with the sample can be performed in a tube, dish, vessel, or chamber. The one or more undesirable components can be captured, either directly or indirectly, via their binding to the specific binding member. For example, a specific binding member can be bound to a solid support, such as a bead, membrane, or column matrix, and following incubation of the fluid sample with the specific binding member, the fluid sample, containing unbound components, can be removed from the solid support. Alternatively, one or more primary specific binding members can be incubated with the fluid sample, and the fluid sample can be contacted with a secondary specific binding member that can bind or is bound to a solid support. In this way the one or more undesirable components of the sample can become bound to a solid support, enabling separation of the undesirable components from the fluid sample.

In one preferred embodiment, after incubation of magnetic beads that comprise a specific binding member that specifically bind undesirable components with a sample, the sample is transported through a separation column that comprises or engages at least one magnet. As the sample flows through the column, undesirable components that are bound to the magnetic beads adhere to one or more walls of the tube adjacent to the magnet or magnets. An alternative embodiment uses a magnetic separator, such as the magnetic separator manufactured by Immunicon. Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". In yet another preferred embodiment, a tube that contains the sample and magnetic beads is positioned next to one or more magnets for the capture of undesirable components bound to magnetic beads. The supernatant, depleted of the one or more undesirable components, can be removed from the tube after the beads have collected at the tube wall.

Other manipulations that can be performed to remove undesirable components from a blood sample before or preferably after sedimenting red blood cells include passing the sample or sample supernatant over a solid support (which can be, as nonlimiting examples, a membrane or a matrix) that comprises attached specific binding members that capture the undesirable components. The blood sample or blood sample supernatant can be incubated with or passed through or over such a solid support to remove undesirable components, such as, but not limited to, white blood cells. Flow cytometry, dielectrophoretic separation, filtration, or other separation techniques can also optionally be employed to remove undesirable components from blood samples.

Sedimenting RBCs Plus Separating Desirable Components

The present invention also includes methods in which sedimenting rare cells is combined with the separation of one or more desirable components, such as rare cells whose enrichment is desired, from a fluid sample. Preferably, separation of rare cells from a fluid sample occurs after red blood cell sedimentation.

In some preferred embodiments of the present invention, separating rare cells uses at least one specific binding member that specifically binds the one or more rare cells and capture of the rare cells to a solid support. Receptor ligands (either of natural sources, modified, or synthetic), antibodies, and lectins are nonlimiting examples of specific binding members that can be used in the methods of the present invention. More than one different specific binding member can be used to capture one or more rare cells to a solid support.

A specific binding member can be any type of molecule or substrate that can selectively bind one or more rare cell types. Preferred specific binding members used in the methods of the present invention include antibodies, particularly antibodies that recognize and bind antigens on the surface of rare cells.

In a particularly preferred embodiment, the fluid sample is a blood sample and fetal nucleated red blood cells are the rare cells to be enriched. In this case, specific binding members such as lectins or antibodies can be used to bind and remove white blood cells.

Antibodies can also be used as specific binding members to capture fetal nucleated red blood cells from a blood sample. For example, a CD71 antibody can be used (see Example 11). An antibody or antibodies can also be used to enrich other rare cells such as, for example, cancer cells or stem cells from fluid samples such as urine or blood samples. Antibodies, lectins, or other specific binding members can be tested for their ability to bind an efficiently separate particular rare cell types from a sample using capture assays well known in the art.

A blood sample from which red blood cell have been sedimented can be incubated with one or more specific binding members, such as antibodies, that specifically recognize one or more rare cell types of a fluid sample. The one or more rare cell types can be captured, via their direct or indirect binding to the specific binding member, and the remainder of the fluid sample can be removed from the area, surface, or vessel where the rare cells being isolated are bound. For example, a specific binding member can be bound to a solid support, such as a membrane or column matrix, and following incubation of the fluid sample with the specific binding member, the fluid sample, containing unbound components, can be removed from the solid support. A solid support can be, as nonlimiting examples, a surface, such as a plastic surface, a gel or polymer, a membrane, the surface of a chip, or a bead. In the present invention, magnetic beads are preferred solid supports for the separation and capture of rare cells of a sample.

Capture of cells, viruses, molecules, and other moieties to solid supports is well known in the arts of cell biology, biochemistry, and antibody technology, and can use a variety of formats known in the art. The capture of rare cells of a sample can be direct or indirect. For direct capture, a first specific binding member that binds to one or more rare cells of a sample can be attached to a solid support. The rare cells, when contacted with the solid support, then bind to the solid support. For indirect capture, a primary specific binding member that binds to the desirable rare cells of a sample can be contacted with the one or more rare cells, and a secondary specific binding member that can bind the primary specific binding member can be attached to a solid support. When the rare cells that have bound the primary specific binding member are contacted with the solid support, the one or more rare cells of the sample can bind the solid support via the primary and secondary specific binding members.

In many cases it can be preferable to provide the specific binding member that binds the rare cells already bound to a solid support. For example, beads, such as magnetic beads, to which one or more specific binding members that bind the rare cells are attached can be added to the sample, or the sample can be passed over a solid support such as a membrane or the surface of a plate that comprises a specific binding member, or through a solid support such as a column matrix that comprises a specific binding member. Using specific binding members that are directly bound to a solid support can increase the efficiency of the enrichment procedure.

In preferred embodiments, separation of one or more rare cells of the sample using specific binding members to capture the rare cells to a solid support, and can be performed in a dish, well, tube, column, or other vessel. In some preferred embodiments, the solid support comprises magnetic beads.

Magnetic beads are preferred solid supports for use in the methods of the present invention. Magnetic beads are known in the art, and are available commercially. Magnetic beads can be purchased that are coated with secondary specific binding members, for example secondary antibodies or streptavidin. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are coated with either streptavidin, a secondary antibody, or a primary antibody that can bind a cell that is to separated from the sample. Where streptavidin coated beads are used, the primary specific binding member is preferably biotinylated (for example a biotinylated primary antibody) such that the streptavidin coated bead will bind a sample component that is bound to the biotinylated antibody through a streptavidin-biotin link. Methods of using magnetic beads in the capture of directly or indirectly bound cells are well known in the art, and are also described in the examples provided. The methods of capture can use permanent magnets, such as permanent magnets positioned within or alongside a tube, dish, or vessel that contains the target cell-magnetic bead complexes, or commercially available magnetic separators that include permanent magnets (Immunicon). Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations".

A discussion and references of the use of electromagnetic forces and their use is separations provided in a previous section of this application on methods of enriching rare cells involving filtration can also be applied to the separation of rare cells following RBC sedimentation.

Rare cells of the present invention can also be separated from a fluid sample using dielectrophoretic forces. The use of dielectrophoretic forces can be employed where the rare target cells have dielectrophoretic properties than are significantly different than other components that remain in the sample. That is, the difference in dielectrophoretic properties between rare target cells and nondesirable sample components must be sufficient to allow dielectrophoretic separation using micro-scale electrodes that can be built into or onto a chip. In most cases in which the fluid sample is a biological fluid sample, the other components of the sample whose dielectric properties must be taken into account are cells, such as cells that are not rare target cells. The feasibility of using dielectrophoresis for the separation of rare target cells can therefore depend on whether nondesirable components having similar dielectrophoretic properties as the target cells. Preferably, then, in applications of the method where a sample comprises a type of non-target cells that have similar dielectrophoretic properties as the target cells, selective removal of the type of non-target cells using methods other than dielectrophoresis has been performed prior to dielectrophoretic separation of target cells. Preferably in such instances, the selective removal of the non-target cells with similar dielectric properties using methods other than dielectrophoresis has been efficient, where efficiency refers to the percentage of non-target cells removed. The level of efficiency can vary with the application, but preferably the efficiency of selective removal of non-target cells with similar dielectric properties is greater than 30% of the non-target cells removed, more preferably greater than 50% of the non-target cells removed, and more preferably yet, greater than 90% of the non-target cells removed, and even more preferably, greater than 99% of the non-target cells removed in the selective removal step.

The previous discussion and references provided for the design and use of micro-electrodes to facilitate filtration by translocating sample components, such as nonfilterable cells, away from a filter using dielectrophoresis are also relevant to the use of micro-electrodes to facilitate dielectrophoretic separation of rare target cells. Various dielectrophoresis separation methods, such as those described in U.S. application Ser. No. 09/686,737, filed Oct. 10, 2000 entitled "Compositions and Methods for Separation of Moieties on Chips", incorporated by reference, and described in U.S. application Ser. No. 09/679,024, entitled "Apparatuses Containing Multiple Active Force Generating Elements and Uses Thereof" filed Oct. 4, 2000, also herein incorporated by reference in its entirety, may be employed for separating rare target cells.

In some applications of the present invention, separation of rare cells from a fluid sample may exploit the differences in cell physical properties. For example, as discussed above, dielectrophoresis may be used to separate nucleated red blood cells from maternal red blood cells (non-nucleated). By exploiting the differences in their dielectric properties, nucleated red blood cells and mature red blood cells (and reticulocytes) are caused to exhibit positive and negative (or small positive) dielectrophoresis forces, respectively, under certain cell suspension and electric field conditions. When the cell suspension is introduced to a chamber containing microelectrodes on the bottom surface, nucleated red blood cells can be collected and retained on the electrodes whilst the red blood cells are carried away from the chamber together with the fluid stream.

Other manipulations that can be performed to separate rare cells from a blood sample before or preferably after sedimenting red blood cells include passing the sample or sample supernatant over a solid support (which can be, as nonlimiting examples, a membrane or a matrix) that comprises attached specific binding members that capture the undesirable components. The blood sample or blood sample supernatant can be incubated with or passed through or over such a solid support to collect the rare cells.

V. Automated Systems for the Enrichment of Rare Cells of a Fluid Sample

The present invention also includes automated systems for the enrichment of rare cells of fluid samples. An automated system of the present invention uses automated steps to replicate steps of enrichment procedures described herein that can be performed in nonautomated fashion. The hardware performs the function of a nonautomated procedure, such as but not limited to, regulation of fluid flow, filtration, fluid transfer, and fluid level sensing. An automated system of the present invention comprises: at least one filtration chamber of the present invention; at least one power supply, signal source, or control circuit for the automated control and powering of fluid flow through the one or more filtration chambers; and means for collecting enriched cells of the fluid sample.

Filtration Chamber

The automated system comprises at least one filtration chamber. A filtration chamber is a chamber that can contain a volume of fluid and that comprises at least one microfabricated filter of the present invention that allows for the separation of components of a sample based on size, dimensions, or deformability of the components. A filtration chamber can comprise any suitable material, for example, silicon, glass, metal, ceramics, polymers, plastics, etc. and can be of a rigid or flexible material. Preferred materials for a chamber include materials that do not interfere with the manipulation of components of a sample, for example, insulating materials that do not bind charged or polarized molecules, such as certain plastics and polymers, for example, acrylic, or glass. The inner surfaces of the walls of a chamber can optionally be coated with biological or nonbiological materials, e.g., lipids, polymers, or compounds. A filtration chamber can be of any shape or size, and can accommodate a range of volumes, but preferably a filtration chamber of the present invention has a volumetric capacity of from 0.01 milliliter to 2 liters, more preferably from 0.1 milliliters to 0.5 liters, and most preferably from 0.2 milliliters to 80 milliliters.

In preferred embodiments of the present invention, the filtration chamber is a filtration chamber or the present invention that comprises at least one microfabricated filter. The filter is oriented perpendicular to the direction of fluid flow and preferably comprises two or more tapered pores. A pore allows fluid communication between the two sides of a filter. The one or more filters are optionally but preferably oriented with the narrower opening of the tapered pore facing the interior portion of the chamber where fluid flows toward filter, and the wider opening of the tapered pore facing the side of the filter where fluid flows out from the pores and away from the filter.

The pores in the filters for the present invention (e.g., as shown in FIG. 1, FIG. 2, and FIG. 3) can have various shapes. Preferably, they are elongated quadrilateral or ellipsoidal shapes, called slots. In preferred embodiments in which an automated system is used to enrich rare cells of a blood sample, the slots may have various sizes so that the length to width ratio is greater than 3. Preferably, the length-to-width ratio is greater than 5. In some applications, the length-to-width ratio can even be greater than 20. In using such filters for removing red blood cells, the large length-to-width ratio may result in a preferred fluid flow profile near the openings so that when the cells flow toward the filter openings, the red blood cells, because of their double-discoid shapes, may re-orientate themselves and preferably, move through the filter openings.

In preferred embodiments, a filtration chamber or the present invention comprises from one to four filters each having from 4 to 1,000,000 tapered slots, preferably from 100 to 250,000 tapered slots. The slots are of rectangular shape, with a length (horizontal dimension in FIG. 1) of from about one micron to about one thousand microns, preferably from about 10 microns to about 500 microns and more preferably from about 20 microns to about 250 microns and a width (vertical dimension in FIG. 1) from about 0.5 to about 20 microns, preferably from about one to about 10 microns, and more preferably from about 2 to 6 microns. Preferably, the variation in the size of the slots (length and width) is less than 20%, more preferably less than 10%, and most preferably less than 5%. Preferably, the slots can allow for the passage of mature red blood cells through the filter, while not allowing cells having a greater diameter (for example, white blood cells and nucleated red blood cells) to flow through the filter. Preferably, a slot is made during the machining of a chamber, and is formed by laser ablation, or microetched or bored into a surface that comprises glass, silicon, or hard plastic such as acrylic, polycarbonate, or polyimide.

A filtration chamber of the present invention can be designed such that one or more microfabricated filters is internal to the chamber, dividing the chamber into subchambers. Where a filtration chamber comprises a single internal microfabricated filter, for example, the filtration chamber can comprise a prefiltration "antechamber" and a "postfiltration subchamber". In other cases, a microfabricated filter can form a wall of a filtration chamber, and during filtration, filterable sample components exit the chamber via the filter.

Optionally, the filters may incorporate dielectrophoresis electrode structures. Electrodes can be built into or onto a filter, and can be used to move sample components away from a filter by negative dielectrophoresis.

Figure 3A:
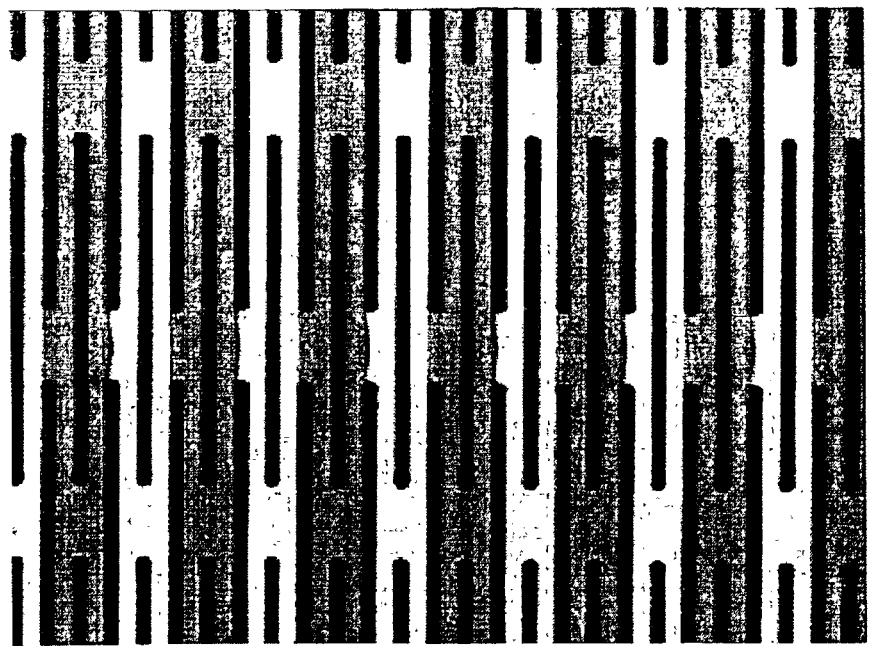
FIG. 3 depicts filters of the present invention having electrodes incorporated into their surfaces. A) a 20-fold magnification of a portion of a microfabricated filter having 2 micron slot widths. B) a 20-fold magnification of a portion of a microfabricated filter having 3 micron slot widths.
Figure 3B:
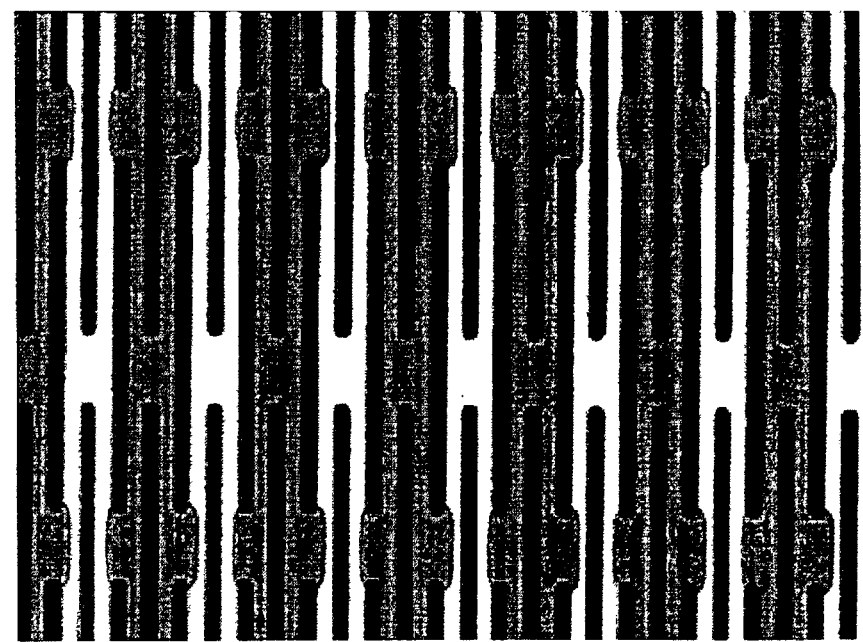

Filters having slots in the micron range that incorporate electrodes that can generate dielectrophoretic forces are illustrated in FIGS. 3A and 3B. In a number of the filters that have been made, the interdigitated electrodes of 18 micron width and 18 micron gaps were fabricated on the filters, which were made on silicon substrates. Individual filter slots were of rectangular shape with dimensions of 100 micron (length) by 2–3.8 micron (width). Each filter had a unique slot size (e.g. length by width: 100 micron by 2.4 micron, 100 micron by 3 micron, 100 micron by 3.8 micron). Along the length direction, the gap between the adjacent filter slots was 20 micron. Along the width direction, the adjacent slots were not aligned, instead, they were offset between the slots. The offset distance between neighboring columns of the filter slots were 50 micron or 30 micron, alternatively. The filter slots were positioned with respective to the electrodes so that the slot center lines along the length direction were aligned with the center line of the electrodes, or the electrode edges, or the center line of the gaps between the electrodes.

A filtration chamber of the present invention can optionally comprise or engage at least one active chip that can perform a mixing function. A chip can comprise silicon, glass, rubber, photoresist, or one or more metals, ceramics, polymers, copolymers, or plastics. A chip can comprise one or more flexible materials. A chip can be from about 1 $mm^2$ to about 0.25 $m^2$. Preferably, the size of the chips useable in the present methods is from about 4 $mm^2$ to about 25 $cm^2$. The shape of the chips useable in the present methods can be regular shapes such as square, rectangular, circular, or oval, or can be irregularly shaped. The active surface of a chip need not be flat, but can be curved, angled, etc. Chips useable in the methods of the present invention can have one or more acoustic elements or electrodes built into or onto the surface of the chip.

Preferred chips in a system of the present invention include acoustic chips for mixing of a sample, or dielectrophoresis chips that can be used to move sample components, such as cells, that are within the chamber. The use of applied acoustic forces to mix a sample is discussed above. The use of traveling-wave dielectrophoresis to transport sample component away from a filter and the use of negative dielectrophoresis to repel sample components away from a filter to prevent obstruction of the filter by non-filterable components are also described in the discussion of methods above. Acoustic, dielectrophoresis and traveling-wave dielectrophoresis chips and their use are also described in U.S. patent application Ser. No. 09/686,737, filed Oct. 10, 2000 entitled "Apparatus and Methods for Separation of Moieties on Chips"; U.S. application Ser. No. 09/636,104, filed Aug. 10, 2000, entitled "Methods for Manipulating Moieties in Microfluidic Systems"; and application Ser. No. 09/973,629, entitled "An Integrated Biochip System for Sample Preparation and Analysis", filed Oct. 9, 2001 all incorporated by reference in their entireties.

In addition, a multiple force chip that can provide both acoustic and dielectrophoretic (including traveling-wave dielectrophoretic) forces can also be employed in a filtration chamber of an automated system of the present invention to enhance filtration by acoustic mixing as well as dielectrophoretic translocation of particles. Multiple force chips are described in U.S. application Ser. No. 09/679,024, filed Oct. 4, 2000, incorporated by reference in its entirety.

Means for Directing Fluid Flow Through an Automated System

An automated system of the present invention also has means for directing fluid flow through the automated system. At least one power supply or signal source or control circuit can be used for the automated control and powering of fluid flow through the system, such as through channels, canals, tubing, conduits, filters, and the like. Means for directing fluid flow through the automated system can comprise one or more automatic mechanisms for providing force that results in fluid flow, such as syringe-type pumps that can produce positive or negative pressure, or peristaltic pumps. Automated fluid flow can also be effected at least in part by fluid uptake/dispensing systems that can provide for the transfer of sample, solutions or reagents into various vessels, chambers, or conduits of the automated system. Such fluid uptake/dispensing systems can utilize a variety of mechanisms, such as but not limited to positive and negative pressure pumps, peristaltic pumps, syringes, etc.

Means for directing fluid flow through the automated system can comprise a system of conduits that can connect different elements of the automated system, such as vessels, reservoirs, chambers, and columns. Preferred conduits are channels or canals that are molded or bored into a plastic casing, such as a cartridge. Other preferred conduits comprise tubing, such as tygon, Teflon, or rubber tubing, through which a fluid sample can flow.

In some aspects of the present invention, a filtration chamber can comprise one or more ports for the removal of filtered sample components from the chamber. In preferred aspects of the present invention, filtered sample components exit the chamber through outlet ports, and one or more conduits engage the ports so that in response to fluid flow, filtered sample components flow out of the outlet ports and through the one or more conduits. A conduit can be any enclosed space or tube that allows for the entry of a fluid sample, solution, or reagent into the chamber, or allows for the translocation of sample or sample components out of a chamber or vessel. In some preferred automated systems, conduits include molded tunnels or channels or tubing, for example, rubber or polymeric tubing, e.g., tygon or teflon tubing. Conduits that engage or lead to one or more ports of a chamber can be used to introduce a sample, solution, reagent, or preparation by any means, including a pump (for example, a peristaltic pump or infusion pump), pressure source syringe, or gravity feed.

A filtration chamber of automated system of the present invention can comprise one or more inlets, or openings in the walls of a chamber for the addition of sample, buffers, solutions, or reagents. Preferably, the automated system comprises means (at least one inlet, conduit, reservoir, or automated fluid uptake/dispensing system) for the addition of at least one solution or reagent to the sample.

A port (such as but not limited to an inlet) can be permanently open, or can comprise a flap or valve that allows the port to be reversibly closed. An inlet can provide means for the dispensing of sample into a filtration chamber by pipeting, dispensing, gravity feed, or by positive or negative pressure (for example, by a syringe mechanism). In some preferred embodiments, a filtration chamber of the present invention is part of a filtration unit in which valves control fluid flow through the chamber. For example, one preferred filtration chamber of the present invention comprises a valve-controlled inlet for the addition of sample (valve A in FIG. 14), a valve connected to a conduit through which negative pressure is applied for the filtration of the sample (valve B in FIG. 14), a valve controlling the flow of wash buffer into the filtration chamber for washing the chamber (valve C in FIG. 14), and an additional valve-controlled outlet for the exit of retained enriched cells from the chamber (valve D in FIG. 14). The automated control of the valves allows for sample and solutions to enter and exit the chamber, as well as the generation of fluid flow for filtering.

Means for Collecting Enriched Rare Cells

An automated system of the present invention comprises means for the collection of enriched rare cells. Such means can include structures for the collection, transfer, disposition, or storage of samples that can include such rare cells. For example, such means for the collection of enriched rare cells can include fluidic transfer devices such as but not limited to tubing, outlets, positive or negative pressure devices such as syringe pumps or peristaltic pumps. In one instance, a negative pressure device can draw an aliquot of sample and transfer that aliquot to another location or vessel. The means for the collection of enriched cells can include structures for the storage of samples, such as but not limited to containers, such as but not limited to test tubes, vials, plates, multi-well plates, tissue culture ware or the like.

Sample Rack

In some preferred embodiments, an automated system of the present invention comprises at least sample rack for holding vessels that contain samples, such as blood samples. A sample rack can provide for the processing of several to many samples simultaneously. The sample rack can, for example hold tubes that contain samples and position them such that solutions or reagents can be added to the tubes (such as by an automated fluid uptake/dispensing system). At least a portion of a sample, such as a portion of a sample to which one or more solutions or reagents has been added, or on which one or more debulking or separation steps has been performed, can also be withdrawn from vessels such as tubes that are secured in a sample rack and optionally transferred into one or more other vessels, conduits, or chambers for further processing. In some preferred embodiments of the present invention, as sample rack can also secure tubes that hold sample and move to perform a mixing operation, such as rocking, inversion, or agitation, or as a separation is performed, for example, a magnetic separation using one or more magnets held proximal to the tubes in the rack.

In preferred embodiments of the present invention, several samples, such as blood samples from different individuals, are provided in tubes that can be placed in a sample rack of an automated system for enriching rare cells of a fluid sample. The rack can optionally move on a track for positioning beneath a fluid withdrawal/dispensing system. The rack can also preferably move to rock the tubes to provide a mixing function and position or hold tubes as a separation, such as a magnetic separation, is performed.

Fluid Volume Sensing Means

An automated system of the present invention can have means for sensing the volume of a fluid, such as, but not limited to, the volume of a fluid sample, including a fluid sample supernatant. The means for sensing the volume of a fluid preferably relies on optical sensing, such as detection of transmittance, absorption, reflectance, or fluorescence, and can comprise a light source, such as a light bulb or LED, and a sensing structure such as CCDs or photomultipliers appropriately aligned with the light source or sources. Wavelengths for particular sensing applications can be readily determined, for example, for turbidity (600 nm). A light source and detection device can be mobile, so that they can continuously or in graduated fashion scan the length of the tube or column that contains the sample, or the fluid bolume sensing means can have multiple light sources and multiple detectors that are oriented vertically and can simultaneously detect optical parameters and thereby determine the volume of a sample (or a subfraction thereof). Because blood samples contain cells such as RBCs and WBCs, a change in the optical characteristics can determine the locus of particular cell types. It is also possible to fluorescently label cells so that fluorescence can be used for localization.

For example, a light source, such as but not limited to a light bulb or LED, can interrogate the tube or column of sample. The transmittance, absorption or reflectance of the incident light can be measured by appropriate structures, such as CCDs or photomultipliers. Because layers of the sample column with a high density of RBCs are optically dense and do not transmit light well, the interface between high and low RBC densities can be determined by such optical methods. The instrument can localize such interface or zone and calculate the volume in the tube by the height of the column. This can be done by using a light source and detection device that are mobile, and either continuously or in graduated fashion scan the length of the tube or column, or by having multiple light sources and detectors that are oriented vertically and can simultaneously detect optical density and thereby determine the volume of the sample (or subfraction thereof). The automated system then calculates the amount of combined solution to add to each sample tube, and adds the appropriate amounts using an automated fluid dispensing system.

Separation Chamber

An automated system for the separation of rare cells from a fluid sample can optionally comprise at least one separation chamber, where a separation chamber is a chamber where at least one separation of sample components can occur.

A separation chamber can be a separation column, in which the separation takes place while sample flows through the column. In preferred aspects of these embodiments, a separation column is a cylindrical structure comprised of glass, acrylic, or plastic that can accommodate a fluid volume of between 0.1 milliliter and 100 milliliters, preferably between 0.5 and 50 milliliters, and more preferably between one and 20 milliliters. A separation column of the present invention can be of any dimensions, but preferably its length is greater than its width. A separation column of an automated system preferably has ports at opposite ends of the column, for the entry and exit of a fluid sample or components thereof, or for the addition or removal of reagents, solutions, or buffers. A separation column of the present invention can comprise elements that aid in the separation of components of a fluid sample, such as matrices, specific binding members, one or more active chips, or one or more permanent magnets. For example, one or more surfaces of the separation column can have attached specific binding members that can be used to capture one or more components of a sample, or the separation column can be packed with a polymeric matrix to which specific binding members are bound. Alternatively, a separation column of the present invention can engage one or more magnets along its length that can be used to capture magnetic beads to which undesirable components of a sample can be directly or indirectly bound. One or more magnets can be permanent magnets, or can be electromagnetic elements provided on a chip surface that can be activated by a power source. In preferred embodiments, one or more magnets used in the separation of sample components are external to a separation column. External magnets can reversibly or permanently positioned alongside the separation column for performing magnetic separations.

A separation chamber that is not a column can also comprise specific binding members, such as one or more specific binding members that can bind one or more components of a sample. A separation chamber that is not a column can also comprise or engage one or more active chips.

Such active chips comprise functional elements that can, at least in part, generate physical forces that can be used to translocate sample components from one area of a chamber to, another area of a chamber. Preferred functional elements of a chip for translocating sample components are electrodes and electromagnetic units. Chips comprising electrodes and electromagnetic units for the translocation of sample components and their use are described in U.S. application Ser. No. 09/973,629, entitled "An Integrated Biochip System for Sample Preparation and Analysis", filed Oct. 9, 2001, U.S. application Ser. No. 09/686,737, filed Oct. 10, 2000 entitled "Apparatus and Methods for Separation of Moieties on Chips", U.S. application Ser. No. 09/636,104, filed Aug. 10, 2000, entitled "Methods for Manipulating Moieties in Microfluidic Systems", U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations", and U.S. application Ser. No. 09/679,024, having filed Oct. 4, 2000, entitled "Apparatuses Containing Multiple Active Force Generating Elements and Uses Thereof". All are incorporated by reference in their entireties. The forces used to translocate sample components on an active chip of the present invention can be dielectrophoretic forces, electromagnetic forces, traveling wave dielectrophoretic forces, or traveling wave electromagnetic forces.

An active chip of an automated system of the present invention can perform more than one separation function using the same, or one or more different functional elements that provide, at least in part, sources of physical forces used in processes or tasks carried out on the chip. Different functional elements on a chip of a system of the present invention can optionally be positioned in different areas of the same chip. In alternative embodiments comprising a chip that has different functional elements, the regions of the chip having different functional elements can be in close proximity, such that sample components are freely and readily diffusible among the different functional elements, and preferably the different functional elements are at least partially interspersed with one another. In yet other embodiments, different functional elements can be provided in different structurally linked substrates (where a substrate is a surface for holding or supporting a moiety to be manipulated) that are vertically oriented with respect to one another. For examples of multiple force generating chips see U.S. application Ser. No. 09/679,024, entitled "Apparatuses Containing Multiple Active Force Generating Elements and Uses Thereof" filed Oct. 4, 2000, herein incorporated by reference.

An active chip that performs at least one separation function in an automated system of the present invention can be within or integral to a separation chamber, or can irreversibly, or preferably, reversibly engage a separation chamber. A separation chamber can comprise any suitable material, for example, silicon, glass, metal, ceramics, polymers, plastics, etc. and can be of a rigid or flexible material. Preferred materials for a chamber include materials that do not interfere with the manipulation of components of a sample, for example, insulating materials that do not bind charged or polarized molecules, such as certain plastics and polymers, for example, acrylic, or glass. A separation chamber can be of any shape or size, and can accommodate a range of volumes, but preferably a filtration chamber of the present invention has a volumetric capacity of from one microliter to 0.1 liter, more preferably from 10 microliters to 50 milliliters, and most preferably from 100 microliters to 20 milliliters.

A separation chamber preferably has at least two ports through which sample (including at least partially processed sample), sample components, buffers, solutions, and reagents can be added and removed. Preferably, conduits engage the ports and allow fluid flow through the chamber for at least a portion of the time that an automated system of the present invention is in operation. Preferably, the ports or conduits can be closed for at least a portion of the time that an automated system of the present invention is in operation.

Cartridge

In some preferred embodiments of the present invention, at least a portion of the components automated system of the present invention can be enclosed in a cartridge, where a cartridge is a unit that contains or connects different components of the automated system, and has molded conduits. For example, a filtration chamber, a separation column, one or more separation chips, and conduits providing fluid flow through the system can be held within a cartridge. The cartridge can optionally engage chips, such as active chips, one or more magnets, conduits, at least one power supply, or a platform during its operation. In some preferred aspects of the present invention, a cartridge that house elements of the automated system can engage a platform that comprises one or more permanent magnets, such that the one or more permanent magnets can be adjacent to one or more separation columns that are part of the automated system, and thereby effect magnetic separations in the separation columns. A cartridge can also engage one or more active chips, such as chips having acoustic units, electromagnetic units, or electrodes. A cartridge can also engage a power supply that can provide current to electrode structures on active chips of the automated system, or can engage one or more means for directing fluid flow through the automated system. A cartridge can optionally be disposable for ease of use and to avoid contamination of samples.

Automated System Comprising Sedimentation and Separation

In another preferred embodiment of the an automated system for enriching rare cells of the present invention, an automated system comprises at least one filtration chamber that comprises at least one microfabricated filter that comprises from 100 to 250,000 tapered slots having a width of 2.5 to 5 microns, varying by no more than 20%, or approximately 0.5 micron in the width of the slots, and a length of from about 20 microns to about 250 microns, varying by no more than 10%, or from 2 to 20 microns, in the length of the slots.

In this embodiment, the automated system also has one or more racks or holders that can hold tubes or other vessels that contain sample, a robotic mechanism that can be used for mixing of samples (for example, an arm that can rock or invert the rack of tubes) and positioning of the rack, an automatic fluid uptake and dispensing system where fluid delivery is provided by an electrically powered pump, at least one magnet positioned such that one or more tubes can be placed in proximity to a magnet, at least one filtration chamber, and at least one vessel for containing enriched rare cells.

The automated system can optionally comprise a housing that can enclose the automatic fluid uptake/dispensing system, one or more magnets, one or more filtration chambers, and one or more vessels for containing collected enriched rare cells. Preferably, a rack for holding one or, preferably, a plurality of sample tubes can be manually or automatically moved in and out of the housing for the loading of sample tubes. (In an alternative, the housing can have a lid that can be opened for inserting sample tubes or vessels into a rack or holder.) The rack can be positioned by the user, or preferably, automatically, so that one or more solutions can be added to the one or more sample tubes, such as beneath a fluid dispensing system. The rack preferably can move to agitate, rotate, tilt, rock, or invert the tubes. The movement of the rack can promote mixing of the sample and a solution or reagent added to the sample.

One or more magnets can be attached to a frame so that tubes can be positioned adjacent to the one or more magnets, or alternatively, the frame comprising one or more magnets can be positioned such that the one or more magnets are adjacent to the tubes.

The system also comprises one or preferably a plurality of filtration units, each of which comprises a filtration chamber, and preferably a loading reservoir that can hold sample before it enters a filtration chamber. A filtration chamber comprises one or more microfabricated filters of the present invention. Preferably, a filtration chamber comprises a single microfabricated filter of the present invention comprising from 100 to 250,000 tapered pores that have a width of between one micron and one thousand microns, varying in width by 20% or less, and have a length of between micron and one thousand microns, varying in length by 20%. A wide variety of pore shapes and sizes are possible, depending on the type of sample to be processed and the sample components to be filtered. A filtration chamber is preferably structured such that it comprises two subchambers (an antechamber and a post-filtration chamber) separated by a single microfabricated filter. A loading reservoir can connected by a port or conduit to a filtration chamber. A port leading to the filtration chamber preferably comprises a valve that is automatically controlled to regulate the amount of sample and, optionally, wash solution, that enters a filtration chamber.

A filtration chamber also has ports that allow filtered sample (effluent) to exit the filtration chamber, and optionally but preferably ports for providing negative pressure for fluid flow through the filtration chamber and for removal of enriched cells from the filtration chamber.

The automated system can have a collection chamber into which nonfilterable sample components can be transferred after filtration has been completed. Preferably, the collection chamber is connected to the antechamber by a port that comprises a valve that can be automatically controlled for regulation the flow of fluid from the antechamber into the collection chamber.

In addition, the automated system preferably has one, or preferably a multiplicity of collection tubes for holding the enriched sample components. In some preferred aspects of this embodiment, collected sample components can be transferred from a collection chamber to a tube that can be removed from the automated system. Collection tubes are preferably disposable.

Figure 15:
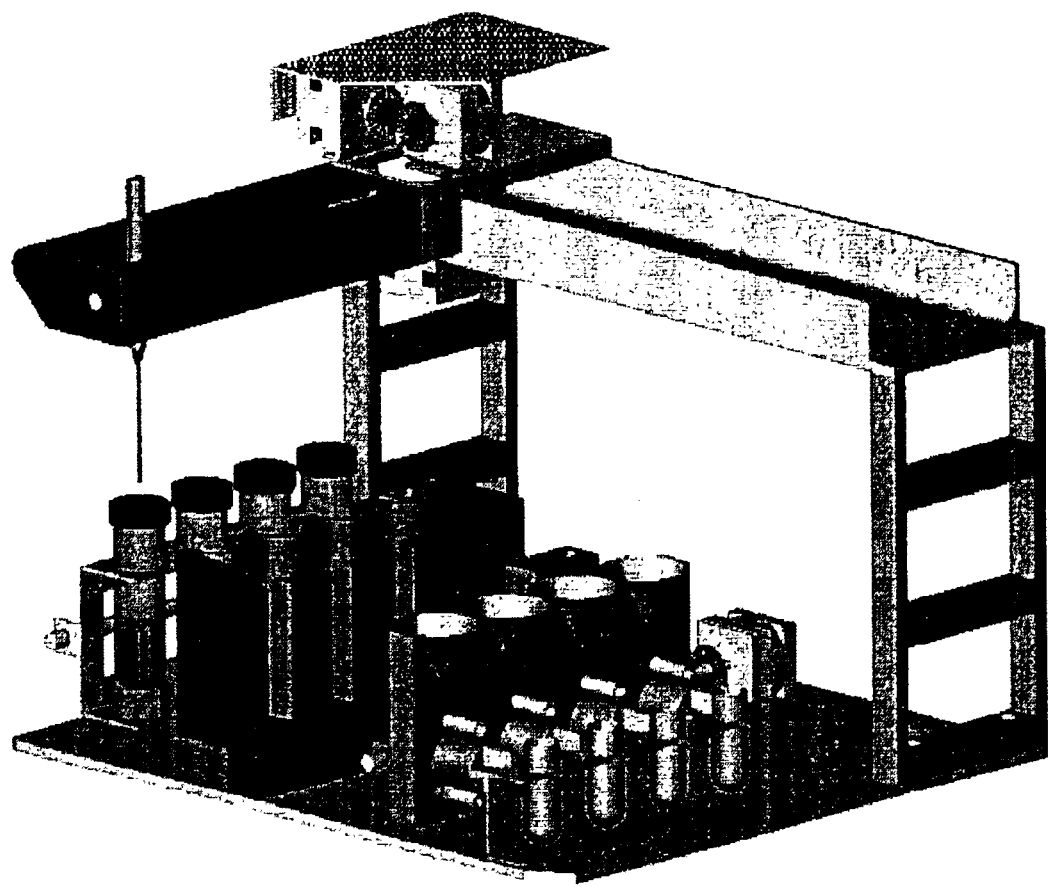
FIG. 15 shows a model of an automated system of the present invention.
Figure 16A:
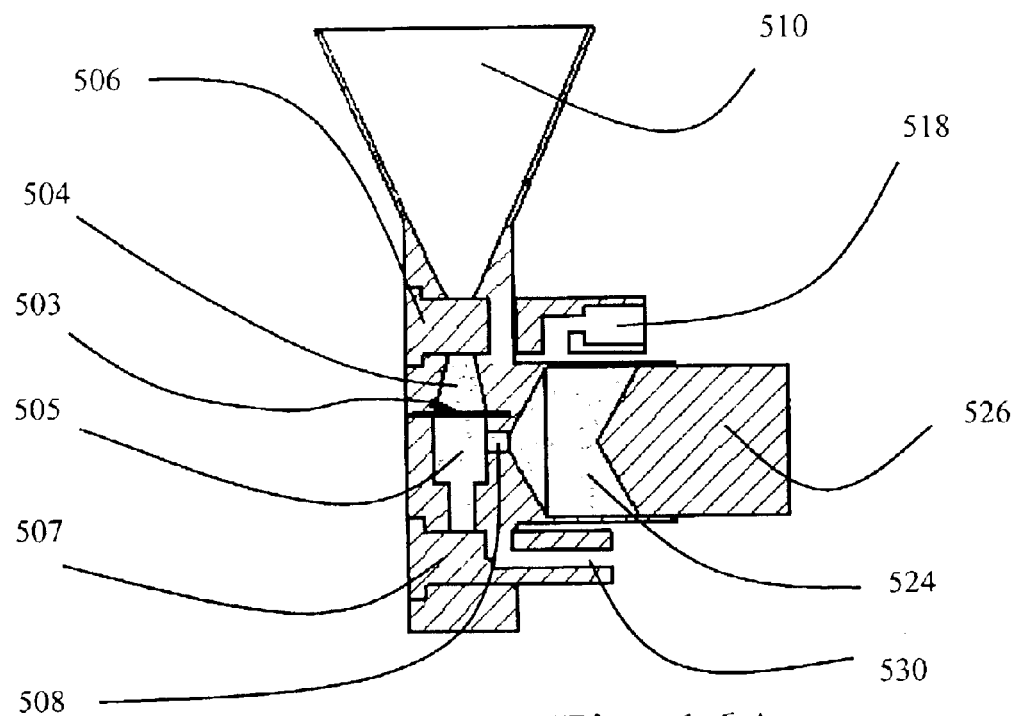
FIG. 16 depicts the filtration process of an automated system of the present invention. A) shows the filtration unit having a loading reservoir (510) connected through a valve (506) to a filtration chamber that comprises an antechamber (504) separated from a post-filtration subchamber (505) by a microfabricated filter (503). A wash pump (526) is connected to the lower chamber through a valve (508) for pumping wash buffer (524) through the lower subchamber. Another valve (507) leads to another negative pressure pump used to promote fluid flow through the filtration chamber and out through an exit conduit (530). A collection vessel (518) can reversibly engage the upper chamber (504). B) shows a blood sample (525) loaded into the loading reservoir (510). In C) the valve (507) that leads to a negative pressure pump used to promote fluid flow through the filtration chamber is open, and D) and E) show the blood sample being filtered through the chamber. In F) wash buffer introduced through the loading reservoir is filtered through the chamber. In G), valve (508) is open, while the loading reservoir valve (506) is closed, and wash buffer is pumped from the wash pump (526) into the lower chamber. In H) the filtration valve (507) and wash pump valve (508) are closed and in I) and J) the chamber is rotated 90 degrees. K) shows the collection vessel (518) engaging the antechamber (504) so that fluid flow generated by the wash pump (526) causes rare target cells (520) retained in the antechamber to flow into the collection tube as depicted in L) and M).
Figure 16B:
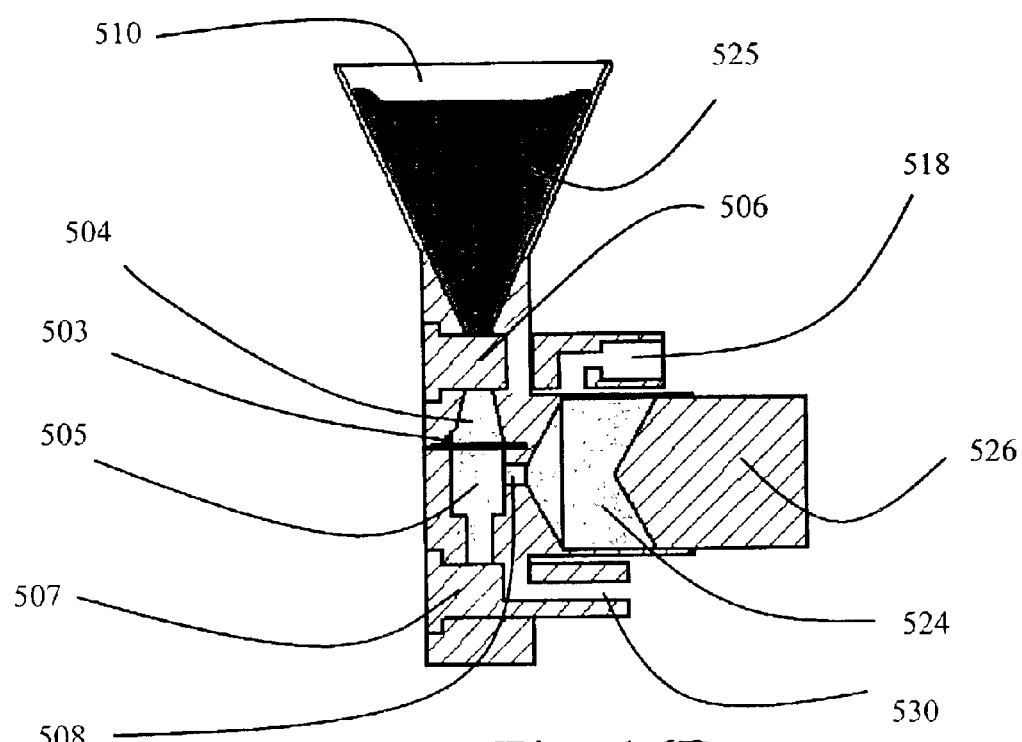
Figure 16C:
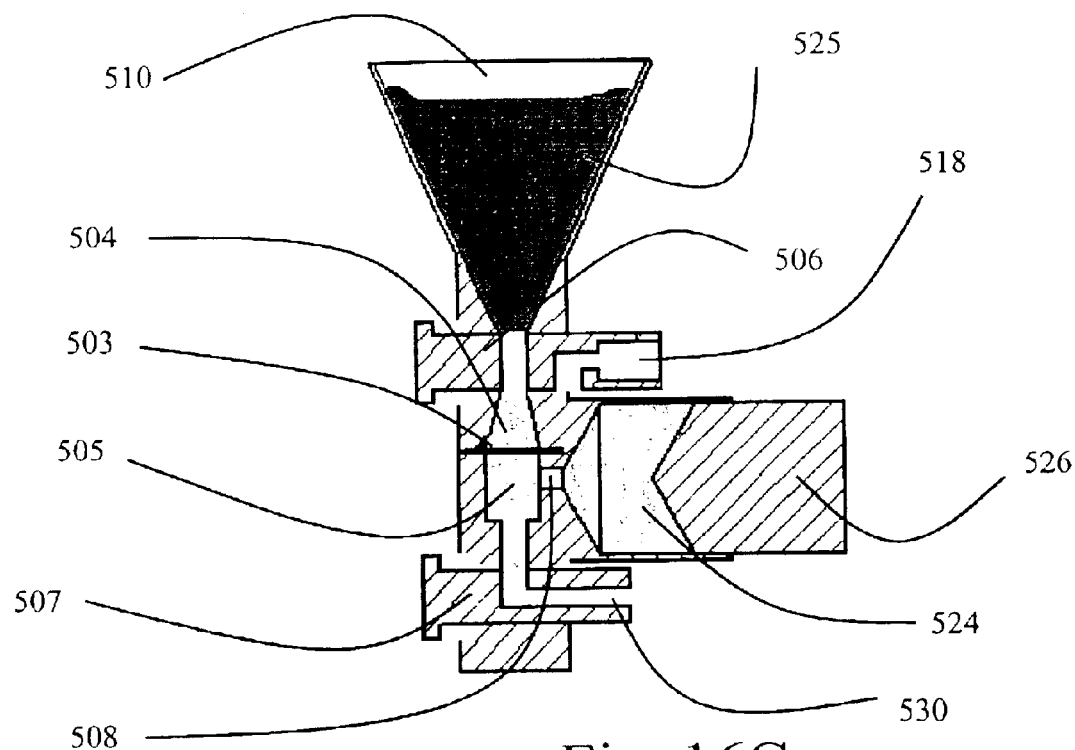
Figure 16D:
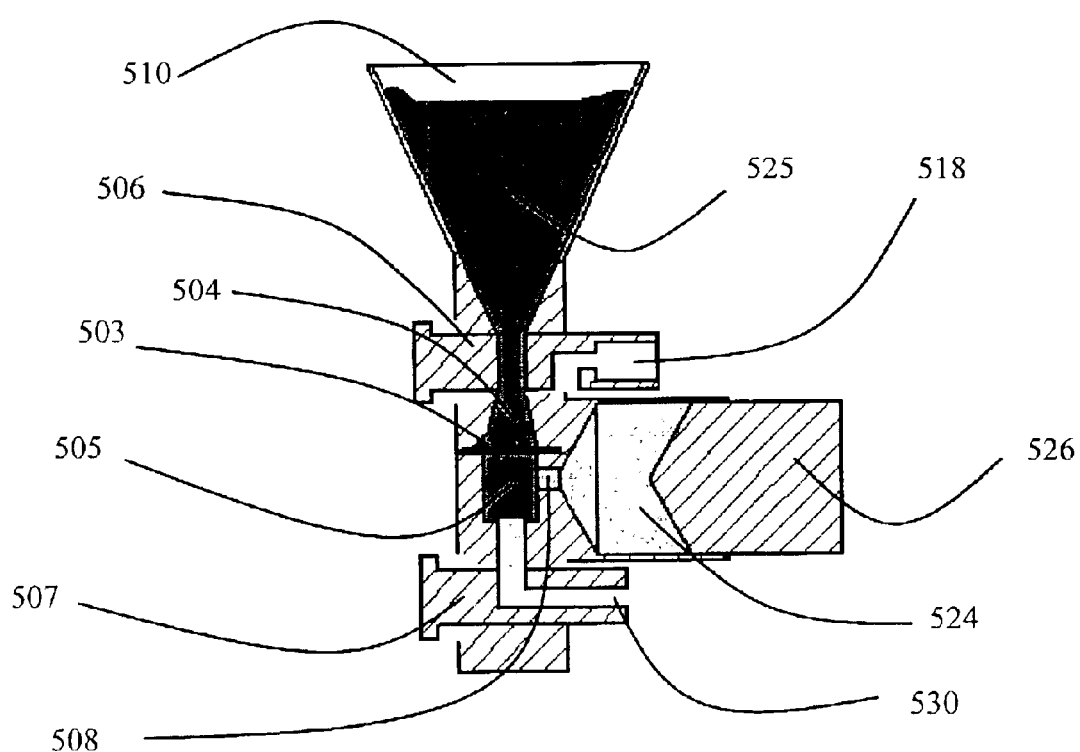
Figure 16E:
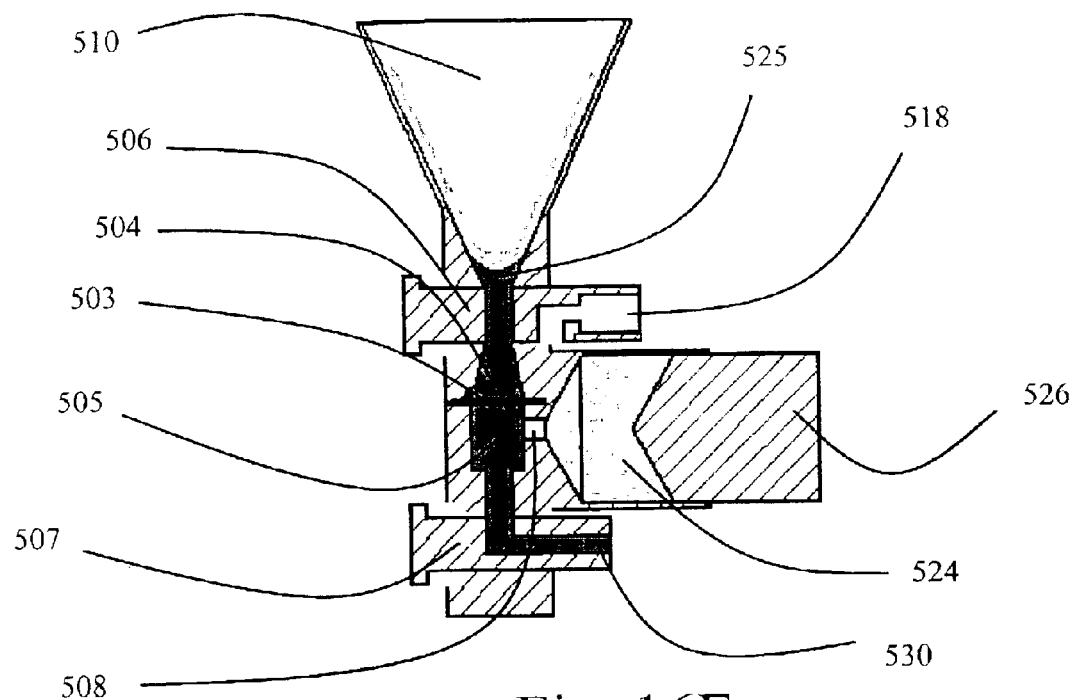
Figure 16F:
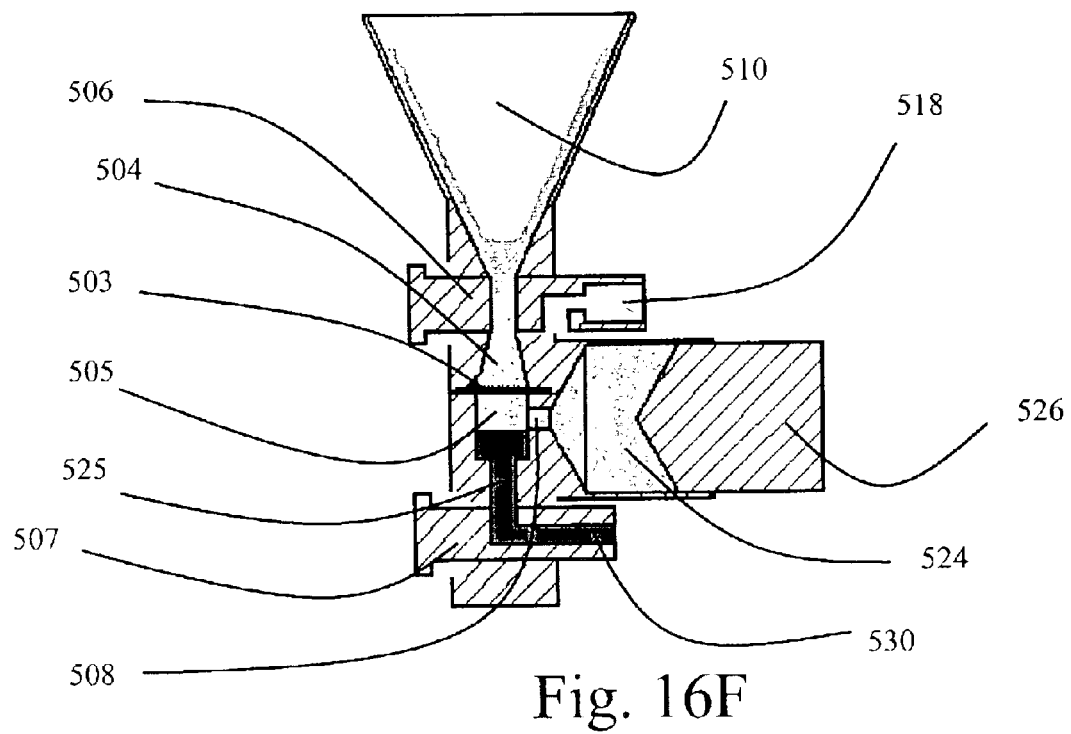
Figure 16G:
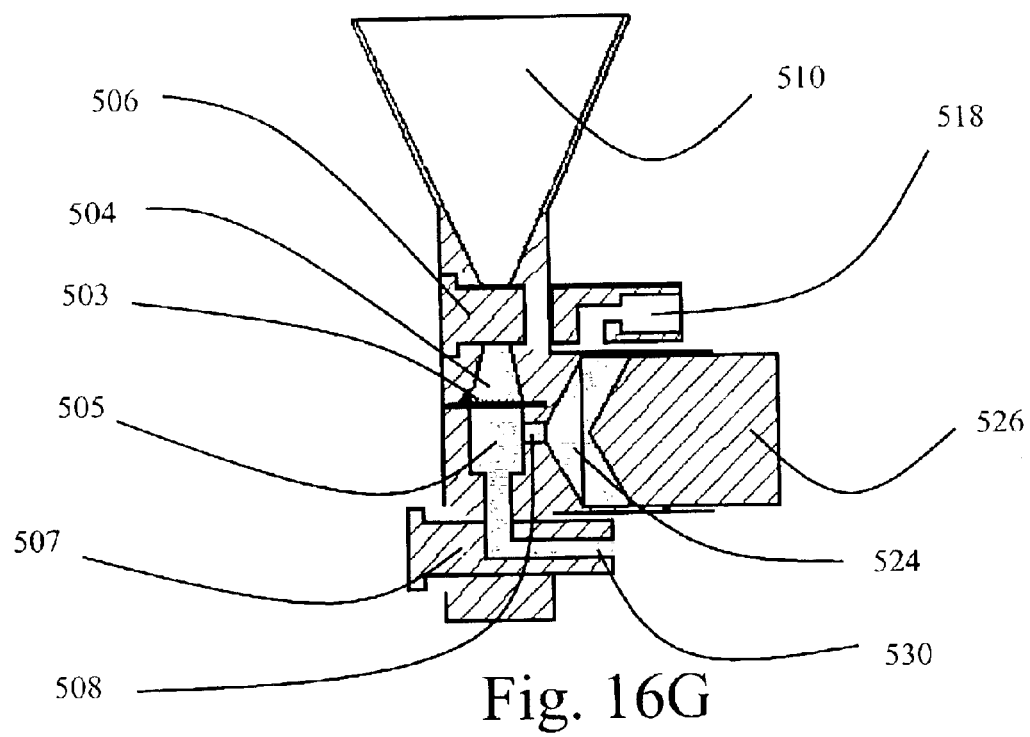
Figure 16H:
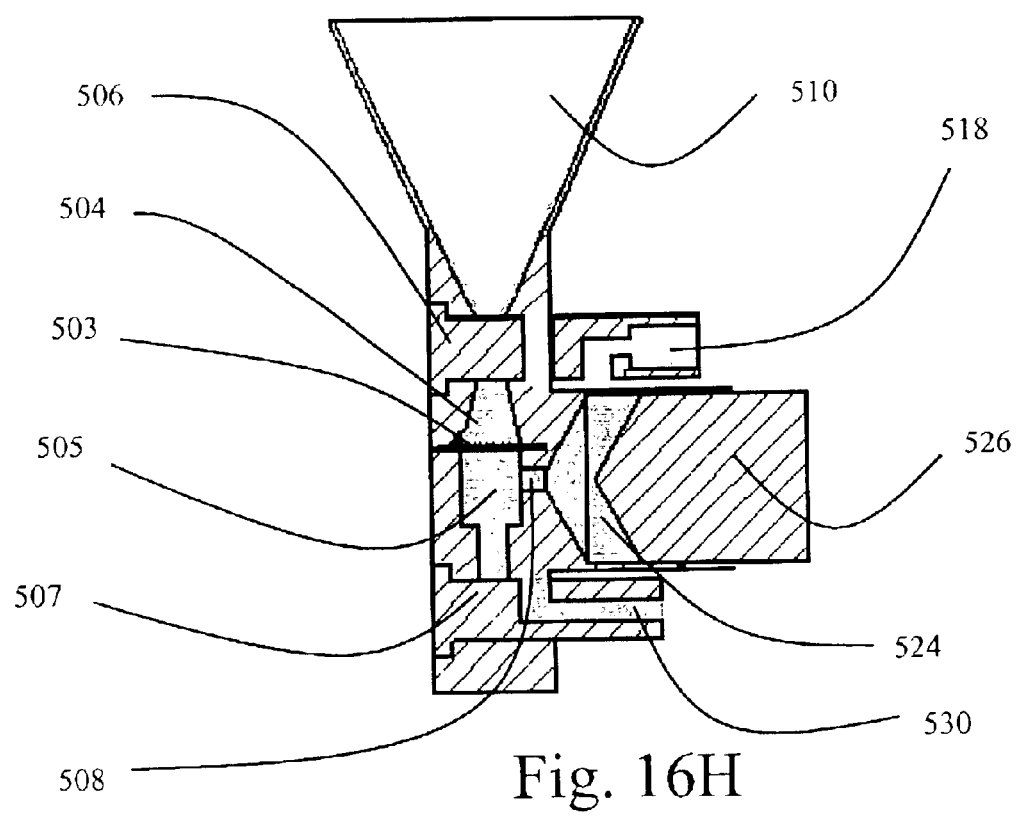
Figure 16I:
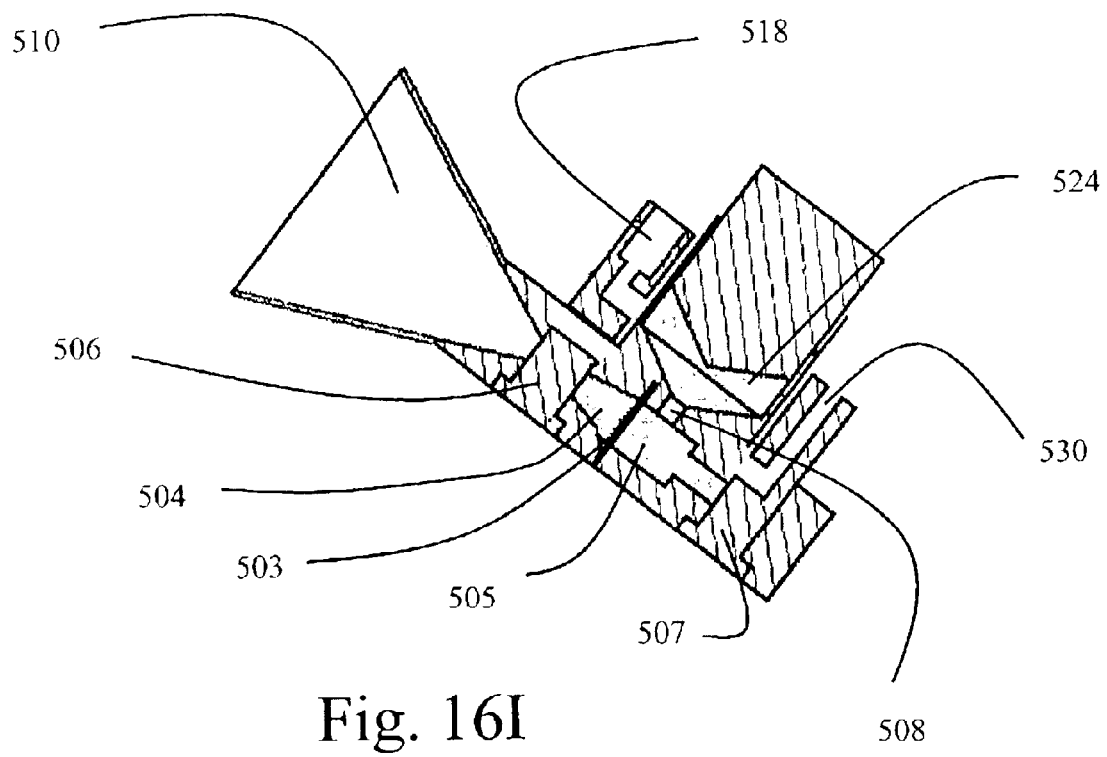
Figure 16J:
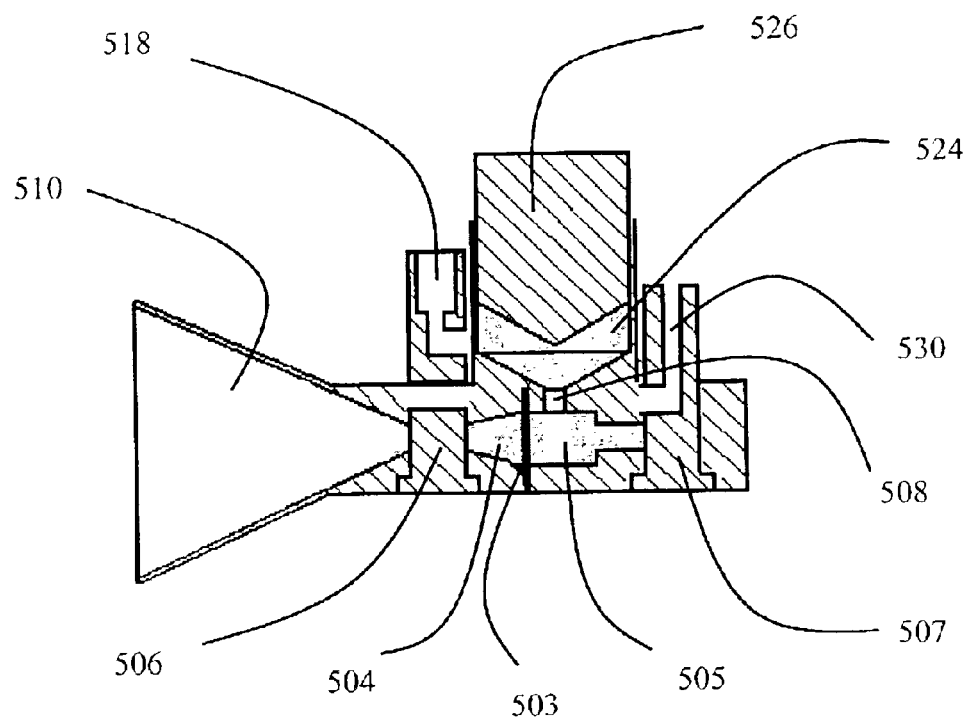
Figure 16K:
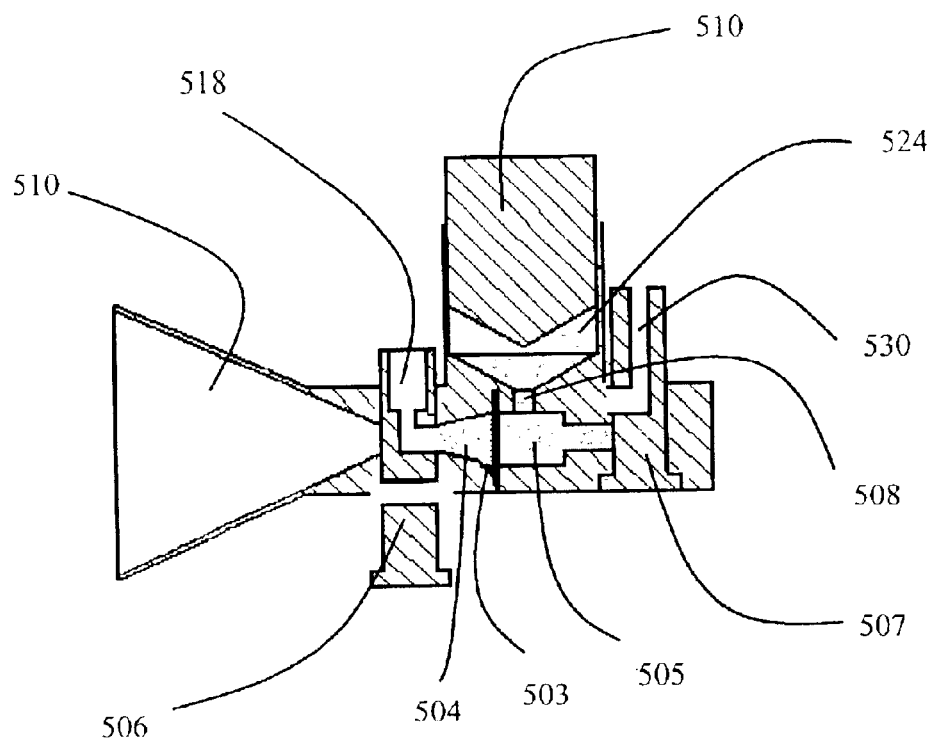
Figure 16L:
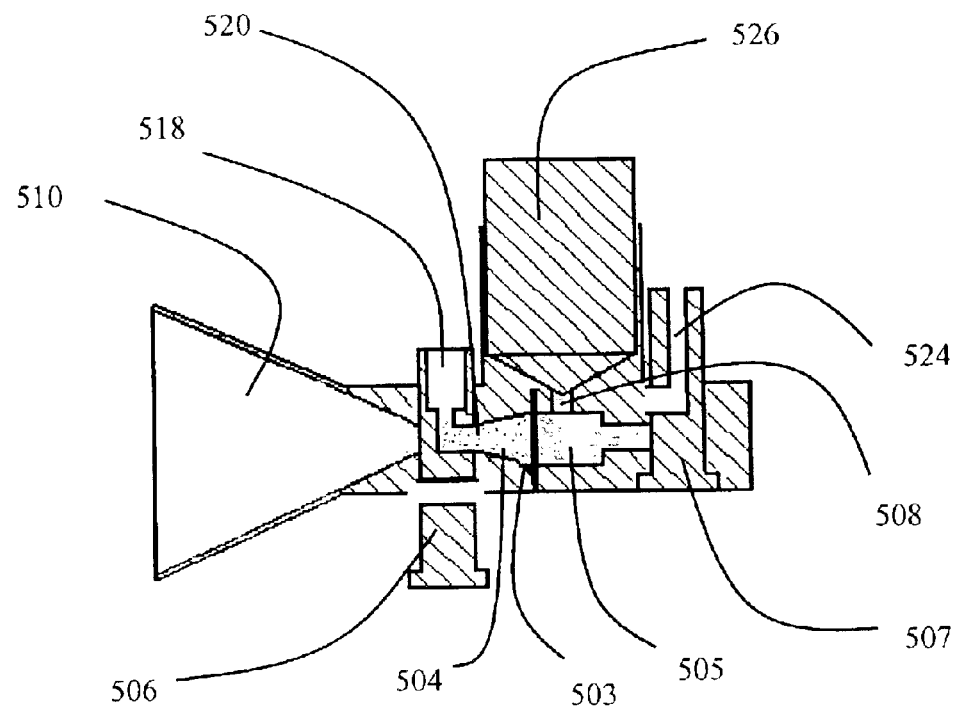
Figure 16M:
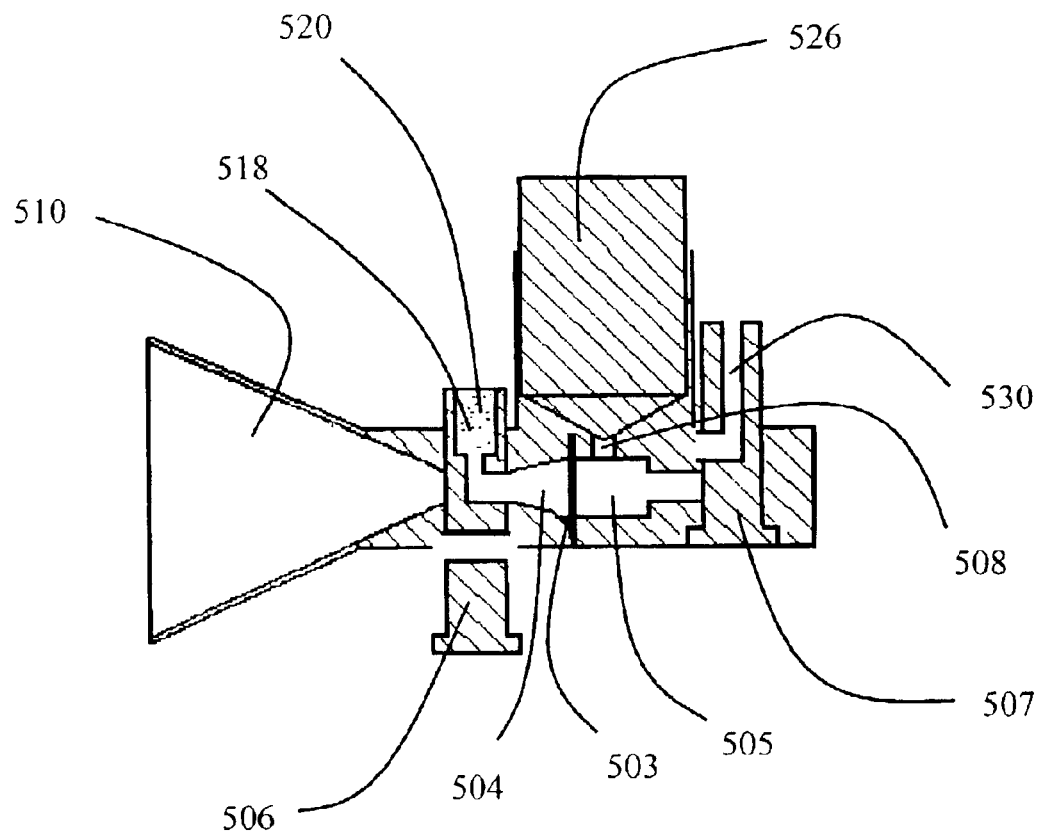

FIG. 15 depicts an example of this type of automated system. The rack holds a multiplicity of tubes, and can be placed in the automated system automatically or manually. The fluid dispensing/uptake system comprises a single outlet for dispensing a solution that is positioned above the rack and can move to dispense solution into each tube. The rack can move on a track or by the use a robotic arm for positioning the tubes away from the fluid dispensing/uptake system and rocking the tubes.

The automated system comprises a multiplicity of filtration chambers, each of which is connected to a loading reservoir is positioned directly over the filtration chamber. The loading reservoirs are funnel-shaped, and open at the upper end. The lower neck of the loading reservoir that engages the inlet of the filtration chamber comprises a valve that can be opened and closed automatically to control the flow of sample into the filtration chamber. The antechamber also has a port, regulated by a valve, that leads to a collection vessel.

The filtration chamber also has a port in the post-filtration subchamber for the exit of filtered components, as well as a port that connects the post-filtration subchamber with a negative pressure pump that promotes fluid flow through the filtration chamber. The ports also comprise automatically controlled valves.

VI. Methods of Using Automated Systems for Enriching Rare Cells of a Fluid Sample The present invention also includes methods of enriching rare cells of a fluid sample using an automated system of the present invention. The method includes: introducing a sample into an automated system of the present invention; filtering the sample through at least one filtration chamber or the automated system; and collecting enriched rare cells from at least one vessel or at least one outlet of the automated system.

Sample

A sample can be any fluid sample, such as an environmental sample, including air samples, water samples, food samples, and biological samples, including extracts of biological samples. Biological samples can be blood, a bone marrow sample, an effusion of any type, ascities fluid, pelvic wash fluid, pleural fluid, spinal fluid, lymph, serum, mucus, sputum, saliva, urine, semen, occular fluid, extracts of nasal, throat or genital swabs, cell suspension from digested tissue, or extracts of fecal material. Biological samples can also be samples of organs or tissues, including tumors, such as fine needle aspirates or samples from perfusions of organs or tissues. Biological samples can also be samples of cell cultures, including both primary cultures and cell lines. The volume of a sample can be very small, such as in the microliter range, and may even require dilution, or a sample can be very large, such as up to about two liters for ascites fluid. One preferred sample is a urine sample. Another preferred sample is a blood sample.

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

Introduction of Sample

In some preferred embodiments of the present invention, one or more samples can be provided in one or more tubes that can be placed in a rack of the automated system. The rack can be automatically or manually engaged with the automated system for sample manipulations.

Alternatively, a sample can be dispensed into an automated system of the present invention by pipeting or injecting the sample through an inlet of an automated system, or can be poured, pipeted, or pumped into a conduit or reservoir of the automated system. Prior to the dispensing of a sample into a vessel or chamber of the automated system, solutions or reagents can optionally be added to the sample. Solutions or reagents can optionally be added to a sample before the sample is introduced into an automated system of the present invention, or after the sample is introduced into an automated system of the present invention. If a solution or reagent is added to a sample after the sample is introduced into an automated system of the present invention, it can optionally be added to the sample while the sample is contained within a tube, vessel, or reservoir prior to its introduction into a filtration chamber. Alternatively, a solution or reagent can be added to a sample through one or more conduits, such as tubing, where the mixing of sample with a solution or reagent takes place in conduits. It is also possible to add one or more solutions or reagents after the sample is introduced into a chamber of the present invention (such as, but not limited to, a filtration chamber), by adding one or more of these directly to the chamber, or through conduits that lead to the chamber.

The sample (and, optionally, any solutions, or reagents) can be introduced into the automated system by positive or negative pressure, such as by a syringe-type pump. The sample can be added to the automated system all at once, or can be added gradually, so that as a portion of the sample is being filtered, additional sample is added. A sample can also be added in batches, such that a first portion of a sample is added and filtered through a chamber, and then further batches of a sample are added and filtered in succession.

Filtering the Sample Through a Chamber of the Automated System

A sample can be filtered in an automated system of the present invention before or after undergoing one or more debulking steps or one or more separation steps. The sample can be directly transferred to a filtration chamber (such as by manual or automated dispensing) or can enter a filtration chamber through a conduit. After a sample is added to a filtration chamber, it is filtered to reduce the volume of the sample, and, optionally, to remove undesirable components of a sample. To filter the sample, fluid flow is directed through the chamber. Fluid flow through the chamber is preferably directed by automatic rather than manual means, such as by an automatic syringe-type pump. The pump can operate by exerting positive or negative pressure through conduits leading to the filtration chamber. The rate of fluid flow through a filtration chamber can be any rate that allows for effective filtering, and for a whole blood sample is preferably between about one and about 1000 milliliters per hour, more preferably between about five and about 500 milliliters per hour, and most preferably between about ten and about fifty milliliters per hour. Following the addition of a sample to a filtration chamber, a pump or fluid dispensing system can optionally direct fluid flow of a buffer or solution into the chamber to wash additional filterable sample components through the chamber.

When the sample is added to the filtration chamber, and fluid flow is directed through the chamber, pores or slots in the filter or filters can allow the passage of fluid, soluble components of the samples, and some non-soluble components of a fluid sample through one or more filters, but, because of their dimensions, can prevent the passage of other components of the fluid sample through the one or more filters.

For example, in preferred embodiments a fluid sample can be dispensed into a filtration chamber that comprises at least one filter that comprises a plurality of slots. The chamber can have ports that are optionally connected to conduits through which a buffer or solution and the fluid sample or components thereof can flow. When the sample is added to the chamber, and fluid flow is directed through the chamber, the slots can allow the passage of fluid and, optionally, some components of a fluid sample through the filter, but prevent the passage of other components of the fluid sample through the filter.

In some embodiments of the present invention, an active chip that is part of the filtration chamber can be used to mix the sample during the filtration procedure. For example, an active chip can be an acoustic chip that comprises one or more acoustic elements. When an electric signal from a power supply activates the acoustic elements, they provide vibrational energy that causes mixing of the components of a sample. An active chip that is part of a filtration chamber of the present invention can also be a dielectrophoresis chip that comprises microelectrodes on the surface of a filter. When an electric signal from a power supply is transmitted to the electrodes, they provide a negative dielectrophoretic force that can repel components of a sample from the filter surface. In this embodiment, the electrodes on the surface of the filter/chip are preferably activated intermittently, when fluid flow is halted or greatly reduced.

Mixing of a sample during filtration is performed to avoid reductions in the efficiency of filtration based on aggregation of sample components, and in particular their tendency to collect, in response to fluid flow through the chamber, at positions in the chamber where filtering based on size or shape occurs, such as dams, slots, etc. Mixing can be done continuously through the filtration procedure, such as through a continous activation of acoustic elements, or can be done in intervals, such as through brief activation of acoustic elements or electrodes during the filtration procedure. Where dielectrophoresis is used to mix a sample in a filtration chamber, preferably the dielectrophoretic force is generated in short intervals (for example, from about two seconds to about 15 minutes, preferably from about two to about 30 seconds in length) during the filtration procedure; for example, pulses can be given every five seconds to about every fifteen minutes during the filtration procedure, or more preferably between about every ten seconds to about every one minute during the filtration procedure. The dielectrophoretic forces generated serve to move sample components away from features that provide the filtering function, such as, but not limited to, slots.

During the filtration procedure, filtered sample fluid can be removed from the filtration chamber by automated fluid flow through conduits that lead to one or more vessels for containing the filtered sample. In preferred embodiments, these vessels are waste receptacles. After filtration, fluid flow can optionally be directed in the reverse direction through the filter to suspend retained components that may have settled or lodged against the filter.

After the filtration procedure (and optionally, a mixing and incubation with one or more specific binding members), sample components that remain in the filtration chamber after the filtration procedure can directed out of the chamber through additional ports and conduits that can lead to other elements of the automated system for further processing steps, or can be removed from the filtration chamber or a collection vessel by pipeting or a fluid uptake means. Ports can have valves or other mechanisms for controlling fluid flow. The opening and closing of ports can be automatically controlled. Thus, ports that can allow the flow of debulked (retained) sample out of a filtration chamber (such as to other chambers or collection vessels) can be closed during the filtration procedure, and conduits that allow the flow of filtered sample out of a filtration chamber can optionally be closed after the filtration procedure to allow efficient removal of remaining sample components.

Selective Removal of Undesirable Components of a Sample

Optionally, sample components that remain in the filtration chamber after the filtration procedure can be directed by fluid flow to an element of the automated system in which undesirable components of a sample can be separated from the sample. In some embodiments of the present invention, prior to removing the debulked sample retained in the filtration chamber, one or more specific binding members can be added to the debulked sample and mixed in the filtration chamber, using, for example, one or more active chips that engage or are a part of the filtration chamber to provide physical forces for mixing. Preferably, one or more specific binding member is added to the debulked sample in the filtration chamber, ports of the chamber are closed, and acoustic elements are activated either continuously or in pulsed, during the incubation of debulked sample and specific binding members. Preferably, one or more specific binding members are antibodies that are bound to magnetic beads. The specific binding members can be antibodies that bind desirable sample components, such as fetal nucleated red blood cells, but preferably the specific binding members are antibodies that bind undesirable sample components, such as white blood cells.

In preferred embodiments of the present invention, sample components that remain in the filtration chamber after the filtration procedure are incubated with magnetic beads, and following incubation, are directed by fluid flow to a separation column. Preferably, a separation column used in the methods of the present invention is a cylindrical glass, plastic, or polymeric column with a volumetric capacity of between about one milliliter and ten milliliters, having entry and exit ports at opposite ends of the column. Preferably, a separation column used in the methods of the present invention comprises or can be positioned alongside at least one magnet that runs along the length of the column. The magnet can be a permanent magnet, or can be one or more electromagnetic units on one or more chips that is activated by a power source.

Sample components that remain in the filtration chamber after the filtration procedure can be directed by fluid flow to a separation column. Reagents, preferably including a preparation of magnetic beads, can be added to the sample components before or after they are added to the chamber. Preferably, reagents are added prior to transfer of sample components to a separation chamber. Preferably a preparation of magnetic beads added to the sample comprises at least one specific binding member, preferably a specific binding member that can directly bind at least one undesirable component of the sample. However, it is also possible to add a preparation of magnetic beads that comprise at least one specific binding member that can indirectly bind at least one undesirable component of the sample. In this case, it is necessary to also add a primary specific binding partner that can directly bind undesirable components to the sample. A primary specific binding partner is preferably added to the sample before the preparation of magnetic beads comprising a secondary specific binding partner is added to the sample, but this is not a requirement of the present invention. Bead preparations and primary specific binding partners can be added to a sample before or after the addition of the sample to a separation column, separately or together.

In embodiments where magnetic beads comprise primary specific binding members, the sample and magnetic bead preparation are preferably incubated together for between about five and about sixty minutes before magnetic separation. In embodiments where a separation column comprises or is adjacent to one or more permanent magnets, the incubation can occur prior to the addition of the sample to the separation column, in conduits, chambers, or vessels of the automated system. In embodiments where a separation column comprises or is adjacent to one or more current-activated electromagnetic elements, the incubation can occur in a separation column, prior to activating the one or more electromagnetic elements. Preferably, however, incubation of a sample with magnetic beads comprising specific binding members occurs in a filtration chamber following filtration of the sample, and after conduits leading into and out of the filtration chamber have been closed. Where magnetic beads comprising secondary specific binding members are employed, optionally more than one incubation can be performed (for example, a first incubation of sample with a primary specific binding member, and a second incubation of sample with beads comprising a secondary specific binding member). Separation of undesirable components of a sample can be accomplished by magnetic forces that cause the electromagnetic beads that directly or indirectly bind the undesirable components. This can occur when the sample and magnetic beads are added to the column, or, in embodiments where one or more electromagnetic units are employed, by activating the electromagnetic units with a power supply. Noncaptured sample components can be removed from the separation column by fluid flow. Preferably, noncaptured sample components exit the column through a portal that engages a conduit.

Separation of Desirable Components

After filtering, a sample can optionally be directed by fluid flow to a separation chamber for the separation of rare cells.

In preferred aspects in which undesirable components of a debulked sample have been removed in a separation column, the debulked sample is preferably but optionally transferred to a second filtration chamber prior to being transferred to a separation chamber for separation rare cells of the sample. A second filtration chamber allows for further reduction of the volume of a sample, and also optionally allows for the addition of specific binding members that can be used in the separation of rare cells and mixing of one or more specific binding members with a sample. Transfer of a sample from a separation column to a separation chamber is by fluid flow through conduits that lead from a separation column to a second filtration chamber. A second filtration chamber preferably comprises at least one filter that comprises slots, and fluid flow through the chamber at a rate of between about one and about 500 milliliters per hour, more preferably between about two and about 100 milliliters per hour, and most preferably between about five and about fifty milliliters per hour drives the filtration of sample. In this way, the volume of a debulked sample from which undesirable components have been selectively removed can be further reduced. A second filtration chamber can comprise or engage one or more active chips. Active chips, such as acoustic chips or dielectrophoresis chips, can be used for mixing of the sample prior to, during, or after the filtration procedure.

A second filtration chamber can also optionally be used for the addition of one or more reagents that can be used for the separation of rare cells to a sample. After filtration of the sample, conduits that carry sample or sample components out of the chamber can be closed, and one or more conduits leading into the chamber can be used for the addition of one or more reagents, buffers, or solutions, such as, but not limited to, specific binding members that can bind rare cells. The one or more reagents, buffers, or solutions can be mixed in the closed-off separation chamber, for example, by activation of one or more acoustic elements or a plurality of electrodes on one or more active chips that can produce physical forces that can move components of the sample and thus provide a mixing function. In preferred aspects of the present invention, magnetic beads that are coated with at least one antibody that recognizes a rare cell are added to the sample in the filtration chamber. The magnetic beads are added via a conduit, and are mixed with the sample by activation of one or more active chips that are integral to or engage a second filtration chamber. The incubation of specific binding members with a sample can be from about five minutes to about two hours, preferably from about eight to about thirty minutes, in duration, and mixing can occur periodically or continuously throughout the incubation.

It is within the scope of the present invention to have a second filtration chamber that is not used for the addition and mixing of one or more reagents, solutions, or buffers with a sample. It is also within the scope of the present invention to have a chamber that precedes a separation chamber for the separation of rare cells that can be used for the addition and mixing of one or more reagents, solutions, or buffers with a sample, but that does not perform a filtering function. It is also within the scope of the present invention to have a sample transferred from a separation column to a separation chamber, without an intervening filtration or mixing chamber. In aspects where the methods are directed toward the separation of rare cells from a blood sample, however, the use of a second filtration chamber that is also used for the addition and mixing of one or more reagents with a sample is preferred.

Sample is transferred to a separation chamber by fluid flow. Preferably, a separation chamber for the separation of rare cells comprises or engages at least one active chip that can perform a separation. Such chips comprise functional elements that can, at least in part, generate physical forces that can be used to move or manipulate sample components from one area of a chamber to another area of a chamber. Preferred functional elements of a chip for manipulating sample components are electrodes and electromagnetic units. The forces used to translocate sample components on an active chip of the present invention can be dielectrophoretic forces, electromagnetic forces, traveling wave dielectrophoretic forces, or traveling wave electromagnetic forces. An active chip used for separating rare cells is preferably part of a chamber. The chamber can be of any suitable material and of any size and dimensions, but preferably a chamber that comprises an active chip used for separating rare cells from a sample (a "separation chamber") has a volumetric capacity of from about one microliter to ten milliliters, more preferably from about ten microliters to about one milliliter.

In some embodiments of the present inventions, the active chip is a dielectrophoresis or travelling wave dielectrophoresis chip that comprises electrodes. Such chips and their uses are described in U.S. application Ser. No. 09/973,629, entitled "An Integrated Biochip System for Sample Preparation and Analysis", filed Oct. 9, 2001; U.S. application Ser. No. 09/686,737, filed Oct. 10, 2000 entitled "Compositions and Methods for Separation of Moieties on Chips", U.S. application Ser. No. 09/636,104, filed Aug. 10, 2000, entitled "Methods for Manipulating Moieties in Microfluidic Systems"; and U.S. application Ser. No. 09/679,024, entitled "Apparatuses Containing Multiple Active Force Generating Elements and Uses Thereof" filed Oct. 4, 2000; all incorporated by reference. Rare cells can be separated from a sample of the present invention by, for example, their selective retention on a dielectrophoresis chip, and fluid flow can remove non-retained components of the sample.

In other preferred embodiments of the present invention, the active chip is an electromagnetic chip that comprises electromagnetic units, such as, for example, the electromagnetic chips described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". Electromagnetic chips can be used for separation by magnetophoresis or traveling wave electromagnetophoresis. In preferred embodiments, rare cells can be incubated, before or after addition to a chamber that comprises an electromagnetic chip, with magnetic beads comprising specific binding members that can directly or indirectly bind the rare cells. Preferably, in embodiments where rare cells are captured on an electromagnetic chip, the sample is mixed with the magnetic beads comprising a specific binding member in a mixing chamber. Preferably, a mixing chamber comprises an acoustic chip for the mixing of the sample and beads. The cells can be directed through conduits from the mixing chamber to the separating chamber. The rare cells can be separated from the fluid sample by magnetic capture on the surface of the active chip of the separation chamber, and other sample components can be washed away by fluid flow.

The methods of the present invention also include embodiments in which an active chip used for separation of rare cells is a multiple-force chip. For example, a multiple-force chip used for the separation of rare cells can comprise both electrodes and electromagnetic units. This can provide for the separation of more than one type of sample component. For example, magnetic capture can be used to isolated rare cells, while negative dielectrophoresis is used to remove undesirable cells from the chamber that comprises the multiple-force chip.

After the removal of undesirable sample components from the separation chamber, either through active physical forces such as negative dielectrophoresis or by fluid flow, the captured rare cells can be recovered by removing the physical force that causes them to adhere to the chip surface, and collecting the cells in a vessel using fluid flow.

Preferred Automated Systems for Enriching Rare Cells

Automated System Comprising at Least One Separation Chamber

A preferred embodiment of the present invention is an automated system for the separation of rare cells from a blood sample. The automated system comprises an inlet for the addition of a sample and means for providing fluid flow of a sample through the automated system, a filtration chamber that comprises an active chip that can be used for mixing the sample, a separation column that is positioned adjacent to at least one permanent magnet, a mixing chamber that comprises acoustic elements for the mixing of a sample with one or more preparations of magnetic beads comprising at least one specific binding member that can bind rare cells, and a separation chamber that comprises an active chip having electromagnetic units for the capture of rare cells, and, preferably, a collection vessel for the collection of rare cells.

A blood sample, such as but not limited to a maternal blood sample, can be added to the automated system via the sample inlet. A blood sample is preferably from one to fifty milliliters in volume. The sample is transported into a filtration chamber that has ten milliliter capacity by fluid flow through tygon tubing through a port. Magnetic beads that are coated with an antibody that binds to white blood cells are added to the filtration chamber after the filtration procedure. Continuous positive pressure through the port provides fluid flow through the chamber, which has two opposite walls that comprise multiple slots of a slot width of about two to about four microns and a length of from about twenty to about four hundred microns, that can allow the passage of red blood cells, but not nucleated red blood cells or white blood cells. Cells and other sample components of the sample are mixed by activating the acoustic chip that forms the lower wall of the chamber with periodic pulses. Vibrational energy from the acoustic units dislodges cells that accumulate at the slots and block the passage of sample fluid and red blood cells. Optionally, the filter surfaces may have incorporated microelectrodes which can generate dielectrophoretic forces to dislodges cells that accumulate at the slots and block the passage of sample fluid and red blood cells. After the filtration procedure, magnetic beads that are coated with an antibody that binds to white blood cells are added to the filtration chamber. The fluid sample in the chamber is then incubated with magnetic beads. The magnetic beads are bound to antibodies that specifically bind to white blood cells. After an incubation of about ten to thirty minutes, with intermittent acoustic mixing, the sample is transported by fluid flow to a separation column of a capacity of about three milliliters that is positioned adjacent to two permanent magnets.

As the blood sample flows through the separation column, white blood cells that bind the magnetic beads adhere to the column proximal to the magnets. Unbound sample components flow through the separation column and out through tubing to a mixing chamber.

The mixing chamber (of approximately 1 milliliter capacity) comprises an acoustic chip having at least one acoustic element that can be activated by a power source. Magnetic beads that are coated with an antibody that recognizes nucleated red blood cells is added through separated tubing, and the sample and magnetic beads are mixed by activating the acoustic units. The sample is then transported, by positive pressure, to an electromagnetic chip in a 100 microliter (up to 1 ml) separation chamber that captures the nucleated red blood cells using electromagnetic units. After turning off the electromagnetic units, nucleated red blood cells can be collected by fluid flow transport through tubing to a collection vesicle. Alternatively, the sample from the mixing chamber is then transported, by positive pressure, to 100 microliter (up to 1 ml) separation chamber that captures the nucleated red blood cells using permanent magnets that are reversibly engaged to the chamber. After capturing the nucleated red blood cells, the permanent magnets are taken away from the chamber, so that nucleated red blood cells can be collected by fluid flow transport through tubing to a collection vesicle.

Automated System Comprising Red Blood Cell Sedimentation

Another preferred automated system of the present invention is a system that processes a blood sample, in which red blood cells are sedimented from the blood sample prior to filtration. One, or preferably, a plurality of blood samples provided in tubes are placed by the user into a rack that is a part of the automated system. Preferably the rack is automatically transported (such as on a retracting platform, or by moving along a track, moved by a robotic arm, etc.) or placed by the user in a housing that comprises the automatic system. Preferably the rack is robotically positioned so that solutions can be dispensed into the tubes by the automated system. For example, the rack can be positioned beneath a fluid dispensing system. A solution that selectively sediments red blood cells, such as, preferably, a combined solution of the present invention that selectively sediments red blood cells and comprises magnetic beads coated with a specific binding member that binds to white blood cells, can be automatically dispensed into the tubes. Optionally but preferably, the automated system can have a fluid sensing system (such as one based on optical sensing) that can determine the volume of a blood sample provided in a tube in the rack, and calculate and add an appropriate volume of sedimenting solution to the tube that contains the blood sample.

For example, a light source, such as but not limited to a light bulb or LED, can interrogate the tube or column of sample. The transmittance, absorption or reflectance of the incident light can be measured by appropriate structures, such as CCDs or photomultipliers. Appropriate wavelengths for optical sensing can be readily determined. Because layers of the sample column with a high density of RBCs are optically dense and do not transmit light well, the interface between high and low RBC densities can be determined by such optical methods. The instrument can localize such an interface or zone and calculate the volume in the tube by the height of the column. This can be done by using light sources and detection devices that are mobile and that either continuously or in graduated fashion scan the length (or a portion of the length) of the tube or column containing the sample, or by having multiple light sources and multiple detectors that are oriented vertically and can simultaneously detect optical density along a tube or column and thereby determine the volume of the sample (or subfraction thereof). The automated system then calculates the amount of combined solution to add to each sample tube, and adds the appropriate amounts using an automated fluid dispensing system.

The rack holding the tubes can rotate automatically such that the sample tubes are rocked to mix the sample and combined solution. Mixing can occur for a period of time ranging from about ten to about sixty minutes, for example, for about 30 minutes. Following mixing, the rack holds the tubes upright and a frame comprising a plurality of magnets can be positioned such that the magnets are held against the tubes. (Alternatively, the rack can move to position the tubes against the magnets.) During a settling period of from ten to sixty minutes, for example, about 30 minutes, a supernatant is removed from each tube using the automatic fluid uptake/dispensing system. Sedimented cell and cells collected by magnetic forces, such as, in preferred embodiments, the majority of red blood cells and undesirable components, such as white blood cells, of the sample, are left in the sample tube.

The fluid sensing device is used to determine the amount of supernatant in the tube, and the information is used to collect the appropriate amount of sample from each tube. For example, the interface between high and low RBC densities can be determined by the optical methods described. The instrument can localize the interface or zone between high and low RBC densities and calculate the volume of supernatant in the tube by the height of the column. For example, by identifying the interface zone, a sample removal structure, such as a needle coupled to a negative pressure device, can be localized above the interface or zone and a sample low in RBCs can be drawn off and further processed. (Alternatively, such optical methods can be used to determine the height of the RBC region, and a sample removal structure such as a needle and negative pressure device can be localized such that the orifice of the needle is at or near the bottom of the column and the appropriate volume removed to extract the RBC rich layer, leaving the supernatant to be collected separately for transfer to a filtration chamber.)

Each removed supernatant is transferred to a loading reservoir that connects to a filtration chamber through a port that comprises a valve. When the supernatant is loaded, the valve is closed and the filtration chamber contains a buffer compatible with blood cells, such as PBE.

Filtration commences with the opening of 1) the valve leading to the loading reservoir (valve A in FIG. 14), 2) the valve leading to the negative pressure system that allows effluent to leave the post-filtration subchamber (valve B in FIG. 14), and the application of negative pressure from the automated fluid flow system. Filtration allows filterable components (such as liquid, soluble components, and residual red blood cells) to flow through the filter and exit the post-filtration subchamber, while nonfilterable components, including the rare cells to be enriched, are retained in the antechamber. The rate of filtration can be from about 1 to about 1000 milliliters per hour, preferably between about 5 and about 50 milliliters per hour. The filtration process can take from about ten minutes to over eight hours, depending on the sample volume being filtered and the flow rate. Preferably, for a blood sample with a starting volume of 40 milliliters, filtration will take approximately four hours. Additional wash buffer, such as for example, PBS, is washed through the filtration chamber after the blood sample has passed from the loading reservoir into the filtration chamber.

A backwash is preferably performed in which the valve leading out of the post-filtration chamber (valve B in FIG. 14) closed and valve C leading to a syringe pump is opened. A blood cell compatible buffer (such as PBS) is pushed by the syringe pump "backwards" from the post-filtration chamber up to the antechamber. This dislodges the retained cells in the antechamber from the surface of the filter and suspends them in buffer solution for more efficient collection. In some embodiments of the present invention, cell are collected by pushing buffer through open valve C such that suspended rare cells exit the antechamber through valve D (see FIG. 14). In other embodiments, such as that shown in FIG. 16, the filtration chamber is washed and then the filtration unit is rotated so that valve A engages a collection vessel. Wash buffer pumped through valve C then causes the enriched rare cells to flow into the collection vessel.

Additional Steps

Various elements of the embodiments presented herein can be combined in any way to create further embodiments of automated systems and methods of using automated systems of the present invention. The present invention also includes automated systems having functions in addition to those specifically disclosed, and methods of using automated systems having additional steps, such as additional debulking and separation steps.

The present invention also includes methods of using automated systems in combination with other automated or nonautomated systems and methods for enrichment, separation, or analysis of rare cells.

EXAMPLES

Example 1

Isolation of Fetal Nucleated Red Blood Cells from a Maternal Blood Sample

Preparation of Magnetic Beads

Magnetic beads for the capture of nucleated red blood cells were prepared during the processing (centrifugation) of collected blood. For each 1 milliliter of anticipated final cell preparation, twenty microliters of commercially available streptavidin magnetic beads (Bang's Laboratories) were used, to give a ratio of 10 to 30 beads per target cell, or 5 to 20 micrograms of iron per milliliter of solution. The beads were diluted ten-fold with PBE (PBS containing 0.5% BSA and 5 mM EDTA) and pipeted into a 12×75 mm polypropylene tube. The beads were collected with a magnet placed along the side of the tube for ten minutes. The supernatant was removed, and the washing process was repeated twice. The beads were finally resuspended in ten times their original volume of PBE.

Preparation of DEP Chip

During antibody enrichment of nucleated red blood cells (below) a parallel electrode dielectrophoresis (DEP) 1 cm by 1 cm chip made of 600 micron thick silicon, and having 50 micron width by 50 micron gap interdigitated electrodes, was coated with surface coating buffer (PBE with 0.05% lysozyme and 5% human serum) and incubated for twenty minutes. The chip was encased in a polystyrene chamber, of dimensions 6.4 millimeter by 4.1 millimeter.

Density Gradient Centrifugation of Blood Samples

Twenty to forty milliliter post-surgery blood samples from women who had undergone clinical abortion at the eighth to the eleventh week of pregnancy were collected in tubes rinsed with PBE (PBS containing 0.5% BSA and 5 mM EDTA). Between one and twenty-four hours after collection, blood samples were diluted with an equal volume of PBE and layered on top of ficoll ("Histopaque") gradients. The gradients were made in 50 mL centrifuge tubes precoated with PBE by overlaying 7.5 milliliters of Histopaque-1.107 with 7.5 milliliters of Histopaque-1.077. (Histopaque 1.107 is made by mixing 7 parts Histopaque-1.119 and 3 parts Histopaque-1.107).

The gradients were centrifuged in a tabletop centrifuge for 30 minutes at room temperature at 470×g with the brake off.

After centrifugation, the tubes were removed from the centrifuge and everything above the Histopaque-1.077 layer was aspirated off to remove serum and platelets. The entire Hisotpaque-1.077 and 1.107 layers from each gradient were collected and put in two precoated 50 milliliter centrifuge tubes. The tubes were filled with PBE and centrifuged for 10 minutes at 1200–1500 rpm. The supernatants were removed, and the pellets were washed once (10 minutes at 1200–1500 rpm) to remove residual Histopaque. The pellets were gently resuspended and cell counts were performed to obtain an estimate of the cell number. The number of cells obtained after gradient debulking of a post-surgery blood sample ranged between $3.75 \times 10^6$ and $1.13 \times 10^7$ per milliliter of collected blood sample, with an average number of $7.33 \times 10^6$ cells recovered per milliliter of collected samples (average of eight samples). The cells were resuspended in PBE to give a concentration of 100 million cells per milliliter.

Antibody Enrichment of Nucleated Red Blood Cells from Blood Samples

For each milliliter of diluted cells, 0.1 microgram of biotinylated anti-CD71 antibodies (Leinco Technologies I)

diluted 1:1 in PBE were added to a 50 milliliter tube containing the cells. The antibodies were incubated with the cells for 15 minutes rocking at room temperature. The tube was then filled with PBE, mixed, and centrifuged 10 minutes at 1500 rpm. The supernatant was removed. The cells were resuspended to a final volume of 50 milliliters in PBE. The tube was again filled with PBE and centrifuged as before. The final pellet was resuspended in a volume of PBE equal to that of the original blood sample volume, minus that of the final preparation of magnetic beads (above).

The cells from a collected sample (approximately one to four milliliters at a cell concentration of from between $10^7$ and $10^8$ per milliliter) were transferred to a 4 milliliter tube. The washed streptavidin-magnetic beads were added to the tube and the cells and antibodies were incubated for ten minutes at room temperature with rotation. The tube was then placed in an Immunicon (Huntington Valley, Pa.) magnetic separator for ten minutes. The supernatant was then removed using a long needle connected to a five milliliter syringe, and then the tube was removed from the separator. The cells were resuspended om three milliliters of PBE by pipeting up and down, and the tube was again placed in the Immunicon magnetic separator for five minutes. The supernatant was removed as before, the tube was removed from the separator, and the cells were resuspended in PBE to a concentration of approximately one million cells per five microliters. Aliquots of the CD71-selected cells were removed for cell counts, and for staining with BWG and fetal and embryonic hemoglobin antibodies (see below). After antibody enrichment of nucleated red blood cells using the CD71 antibody, the number of cells recovered ranged from $2.5 \times 10^4$ to $1.7 \times 10^5$ cells per ml of original collected sample. The number of nucleated red blood cells, as estimated from Benzidine-Wright-Giemsa staining of aliquots, ranged from 2 to 500 per milliliter of sample, and of two samples stained for fetal and embryonic hemoglobin, the estimated number of fetal nucleated red blood cells was 1.3 and 13 per ml of original collected sample.

Dielectrophoretic Separation of Nucleated Red Blood Cells

A 15 Mhz and 5 Vp-p AC signal was applied to a DEP chip that has been coated with PBE containing 0.05% lysozyme and 5% human serum to prevent nonspecific cell adhesion and equilibrated in sucrose solution. Five microliters of cells were added to twenty microliters of sucrose buffer (250 millimolar sucrose) and then the sample was loaded using a syringe connected to tygon tubing that leads to the chamber with a flow rate of 1.5–2 milliliter per hour. When the cells reached the chamber, the flow rate was changed to 0.2 milliliters per hour. After washing with 0.5 to 1 milliliter of sucrose buffer, the syringe was removed and a new syringe was added. The AC signal was turned off, and 1 milliliter of PBE was then added through the new syringe to allow the captured cells to flow out of the chamber into a two milliliter centrifuge tube. The cells were centrifuged at 1500 rpm for ten minutes. An aliquot of the cells was counted, and the cells were resuspended in a volume of one million cells per milliliter of PBE. Aliquots of dielectrophoretically separated cells were stained with either a Benzidine-Wright-Giemsa stain or an antibody to fetal hemoglobin, and with fluorescent nucleotide probes.

Benzidine-Wright-Giemsa Staining

Between 50,000 and 200,000 pooled WBC-depleted cells were spun onto coated slides and fixed for a histological stain to detect hemoglobin as follows: the slides were treated with absolute methanol for five minutes, 1% benzidine base (3,3'dimethoxy-benzidine) in methanol for 1.5 minutes, and then a solution of 3.75 milliliters of 30% hydrogen peroxide in 150 milliliters of 50% ethanol for 1.5 minutes. The slides were rinsed twice in distilled water, and then stained with a Wright-Giemsa stain (3 ml of Wright solution and 9 ml of Giemsa in 150 ml water) stain for ten minutes. The slides were washed three times in distilled water and allowed to dry.

Fetal Hemoglobin Antibody Staining

One hundred microliter aliquots of suspended separated cells were loaded onto slides precoated with 50 microliters of PBE. The slides were centrifuged at 600 rpm for 2 minutes, and then the slides were air dried for one to two minutes. The slides were fixed in Streck Tissue Fixative for 10 minutes, post-fixed in 2% formaldehyde/Streck for 4 minutes, and then washed in distilled water for a few seconds, in PBS twice for 6 minutes, in distilled water for five minutes, and then dried at 37 degrees C. The slides were used immediately or stored at −20 degrees C.

The slides were warmed to room temperature, when necessary, for 30–60 minutes, and then cell spots were isolated using a PAP-PEN (minimum size). The slide was blocked with 10% normal mouse serum/TBST for 30 minutes at room temperature, and then incubated with fifty microliters of diluted antibodies (mouse anti-hemoglobin gamma-fluorescein diluted 1:1000; mouse anti-hemoglobin epsilon-fluorescein diluted 1:1000) at room temperature for 30 minutes. The slides were washed 4 times with TBST (5 minutes each with or without gentle shaking).

Fetal Hemoglobin Staining and Using X/Y Chromosome Probes

One hundred microliter aliquots of suspended separated cells were loaded onto slides precoated with 50 microliters of PBE. The slides were centrifuged at 600 rpm for 2 minutes, and then the slides were air dried for one to two minutes. The slides were fixed using standard procedures, and then washed in distilled water for a few seconds, in PBS twice for 6 minutes, in distilled water for five minutes, and then dried at 37 degrees C. The slides were used immediately or stored at −20 degrees C.

The slides were warmed to room temperature, when necessary, for 30–60 minutes, and then cell spots were isolated using a PAP-PEN (minimum size). The slide was blocked with 10% normal mouse serum/TBST for 30 minutes at room temperature, and then incubated with fifty microliters of diluted antibodies (mouse anti-hemoglobin gamma-fluorescein diluted 1:1000; mouse anti-hemoglobin epsilon-fluorescein diluted 1:1000) at room temperature for 30 minutes. The slides were washed 4 times with TBST (5 minutes each with or without gentle shaking).

In some cases, hemoglobin staining was checked prior to proceeding with FISH. The slides were air dried and mounted with 50% Glycerol/PBS and a coverslip. Then the coverslip was flipped off and the slide was rinsed twice in TBST for 5 minutes each and twice in $dH_2O$ for 1 minute. The slide was dehydrated in 70%, 95% and 100% ethanol for 2 minutes each and air dried.

If needed, cell spots on the slides were re-isolated with the PAP-PEN (minimum size). Ten microliters of a mixture of X and Y chromosome probes were added onto each cell spot, and the spots were covered with coverslips. A mixture of X and Y probe were added and hybridization was performed using methods known in the art. The coverslips were floated off, or gently nudged off. The slides were then washed in 2×SSC for 5 minutes. The slides were incubated with 1 microgram of Hoechst 33342 per ml of PBE for 5 min in the dark. The slides were rinsed in TBST for 5 minutes, then rinsed in $dH_2O$ twice for 1 minute each and air dried. The slides were mounted with Vectashield mounting medium and sealed with nail polish.

Figure 12:
FIG. 12 shows FISH analysis of nucleated red blood cells isolated using the methods of the present invention using a Y chromosome marker that has detected a male fetal cell in a maternal blood sample.

Blood samples subjected to density gradient centrifugation, magnetic separation, and dielectrophoretic separation that were analyzed by FISH showed that nucleated red blood cells of fetal origin (immunologically identified with antibodies to fetal and embryonic hemoglobin and having Hoescht stained nuclei) were isolated from maternal blood samples. Some samples showed X and Y chromosome staining of cells, indicative of a male fetal cell (FIG. 12).

Example 2

Comparison of Commercially Available Antibodies for the Selective Removal of White Blood Cells from Maternal Blood Samples Preparation of Magnetic Beads Preparation of the 0.8 micron diameter magnetic beads was performed during the processing (centrifugation) of collected blood. For each 1 milliliter of anticipated final cell preparation, fifteen microliters of streptavidin-coated magnetic beads, or approximately ten to thirty beads per target cell, were used. The beads were diluted ten-fold with PBE (PBS containing 0.5% BSA and 5 mM EDTA) and pipeted into a 12×75 mm polypropylene tube. The beads were collected with a magnet placed along the side of the tube for ten minutes. The supernatant was removed, and the washing process was repeated twice.

Density Gradient Centrifugation of Blood Samples

Twenty to forty milliliter post-surgery peripheral blood samples from women who had undergone clinical abortion at the sixth to the sixteenth week of pregnancy were collected in tubes rinsed with PBE (PBS containing 0.5% BSA and 5 mM EDTA). In some cases, the maternal blood samples also contained cells dissected from fetal liver. The samples were debulked on a Histopaque density gradient as described in Example 1.

After centrifugation, the tubes were removed from the centrifuge and everything above the Hisopaque-1.077 layer was aspirated off to remove serum. The entire Hisotpaque-1.077 layer and 1.107 layer were collected and put into two precoated 50 milliliter centrifuge tubes. The tubes were filled with PBE and centrifuged for 10 minutes at 1500 rpm. The supernatant was removed, and the pellet was washed twice (10 minutes at 1500 rpm) to remove residual Histopaque. The pellet was gently resuspended and a cell count was performed to obtain an estimate of the cell number. The cells were resuspended in PBE to give a concentration of 1–10 million cells per milliliter.

Antibody Depletion of White Blood Cells from Maternal Blood Samples

A recommended amount (from 0.01 to 10 micrograms/ml) of biotinylated antibodies (diluted 1:1 in PBE) obtained commercially were added per milliliter of sample in a fifty milliliter tube. The antibodies and cells were incubated for fifteen minutes at room temperature on a rocker. The tube was then filled with PBE, mixed, and spun for ten minutes at 1500 rpm. The supernatant was removed and the cells were washed once more. The cells were then resuspended in a volume of PBE equal to that of the original blood sample, minus the volume of the washed bead preparation (above). The washed streptavidin magnetic beads were added to the cell preparation (about 10 to 30 beads per cell) and incubated for fifteen minutes with rotation at room temperature.

The tube containing the cells and magnetic beads was placed against a magnet in a Dynal magnet stand for ten minutes. The supernatant was collected and put into a second tube-that was then placed in the magnet stand. After a second ten minute interval, the twice-depleted supernatant was put into a tube for the antibody selection step (see below). The beads from the first depletion step were resuspended in PBE and put back into the first magnet and incubated for ten minutes. The cells from the second magnet were resuspended in PBE, and placed in the Immunicon magnet for ten minutes. The supernatant was removed and subjected to another selection step in an Immunicon magnet. The final (second cell resuspension, twice-depleted) supernatant was then combined with the first cell resuspension twice-depleted supernatant now referred to as the pooled WBC-depleted cells.

Between 100,000 and 200,000 pooled WBC-depleted cells were spun onto coated slides and fixed for hemoglobin staining as follows: the slides were treated with absolute methanol for five minutes, 1% benzidine base (3,3'dimethoxy-benzidine) in methanol for 1.5 minutes, and then a solution of 3.75 milliliters of 30% hydrogen peroxide in 150 milliliters of 50% ethanol for 1.5 minutes. The slides were rinsed twice in distilled water, and then stained with Wright-Giemsa (3 ml of Wright solution and 9 ml of Giemsa in 150 ml water) stain for ten minutes. The slides were then washed three times in distilled water and allowed to dry.

Microscopic examination of the slides revealed the following results using several antibodies:

TABLE 1

Efficacy of Different Antibodies in Depleting WBCs from Maternal Blood Samples

| CD antibody | Cells | Antibody conc. (ugs/ml) | Total Cells after separation | WBCs after separation | nRBC recovered (%) |
|---|---|---|---|---|---|
| 3 | $10^6$ | 0.1 | $6.5 \times 10^5$ | ND | 57 |
|   | $10^6$ | 0.01 | $1.1 \times 10^6$ | ND | ND |
| 11b | $10^6$ | 0.1 | $2.2 \times 10^5$ | ND | 19 |
|   | $10^6$ | 0.01 | $9.3 \times 10^5$ | ND | ND |
| 14 | $10^6$ | 0.1 | $6.6 \times 10^5$ | ND | 66 |
|   | $10^6$ | 0.01 | $7.7 \times 10^5$ | ND | ND |
| 31 | $10^6$ | 0.1 | $8.1 \times 10^5$ | ND | ND |
|   | $10^6$ | 0.01 | $8.7 \times 10^5$ | ND | ND |
| 45 | $10^6$ | 0.1 | $4.6 \times 10^5$ | ND | 38 |
|   | $10^6$ | 0.01 | $9.3 \times 10^5$ | ND | ND |
| 50 | $10^6$ | 0.1 | $2.4 \times 10^5$ | ND | 86 |
|   | $10^6$ | 0.01 | $4.4 \times 10^5$ | ND | 86 |
| Mouse IgG | $10^6$ | 0.1 | $8.9 \times 10^5$ | ND | 59 |
|   | $10^6$ | 0.01 | $8.9 \times 10^5$ | ND | ND |
| 3 | $10^7$ | 0.1 | $5.5 \times 10^6$ | ND | ND |

TABLE 1-continued

Efficacy of Different Antibodies in Depleting WBCs from Maternal Blood Samples

| CD antibody | Cells | Antibody conc. (ugs/ml) | Total Cells after separation | WBCs after separation | nRBC recovered (%) |
|---|---|---|---|---|---|
|  | $10^7$ | 0.01 | $3.7 \times 10^6$ | ND | ND |
| 11b | $10^7$ | 0.1 | $2.1 \times 10^6$ | ND | ND |
|  | $10^7$ | 0.01 | $3.0 \times 10^6$ | ND | ND |
| 45 | $10^7$ | 0.1 | $4.1 \times 10^6$ | ND | ND |
|  | $10^7$ | 0.01 | $3.7 \times 10^6$ | ND | ND |
| 50 | $10^7$ | 0.1 | $1.7 \times 10^6$ | ND | ND |
|  | $10^7$ | 0.01 | $2.5 \times 10^6$ | ND | ND |
| Mouse IgG | $10^7$ | 0.1 | $5.0 \times 10^6$ | ND | ND |
|  | $10^7$ | 0.01 | $5.1 \times 10^6$ | ND | ND |
| 3 + 50 | $10^6$ | 0.10 each | $5.0 \times 10^5$ | $6.0 \times 10^4$ | 59.1 |
|  | $10^6$ | 0.01 each | $2.4 \times 10^5$ | $1.2 \times 10^5$ | 76.5 |
| 14 + 50 | $10^6$ | 0.10 each | $1.7 \times 10^5$ | $5.1 \times 10^4$ | 48.7 |
|  | $10^6$ | 0.01 each | $5.1 \times 10^5$ | $3.4 \times 10^5$ | 77.5 |
| 3 + 14 + 50 | $10^6$ | 0.10 each | $4.1 \times 10^5$ | $7.6 \times 10^4$ | 55.6 |
|  | $10^6$ | 0.01 each | $3.7 \times 10^5$ | $2.4 \times 10^5$ | 70.5 |
| Mouse IgG | $10^6$ | 0.10 | $8 \times 10^5$ | $7.27 \times 10^5$ | 62.1 |
|  | $10^6$ | 0.01 | $8.9 \times 10^5$ | ND | ND |
| 69 (+50) | $10^6$ | 0.01 (0.1) | $2.2 \times 10^5$ | $2.2 \times 10^4$ | 50.6 |
|  | $10^6$ | 0.03 (0.1) | $1.8 \times 10^5$ | $1.8 \times 10^4$ | 44.6 |
|  | $10^6$ | 0.10 (0.1) | $2.2 \times 10^5$ | $2.2 \times 10^4$ | 50.6 |
| 166 (+150) | $10^6$ | 0.01 (0.1) | $2.1 \times 10^5$ | $2.1 \times 10^4$ | 48.2 |
|  | $10^6$ | 0.03 (0.1) | $2.5 \times 10^5$ | ND | ND |
|  | $10^6$ | 0.10 (0.1) | $1.7 \times 10^5$ | ND | ND |
| 81 | $10^6$ | 0.01 | $2.9 \times 10^5$ | $2.6 \times 10^5$ | 78.3 |
|  | $10^6$ | 0.03 | $4.2 \times 10^5$ | $3.68 \times 10^5$ | 27.7 |
|  | $10^6$ | 0.06 | $4.9 \times 10^5$ | $3.92 \times 10^5$ | 53 |
|  | $10^6$ | 0.10 | $3.1 \times 10^5$ | $2.33 \times 10^5$ | 44.6 |
|  | $10^6$ | 0.30 | $2.9 \times 10^5$ | $2.2 \times 10^5$ | 71.1 |
| 102 | $10^6$ | 0.01 | $5.1 \times 10^5$ | $4.8 \times 10^5$ | 0 |
|  | $10^6$ | 0.03 | $5.1 \times 10^5$ | $4.8 \times 10^5$ | 37.4 |
|  | $10^6$ | 0.10 | $6.0 \times 10^5$ | $5.5 \times 10^5$ | 109 |
| 63 | $10^6$ | 0.01 | $5.8 \times 10^5$ | $5.0 \times 10^5$ | 18.1 |
|  | $10^6$ | 0.03 | $5.6 \times 10^5$ | $4.7 \times 10^5$ | 43.4 |
|  | $10^6$ | 0.10 | $7.0 \times 10^5$ | $5.3 \times 10^5$ | 59.0 |
| 84 | $10^6$ | 0.01 | $5.4 \times 10^5$ | $4.8 \times 10^5$ | 32.5 |
|  | $10^6$ | 0.03 | $5.4 \times 10^5$ | $4.1 \times 10^5$ | 28.9 |
|  | $10^6$ | 0.10 | $7.2 \times 10^5$ | $5.4 \times 10^5$ | 69.9 |
| 17 (+50) | $10^6$ | 0.01 (0.01) | $3.5 \times 10^5$ | $3.18 \times 10^5$ | 12.9 |
|  | $10^6$ | 0.03 (0.01) | $3.9 \times 10^5$ | $3.55 \times 10^5$ | 18.4 |
|  | $10^6$ | 0.01 (0.03) | $2.5 \times 10^5$ | $1.88 \times 10^5$ | 46.0 |
|  | $10^6$ | 0.03 (0.03) | $2.2 \times 10^5$ | $2.00 \times 10^5$ | 31.3 |
| 53 (+50) | $10^6$ | 0.01 (0.01) | $3.7 \times 10^5$ | $3.36 \times 10^5$ | 47.9 |
|  | $10^6$ | 0.03 (0.01) | $3.8 \times 10^5$ | $3.45 \times 10^5$ | 68.1 |
|  | $10^6$ | 0.01 (0.03) | $2.6 \times 10^5$ | $2.17 \times 10^5$ | 44.2 |
|  | $10^6$ | 0.03 (0.03) | $2.6 \times 10^5$ | $2.08 \times 10^5$ | 46.0 |

(Mouse IgG is a mouse antibody that is a control for non-specific binding. The rest of the antibodies are antibodies to specific antigens.)

Example 3

Isolation of Fetal Nucleated Red Blood Cells from a Blood Sample

Preparation of Magnetic Beads

Bead preparation was performed during the centrifugation of collected blood. For each 1 milliliter of anticipated final cell preparation, twenty to forty microliters of streptavidin-coated 0.8 micron magnetic beads, or approximately ten beads per target cell, were used. The beads were diluted ten-fold with PBE and pipeted into a 12×75 mm polypropylene tube. The beads were collected with a magnet placed along the side of the tube for ten minutes. The supernatant was removed, and the process was repeated twice.

Density Gradient Centrifugation of Blood Samples

A ten milliliter peripheral blood samples from a pregnant woman was collected in a tube rinsed with PBE (PBS containing 0.5% BSA and 5 mM EDTA). Approximately four thousand fetal liver cells that include nucleated red blood cells, dissected from an eighteen week gestational age male human abortus, were added to the maternal blood sample. The blood sample was diluted with an equal volume of PBE and layered on top of ficoll ("Histopaque") gradients. The gradients were made in 50 mL centrifuge tubes precoated with PBE by overlaying 7.5 milliliters of Histopaque-1.107 with 7.5 milliliters of Histopaque-1.077. (Histopaque 1.107 is made by mixing 7 parts Histopaque-1.119 and 3 parts Histopaque-1.107).

The gradients were centrifuged in a tabletop centrifuge for 30 minutes at room temperature at 470×g with the brake off.

After centrifugation, the tubes were removed from the centrifuge and everything above the Hisopaque-1.077 layer was aspirated off to remove serum. The entire Histopaque-1.077 layer was collected and put in two precoated 50 milliliter centrifuge tubes. The tubes were filled with PBE and centrifuged for 10 minutes at 1500 rpm. The supernatant was removed, and the pellet was washed once (10 minutes at 1500 rpm) to remove residual Histopaque. The pellet was gently resuspended and a cell count was performed to obtain an estimate of the cell number. The cells were resuspended in PBE to give a concentration of 100 million cells per milliliter.

Antibody Depletion of White Blood Cells from Maternal Blood Samples

One microgram of biotinylated CD-50 antibodies diluted 1:1 in PBE) were added per milliliter of sample in a fifty milliliter tube. The antibodies and cells were incubated for fifteen minutes at room temperature on a rocker. The tube was then filled with PBE, mixed, and spun for ten minutes at 1500 rpm. The supernatant was removed and the cells were washed once more. The cells were resuspended in a volume of PBE to a volume equal to that of the original blood sample, minus the volume of the washed bead preparation (above). The washed streptavidin magnetic beads were added to the cell preparation and incubated for fifteen minutes with rotation at room temperature.

The tube containing the cells and magnetic beads were placed in the Immunicon 50 milliliter tube magnet (cat# HMS) for ten minutes. The supernatant was collected and put into a second tube that was then placed in another Immunicon 50 milliliter immunicon tube magnet. After a second ten minute interval, the twice-depleted supernatant was put into a tube for the antibody selection step (see below). The beads from the first depletion step were resuspended in PBE and put back into the first magnet and incubated for ten minutes. The cells from the second magnet were resuspended in PBE, and placed in the Immunicon magnet for ten minutes. The supernatant was removed and subjected to another selection step in an Immunicon magnet. The final (second cell resuspension twice-depleted) supernatant was then combined with the first cell resuspension twice-depleted supernatant now referred to as the pooled CD50− cells.

Nucleated Red Blood Cell Enrichment

The volume of the pooled CD50− cells was adjusted to a concentration of 10 million cells per milliliter in a 50 milliliter tube using PBE. 0.1 microgram of biotinylated anti-CD71 antibodies were added (after 1:1 dilution in PBE) for every milliliter of resuspended cells and the cells and antibodies were incubated for fifteen minutes at room temperature on a rocker. The tube was then filled with PBE, mixed, and then centrifuged for ten minutes at 1500 rpm. The supernatant was removed and the tube was again filled with PBE, mixed, and centrifuged as before. The cells were then transferred to a microfuge tube and the washed magnetic beads (see above) were added to the cells. The cells and beads were incubated for fifteen minutes with rotation. The tube was then place into a small microfuge tube magnet stand (Dynal, catalog number MPC-E) for ten minutes. The supernatant was removed. The tube containing the CD71 +cells was removed from the magnet stand.

In an alternative method for selecting nucleated red blood cells, the volume of the pooled CD50− cells was adjusted to a concentration of 10 million cells per milliliter using PBE and placed in a microfuge tube. The washed streptavidin-coated magnetic beads (see above) were incubated in a microfuge tube with one microgram of biotinylated CD71 at room temperature for fifteen to thirty minutes. The beads were captured using a Dynal magnet stand and then washed and captured two more times using one milliliter of PBE per wash. The captured CD71 antibody-coated beads were then added to the CD50− cells and incubated at room temperature for ten to thirty minutes with rotation. The tube was then placed in the magnet stand for ten minutes to capture CD71+ cells. The supernatant was removed, and the tube containing the cells is removed from the magnet stand.

The estimated recovery of nucleated red blood cells, as estimated by Wright-Giemsa staining, was 86%.

Example 4

Use of an Automated System for the Isolation of Fetal Nucleated Red Blood Cells from a Maternal Blood Sample Preparation of Magnetic Beads For each 1 milliliter of anticipated final cell preparation, twenty microliters of streptavidin-coated magnetic beads, or approximately ten to thirty beads per target cell, are used. The beads are diluted ten-fold with PBE (PBS containing 0.5% BSA and 5 mM EDTA) and pipeted into a 12×75 mm polypropylene tube. The beads are collected with a magnet placed along the side of the tube for ten minutes. The supernatant is removed, and the process is repeated twice. The beads are finally resuspended in ten times their original volume.

Automated Separation of Nucleated Red Blood Cells from the Sample

A 20 to 40 milliliter blood sample is collected in tubes rinsed with PBE from a pregnant woman at the sixth to sixteenth week of pregnancy. Up to twenty four hours after collection, the maternal blood sample is diluted with an equal volume of PBE (PBS containing 5 mM EDTA) and pipeted into a reservoir of an automated chip-based blood analysis system, such as that depicted in FIG. 6. A syringe pump is used to provide fluid flow at a constant rate of between about ten and about fifty milliliters per hour from the reservoir through conduits leading to an incoming port of a filtration chamber. The filtration chamber also has a reagent portal, outgoing ("waste") ports at two opposite ends of the chip, and a connecting portal. A conduit extends from the connecting portal to a second chamber that comprises a chip. The chamber comprises two filters, one at each end of the chamber, that comprises a plurality of slots that have a length of between about fifty and about two hundred microns and a width of about two to four microns, such that most red blood cells are able to flow through the channels and out of the chamber through the outgoing ports, whereas nucleated fetal red blood cells are retained in the chamber. The chamber and conduits that connect to the chamber are part of a molded plastic cartridge. The cartridge can engage acoustic chips that can exert acoustic forces within the filtration chamber.

Fluid flow generated by suction (negative pressure) of a syringe pump provides fluid flow of the sample through the filtration chamber. The acoustic chips that engage the filtration chamber are activated in intermittent AC pulses throughout the filtration (approximately 0.5 to two hours), providing mixing of the sample and dislodging the cells that accumulate at the slots and block the passage of sample fluid and red blood cells.

Optionally, the filter surfaces may have incorporated microelectrodes which can generate dielectrophoretic forces that act in combination with acoustic forces, or separately, to dislodges cells that accumulate at the slots and block the passage of sample fluid and red blood cells.

After filtration, ports of the chamber are closed, except for a reagent port through which antibody coated beads are added. After addition of antibody coated beads and closing of all chamber ports, mixture of the cells with the beads is effected through activation of the acoustic chips. After about fifteen minutes, the sample, comprising white blood cell-bead complexes, are moved by fluid flow out of the chamber to a separation column. The separation column engages two permanent magnets that capture cells bound to the antibody (white blood cells) on the magnetic beads. Non-captured cells, such as nucleated red blood cells and residual non-nucleated red blood cells, flow through the separation column into a second filtration column.

The sample flows into the second filtration chamber that comprises a single filter. The sample is filtered through the chamber by fluid flow, and further reduced in volume (from about ten milliliters to about one milliliter). After closing of all ports except the reagent port, anti-CD71 antibody coated beads are added to the second filtration chamber. Mixture of the cells with the antibodies is effected through activation of an acoustic chip that engages the chamber.

After an approximately fifteen minute incubation, the sample comprising target cell-magnetic bead complexes are transported by fluid flow to a separation chamber that engages an electromagnetic chip. An electric current is applied to electromagnetic units that are integral to the chip, and beads with attached cells are captured on the chip surface. After ten minutes, fluid flow through the second chamber is resumed, such that cells that are not retained by the electromagnetic force exit the chamber through the outgoing portal. After fifteen minutes, fluid flow is halted, the outgoing portal is closed, and the DC current is turned off. A new collection tube is connected to the tubing of the outgoing portal, the outgoing portal is opened, and fluid flow is resumed in the absence of the electromagnetic field to collect the separated cells in the collection tube.

Example 5

Separation of Nucleated Red Blood Cells from Maternal Blood Using Prepacyte™ in Combination with a Microfabricated Filter The following flow chart shows a three-step procedure for separating nucleated red blood cells from about 40 mL of maternal blood:

(1) Debulk blood;
(2) Deplete white blood cells;
(3) Remove RBCs (filter).

The cell concentrations and cell numbers shown are for illustrative purposes, and do not limit the use of the procedure.

Maternal peripheral blood (40 mls)
$40 \times 5 \times 10^9$ cells/ml = $2 \times 10^{11}$ RBCs
$40 \times 0.5 - 1.0 \times 10^7$ cells/ml = $2 - 4 \times 10^8$ WBCs
$40 \times 1 - 2$ cells/ml = $40 - 80$ nRBCs ↓ Debulk blood (PrepaCyte™)
Add PrepaCyte™
Incubate for 30 min with rotation
Stand and settle for 30 min ~$10^9$ total cells in ~5 mls    Recover supernatant
                                  Wash 2x PBE
$6 - 8 \times 10^8$ RBCs
$2 - 4 \times 10^8$ WBCs         WBC depletion step
$32 - 64$ nRBCs                   Incubate with 10 µgs/ml biotinylated-CD50 Ab for 15 min
                                  Wash 2x with PBE
                                  Incubate with 1.6 micron magnetic streptavidin beads for 15 min
↓                                 Capture of WBC in separation column -continued ~$8 \times 10^8$ total cells in 10 mls (includes wash)
$6 - 8 \times 10^8$ RBCs
$10^4$ WBCs
$26 - 51$ nRBCs ↓ Remove RBCs (Filter)
flow rate of 20 mls/hr in filtration chamber ~$10^6$ total cells in 0.1 ml
$10^6$ RBCs
$10^4$ WBCs
$24 - 46$ nRBCs Example 6

Separation of Nucleated Red Blood Cells from Maternal Blood Using Prepacyte™ in Combination with CD71 Enrichment Step The following flow chart shows a three-step procedure for separating nucleated red blood cells from about 40 mL of maternal blood:

(1) Debulk blood;
(2) Deplete white blood cells;
(3) Capture nRBCs (CD71 Ab).

The cell concentrations and cell numbers shown are for illustrative purposes, and do not limit the use of the procedure.

Maternal peripheral blood (40 mls)
$40 \times 5 \times 10^9$ cells/ml = $2 \times 10^{11}$ RBCs
$40 \times 0.5 - 1.0 \times 10^7$ cells/ml = $2 - 4 \times 10^8$ WBCs
$40 \times 1 - 2$ cells/ml = $40 - 80$ nRBCs ↓ Debulk blood (PrepaCyte™)
Add PrepaCyte™
Incubate for 30 min with rotation
Stand and settle for 30 min ~$10^9$ total cells in ~5 mls    Recover supernatant
                                  Wash 2x with PBE
$6 - 8 \times 10^8$ RBCs
$2 - 4 \times 10^8$ WBCs         WBC depletion step
$32 - 64$ nRBCs                   Incubate with 10 µgs/ml biotinylated-CD50 Ab for 15 min
                                  Wash 2x with PBE
                                  Incubate with 1.6 micron magnetic streptavidin beads for 15 min
↓                                 Capture of WBC in separation column ~$8 \times 10^8$ total cells in 10 mls (includes wash)
$6 - 8 \times 10^8$ RBCs
$10^4$ WBCs                       nRBC capture (CD71)
$26 - 51$ nRBCs                   Incubate with 0.1 ugs/ml biotinylated CD71 Abs for 15 min
                                  Wash 2x with PBE
                                  Incubate with 0.83 micron magnetic streptavinin beads for 15 min
~$10^6$ total cells in 0.1 ml    Capture of nRBC by magnetic field
$10^6$ RBCs
$10^4$ WBCs
$24 - 46$ nRBCs The above procedures in Example 6 and Example 5 can be used in combination, if necessary. For example, a 4-step procedure may be used:

(1) Debulk blood using an RBC sedimenting solution such as PrepaCyte™;
(2) Deplete white blood cells using a specific binding member and magnetic capture;
(3) Remove residual RBCs via filtration;
(4) Capture nRBCs (via CD71 Ab magnetic capture).

The last step in the procedures of Example 5 or Example 6 can also be replaced with a selective lysis step in which red blood cells can be selectively lysed or hypotonically-treated:

(1) Debulk blood using a RBC sedimenting solution such as PrepaCyte™;
(2) Deplete white blood cells using a specific binding member and magnetic capture;
(3) Remove residual RBCs by selective RBC lysis using hypotonic solutions or certain biochemical reagents.

A typical protocol:

1. Take 20 ml peripheral blood of a pregnant subject in a 50 ml conical tube.
2. (Optional) Add fetal liver cells if the efficiency of isolating nRBC is to be examined.
3. Add 12 ml PBE (PBS containing 0.5% BSA and 5 mM EDTA) and 8 ml PrepaCyte, mix gently in a rocker for 30 minutes at room temperature.
4. Stand the tube upright in a rack for 30 minutes to allow the agglutination and sedimentation reaction to occur.
5. Remove the supernatant that contains unprecipitated cells with a pipette, taking care not to disturb the precipitated cells in the red cell layer.
6. Wash cells in PBE twice. The cells are ready for continuing experiments.

Experiments and results

TABLE 2

Effect of tube types and standing time on the WBC and RBC precipitation.

| | | Samples | | | | | | | |
|---|---|---|---|---|---|---|---|---|---|
| | | 1 | 2 | 3 | 4 | 5 | 6 | 7 | 8 |
| Blood volume | MB23480 | 1 ml | 1 ml | 1 ml | 1 ml | 2 ml | 6 ml | 1 ml | 1 ml |
| | Tube | 5 ml culture | | | 10 ml culture | | 15 ml conical | 5 ml culture | |
| Prepacyte | | 1 ml | 1 ml | 1 ml | 1 ml | 2 ml | 6 ml | 0 | 0 |
| PBE | | | | | 0 | | | | 1 ml |
| Rock Time | | | | | 30 min | | | | |
| Stand time | | 15 min | 30 min | 15 min | 30 min | 30 min | 30 min | 30 min | 30 min |
| Tubes used while standing | | 5 ml culture | | | 10 ml culture | | Centrifuge tube | 5 ml culture | |
| Sup Taken | | 1.4 ml | 1.4 ml | 1.4 ml | 1.4 ml | 2.8 ml | 8.4 ml | 0.4 ml | 0 |
| Spin and wash | | | | | Wash with PBE, count cells | | | | |
| Total cells | | 3.6E+07 | 1.8E+07 | 4.0E+07 | 2.0E+07 | 3.2E+07 | 1.4E+08 | 70E+06 | |
| Cells recovered | | | | | | | | | |
| Sup | Slide made | | | | $1 \times 10^5$ cells spun on each slide | | | | |
| | WBC/RBC/% | 60/111/35.1 | 96/101/48.7 | 30/55/35.3 | 62/78/44.3 | 113/160/41.4 | 70/94/42.7 | 157/87/64.3 | |
| | WBC/RBC/% | 41/107/27.7 | 109/90/54.8 | 50/147/25.4 | 69/96/41.8 | 153/120/56.0 | 45/52/46.4 | 143/74/65.9 | |
| | WBC/RBC/% | 48/103/31.8 | 88/47/65.2 | 31/90/25.6 | 55/71/43.7 | 80/77/50.9 | 44/42/51.2 | | |
| | WBC/RBC/% | 35/84/29.4 | 71/83/46.1 | 42/72/36.8 | 70/112/38.5 | 115/112/5.7 | 70/90/43.8 | | |
| | % Cells are WBC | 31.0 | 53.7 | 30.8 | 42.1 | 49.8 | 46.0 | 65.1 | |
| | WBC | 1.1E+07 | 9.7E+06 | 1.2E+07 | 8.4E+06 | 1.6E+07 | 6.4E+07 | 4.6E+06 | |
| | RBC | 2.5E+07 | 8.3E+06 | 2.8E+07 | 1.2E+07 | 1.6E+07 | 7.6E+07 | 2.4E+06 | |
| Pellets | Slide made | | | | 0.3 µl pellet on each slide | | | | |
| | WBC counted | 193 | 268 | 267 | 450 | 309 | 271 | 482 | |
| | Estimated total WBC | 3.9E+05 | 5.4E+05 | 5.3E+05 | 9.0E+05 | 1.2E+06 | 3.3E+06 | 9.6E+05 | |
| % WBC in pellets | | 3.3% | 5.3% | 4.2% | 9.7% | 7.2% | 4.8% | 17.5% | |

Note:
Liquid heights from top to bottom in samples 2, 5 and 6 are same while standing Example 7

Methods for Enriching nRBC with PrepaCyte™

PrepaCyte™ is a one-step cell separation medium made by BioErgonomics (St. Paul, Minn.; http://www.bioe.com) that enables the rapid and efficient removal of erythrocytic, granulocytic, monocytic, and B-lymphocytic components from human peripheral blood. By taking advantage of antibody-stimulated homocytophilic precipitation, PrepaCyte™ facilitates the agglutination and precipitation of erythrocytes, platelets and myeloid components of peripheral blood, resulting in a population of blood cells highly enriched for T-cells, which also includes nRBC.

The experiments showed that Prepacyte induced RBC sedimentation. Tube types apparently did not affect RBC sedimentation, while shorter standing time reduced the number of RBC cell sedimentation.

The following experiments were designed to determine the efficiency of nRBC recovery using various procedures. In each case, a blood sample of an individual in the eighth to the twentieth week of gestation, called "maternal blood sample" was used. In some cases, the maternal blood sample was spiked with fetal liver (FL) cells dissected from an abortus.

TABLE 3

Effects of PrepaCyte amount and tube types on the efficiency of nRBC recovery.

| | Samples | | | | | | | |
|---|---|---|---|---|---|---|---|---|
| | 1 | 2 | 3 | 4 | 5 | 6 | 7 | 8 |
| Blood MB23480 volume Tube | 5 ml | 5 ml | 5 ml | 5 ml | 5 ml | 5 ml | 5 ml | 5 ml |
| | | | 50 ml conical | | | | 15 ml conical | |
| FL | 0 | | | | $5 \times 10^5$ (50 μl $10^7$/ml FL) | | | |
| Prepacyte | 2 ml | 0.25 ml | 0.5 ml | 1 ml | 2 ml | 5 ml | 2 ml | 2 ml |
| PBE | 3 ml | 4.75 ml | 4.5 ml | 4 ml | 3 ml | 0 | 3 ml | 3 ml |
| Rock Time | | | | 30 min | | | | |
| Stand time | 30 min | 30 min | 30 min | 30 min | 30 min | 30 min | 30 min | 30 min |
| Tubes used while standing | | | 50 ml conical | | | | 15 ml conical | 15 ml conical/2 ml 5% BSA in PBE |
| Sup. Taken | 6 ml | 0 | 4 ml | 5 ml | 6 ml | 6.5 ml | 6.5 ml | 8.5 ml |
| Spin and wash | | | | Wash with PBE, count cells | | | | |
| Total cells | 1.1E+08 | | 1.2E+08 | 1.5E+08 | 1.0E+08 | 4.0E+08 | 1.2E+08 | 3.6E+08 |
| % Cells per slide | | | | | 0.1 | | | Control slides (0.05 μl MB24269 + 1000 FL cells control slides made at ending assay) |
| Slide made | | | | | 2 | | | |
| WBC: RBC | 1:01 | | 1:04 | 1:03 | 1:01 | 1:04 | 1:01 | 1:04 |
| WBC | 5.5E+07 | | 2.4E+07 | 3.8E+07 | 5.0E+07 | 8.0E+07 | 6.0E+07 | 7.2E+07 |
| RBC | 5.5E+07 | | 9.6E+07 | 1.1E+08 | 5.0E+07 | 3.2E+08 | 6.0E+07 | 2.9E+08 |
| NRBC counted | | | 32 | 108 | 146 | 120 | 163 | 150 |
| Average | | | 32 | 108 | 146 | 120 | 163 | 150 | 158/140 Average, 148 |
| % nRBC recover | | | 22% | 73% | 99% | 81% | 110% | 101% |

The experiments demonstrated that a 1:4 ratio of PrepaCyte to blood seems to be best in terms of nRBC recovered and number RBC cells precipitated. Tube types apparently did not affect the efficiency of nRBC cell recovery.

TABLE 4

Comparison of efficiency of nRBC recovery using PrepaCyte or density gradients.

| | | | sample1 | sample2 | sample3 | sample 4 |
|---|---|---|---|---|---|---|
| Gradient or PrepaCyte | | | | | | |
| Start samples | | | 20 ml 23489 | 20 ml 23497 | 20 ml 23489 | 20 ml 23497 |
| PBE | | | 20 ml | | 12 ml PBE | |
| Gradient or PrepaCyte | | | Two histoplaque gradient (7.5 ml 1.107/7.5 ml 1.077), 1500 rmp for 30 min. After discarding the serum and aliquoting the layers above the RBC level | | 8 ml PrepaCyte Rock 30 min at RT Stand 30 min at RT take 28 ml sup | take 28 ml sup |
| Wash | | | Two times with PBE, 1500 rpm for first time, 1200 rpm for second time | | | |
| Total cells after gradient | | | 5.0E+07 | 7.0E+07 | 5.0E+08 | 6.0E+08 |
| Depletion of WBC | | | | | | |
| Step 1: Incubation of cells with antibodies | cells | | 5.0E+07 | 7.0E+07 | 5.0E+08 | 6.0E+08 |
| | volume | | 5.0 ml | 7.0 ml | 20 ml | 20 ml |
| | CD50 | | 5 μg | 7 μg | 20 μg | 20 μg |
| | Time/Tem | | 15 min/RT/wash twice | | | |
| Step 2: add beads | volume | | 5.0 ml | 7.0 ml | 20 ml | 20 ml |
| | 1.6 μM Beads | | 0.5 ml | 0.7 ml | 2.0 ml | 2.0 ml |
| | Time/Tem | | 15 min/RT/wash twice | | | |
| Total cells remaining | | | 1.0E+07 | 1.8E+07 | 2.2E+08 | 2.6E+08 |
| % loss of total cells | | | 80% | 74% | 56% | 57% |
| % cells per slide/slide made | | | | 1%/1 | | 0.1%/1 |
| number WBC in one slide | | | 232 | 250 | 225 | 36 |
| Estimated WBC remaining | | | 2.3E+04 | 2.5E+04 | 2.3E+05 | 3.6E+04 |
| % of WBC remaining | | | 0.23% | 0.14% | 0.10% | 0.01% |
| number nRBC in on slide | | | | 12 | | 1 |
| Estimated nRBC in 10 ml MB at least | | | | 600 | | 500 |
| CD71 enrichment of nRBC | | | | | | |
| Step 1 Incubation of cells with antibodies | Cells | | 1.0E+07 | 1.8E+07 | 2.2E+08 | 2.6E+08 |
| | volume | | | 1 ml | | |
| | CD71 | | | 0.1 μg | | |
| | Time/Tem | | | 15 min/RT/wash twice | | |

TABLE 4-continued

Comparison of efficiency of nRBC recovery using PrepaCyte or density gradients.

|  |  | sample1 | sample2 | sample3 | sample 4 |
|---|---|---|---|---|---|
| Step 2: add beads | volume |  | 1 ml |  |  |
|  | bangs beads |  | 5.00E+08 |  |  |
|  | Time/Tem |  | 15 min/RT/wash twice |  |  |
| Total Cells Remaining |  | 1.0E+06 | 3.6E+06 | 1.5E+06 | 6.0E+06 |
| % loss from cell total |  | 90% | 80% | 99% | 98% |
| Approximate WBC:RBC |  | 1:50 | 1/200 | 1:02 | 1/200 |
| Estimated WBC remaining |  | 2.0E+04 | 1.8E+04 | 5.0E+05 | 3.0E+04 |
| Estimated % of WBC |  | 0.039% | 0.026% | 0.100% | 0.005% |
| slides proposed to make |  |  | 20 |  |  |
| Actual sides made |  |  | 6 |  |  |
| nRBC counted |  | 1, 1, 2 | 62, 46, 50 | 2, 3, 4 | 120, 85, 96 |
| counted nRBC in 10 ml MB |  | 13 | 527 | 30 | 1003 |

Table 4 indicates that, when compared with density gradients, the PrepaCyte procedure doubled the nRBC recovery.

A comparison of additional enrichment procedures performed after PrepaCyte RBC sedimentation was also performed. In this case, after sedimenting RBCs with PrepaCyte, the supernatant was depleted of WBCs using a biotinylated CD50 antibody and neutravidin or streptavidin coated magnetic beads. The beads were captured using a Dynal MPC-1 magnetic separator. Following WBC depletion, two different methods were used for further enrichment of nRBCs.

Sample 1 was incubated with biotinylated CD71 antibody, washed twice with PBE, and then streptavidin coated MACS microbeads were added to the sample. The sample was loaded onto a magnetic separation column in a MACS magnet. The cells bound to microbeads were captured and recovered from the column using the manufacturer's recommended protocol. The solution containing the recovered cells in 1 milliliter PBE was centrifuged and the cells sere were resuspended in PBE at a concentration of 1 million cells per milliliter.

Sample 2 was subjected to microfiltration in a polycarbonate chamber comprising a 1 cm×1 cm microfabricated filter with approximately 26% filtration area and having a soft material such as silicon tape between the filter and each subchamber. The filter had approximately 80,000 slots, each 2.8 microns×100 microns, varying in the width dimension by 10% or less, and in the width direction by 10% or less. The top half of the chamber had a cone-shaped opening near the filter about 1 cm in diameter to a conduit connection end of about 0.5 mm and the bottom half of the chamber had a cone-shaped opening near the filter of about 1.5 cm to a conduit connection end of about 0.5 mm. The bottom half also had a second conduit on the side of the chamber.

Fluid flow through the chamber was achieved using a syringe pump, operating at a flow rate of 20 mls per hour. After filtering the sample through the chamber, the top subchamber was rinsed with about 2–3 mls of PBE and then the conduit to the top subchamber was closed off. The bottom subchamber was then rinsed with about 3–5 mls of PBE and then the conduit to the bottom subchamber was closed off. After the filtration procedure, the top subchamber conduit was opened and the cells retained in the chamber were recovered using about 2 mls of PBE.

The results, shown in Table 5, demonstrated that the efficiency of nRBC recovery by microfiltration was comparable to that of using an antibody to CD71 positive selection.

TABLE 5 nRBC recovery using CD71 antibody magnetic capture and microfiltration.

|  |  | sample 1 | sample 2 |
|---|---|---|---|
| Prepacyte |  |  |  |
| Start samples |  | 20 ml 23521 | 20 ml 23517 |
| PBE |  | 12 ml |  |
| prepacyte |  | 8 ml |  |
| Rock |  | 30 min at RT in one 50 ml Conical tube |  |
| Stand |  | 30 min at RT in one 50 ml Conical tubes |  |
| Sup. Taken |  | 28 ml | 28 ml |
| Wash |  | 2x with PBE, 1500 rpm for first time, 1200 rpm for second time |  |
| Total cells after gradient |  | 5.5E+08 | 5.5E+08 |
| % cells per slide/slide made |  | 0.05%/1 |  |
| WBC/RBC |  | 1:01 | 1:01 |
| Depletion of WBC |  |  |  |
| Step 1: Incubation of cells with antibodies | cells | 5.5E+08 | 5.5E+08 |
|  | volume | 20 ml | 20 ml |
|  | CD50 | 20 μg | 20 μg |
|  | Time/Tem |  |  |
| Step 2: add beads | volume | 20 ml | 20 ml |
|  | 1.6 μM Beads | 2.0 ml | 2.0 ml |
|  | Time/Tem |  |  |

TABLE 5-continued nRBC recovery using CD71 antibody magnetic capture and microfiltration.

|  |  | sample 1 | sample 2 |
|---|---|---|---|
| Total cells remaining |  | 2.6E+08 | 2.6E+08 |
| % loss of total cells |  | 53% | 53% |
| % cells per slide/slide made |  |  | 0.1%/1 |
| number WBC in one slide |  | 165 | 420 |
| Estimated WBC remaining |  | 1.7E+05 | 4.2E+05 |
| % of WBC remaining |  | 0.06% | 0.16% |
| CD71 enrichment of nRBC |  |  |  |
| Step 1: Incubation of cells with antibodies | Cells | 2.6E+08 | 2.6E+08 |
|  | volume | 1 ml | cells in 1 ml PBE were |
|  | CD71 | 0.1 µg | subjected to microfiltration |
|  | Time/Tem | 15 min at RT |  |
| Step 2: add beads | volume | 1 ml |  |
|  | bangs beads | 5 × 10$^8$ |  |
|  | Time/Tem | 15 min at RT |  |
| % loss from cell total |  | 100% | 97.6% |
| Approximate WBC:RBC |  | 1:08 | 1:20, 1:30 |
| Estimated WBC remaining |  | 1.6E+05 | 5.2E+05 |
| WBC counted |  |  | 8000 per slide |
| Estimated % of WBC |  | 0.028% | 0.095% |
| slides proposed to make |  | 20 | 40 |
| Actual sides made |  | 4 | 4 |
| nRBC counted |  | 5, 2, 5, 3 | 1, 2, 1, 1 |
| counted nRBC in 10 ml Maternal Blood |  | 38 | 25 |

Example 8

Summary of Lectins Used for Aggregating Red Blood Cells

The following table summarizes the use of various lectin solutions for aggregating RBCs. The buffers contained, as indicated in the third column of Table 6, PBS; PBE (PBS containing 0.5% BSA and 5 mM EDTA); MEM (minimum essential media), alpha-MEM, or LISS, and, where indicated, PrepaCyte™ (Bioergonomics, St. Paul, Minn.); 6% final concentration of bovine serum albumin (BSA); 2% final concentration of polyethylene glycol, 8000 molecular weight (PEG); 10% fetal calf serum (FCS); 10 mM calcium, 10 mM magnesium, 0.032–0.128 M final concentration of potassium oxalate (Oxalate); or 15 U/ml of heparin (heparin). Lectins were added at the specific amounts indicated to the base media to make the test solutions.

In order to evaluate whether the aggregation solution affected nRBCs, fetal liver cells comprising nRBCs and other fetal cells were spiked into the blood sample. nRBC recovery rate was thus calculated from the spiked nRBC and the recovered nRBCs. For red blood cell sedimentation, an equal volume of test solution was mixed with peripheral blood for 30 minutes with rotation. The mixture was then incubated/settled for 30 minutes and the supernatant containing the unprecipitated cells recovered. The supernatant cells were washed and counted. Some samples were further analyzed by putting cells on a slide and determining the nRBC recovery using a Benzidine-Wright-Giemsa histological stain.

TABLE 6

Recovery of nRBCs after sedimenting RBCs with lectin solutions.

| Lectins | Lectin added (ug/ml) | Buffers | Blood | Total cell remaining/ml | % nRBC recovery |
|---|---|---|---|---|---|
| PHA-L | 1–100 | PBE + Prepacyte | Whole blood | 1.2–2.3E+7 |  |
| PHA-E | 1–100 | PBE + Prepacyte | Whole blood | 0.75–1.3E+7 |  |
| PHA-L | 10–100 | PBE + Prepacyte | Whole blood | 1.6–1.8E+7 | 30–94 |
| PHA-E | 1–10 | PBE + Prepacyte | Whole blood | 1.0E+7 | 71–111 |
| PHA-E | 10 | PBE | Whole blood | 3.2E+7 | 71 |
| PNA | 1–10 | PBE + Prepacyte | Whole blood | 1.1–1.6E+7 | 120–128 |
| PNA | 10 | PBE | Whole blood | 1.3E+7 | 15 |
| PHA-E | 10 | PBS + BSA | Whole blood | Settle well |  |
| PHA-E | 10 | PBS + PEG | Whole blood | Some settle |  |
| PHA-E | 10–50 | PBS | Whole blood | Settle well |  |
| PHA-E | 10 | MEM | Whole blood | Some settle |  |
| PHA-E | 10 | MEM+FCS | Whole blood | Settle well |  |
| PHA-E | 10 | Alpha-MEM | Whole blood | Some settle |  |
| ConA | 10–100 | PBS | Whole blood | No settle |  |
| SBA | 10–100 | PBS | Whole blood | Some settle |  |
| LCA | 10–100 | PBS | Whole blood | Little settle |  |
| RCAI | 20–200 | PBS | Whole blood | Settle well |  |
| PSA | 10–100 | PBS | Whole blood | No settle |  |
| SWGA | 10–100 | PBS | Whole blood | No settle |  |

TABLE 6-continued

Recovery of nRBCs after sedimenting RBCs with lectin solutions.

| Lectins | Lectin added (ug/ml) | Buffers | Blood | Total cell remaining/ml | % nRBC recovery |
|---|---|---|---|---|---|
| PHA-E/PNA | 50/50 | PBS | Whole blood | Some settle | |
| RCAI/PHA-E | 20/10 | PBS | Whole blood | Settle well | |
| SBA | 100 | PBS | Whole blood | Little settle | |
| URAI | 100 | PBS | Whole blood | Settle well | |
| WEA | 100 | PBS | Whole blood | Little settle | |
| EBL | 100 | PBS | Whole blood | Little settle | |
| MALII | 100 | PBS | Whole blood | Settle well | |
| GSLI | 100 | PBS | Whole blood | Little settle | |
| SJA | 100 | PBS | Whole blood | Little settle | |
| DBA | 100 | PBS | Whole blood | Little settle | |
| RCAI | 100 | PBS | Whole blood | 9.0E+6 | 163 |
| PHA-E/SBA | 50/50 | PBS | Whole blood | 5.0E+6 | 113 |
| MALII/SBA | 50/50 | PBS | Whole blood | 4.4E+7 | 225 |
| PHA-E/MALII | 50/50 | PBS | Whole blood | 5.0E+6 | 150 |
| Jacalin | 100 | PBS | Whole blood | Little settle | |
| RCAI | 60 | PBE | Whole blood | 2.2E+7 | 108 |
| SBA | 100 | PBE | Whole blood | 5.0E+7 | 63 |
| SBA | 100 | PBS | Whole blood | 8.0E+7 | 27 |
| SBA | 100 | PBE + Ca2+ | Whole blood | 1.6E+8 | 33 |
| SBA | 100 | PBE + Mg2+ | Whole blood | 5.0E+7 | 33 |
| PNA | 100 | PBE | Whole blood | 3.2E+8 | 133 |
| PHA-E | 100 | PBE | Whole blood | 8.1E+6 | 67 |
| PHA | 5 | PBE + Prepacyte | Whole blood | 1.0E+7 | 73 |
| PHA-E | 5 | PBE + Prepacyte | Whole blood | 6.0E+6 | 18 |
| RCA | 5 | PBE + Prepacyte | Whole blood | 1.0E+7 | 2 |
| SBA | 5 | PBE + Prepacyte | Whole blood | 1.0E+7 | 98 |
| UEAI | 5 | PBE + Prepacyte | Whole blood | 9.6E+6 | 55 |
| PHA | 100 | PBE | Whole blood | 5.0E+6 | 6 |
| PHA-E | 100 | PBE | Whole blood | 1.1E+6 | 6 |
| RCA | 60–100 | PBE | Whole blood | 0.6–4.0E+7 | 0–59 |
| SBA | 100 | PBE | Whole blood | 1.6E+8 | 29 |
| UEAI | 100 | PBE | Whole blood | 1.0E+7 | 41 |
| PHA | 2 | PBE + Prepacyte | Whole blood | 1.0E+7 | |
| LEL | 2 | PBE + Prepacyte | Whole blood | 3.2E+7 | |
| PHA-E | 1 | PBE + Prepacyte | Whole blood | 1.7E+7 | |
| PNA | 1 | PBE + Prepacyte | Whole blood | 3.3E+7 | |
| RCA | 1 | PBE + Prepacyte | Whole blood | 2.3E+7 | |
| PHA-E | 25 | Koxalate in MEM | Whole blood | 2.0E+7 | 19 |
| MALII | 25 | Koxalate in MEM | Whole blood | 4.0E+7 | 74 |
| RCAI | 10 | Koxalate in MEM | Whole blood | Little settle | |
| SBA | 25 | Koxalate in MEM | Whole blood | Little settle | |
| PNA | 25 | Koxalate in MEM | Whole blood | Little settle | |
| UEAI | 25 | Koxalate in MEM | Whole blood | Little settle | |
| MALII | 25 | Koxalate in MEM | Whole blood | 1.6E+8 | 50 |
| MALII | 25 | Koxalate in MEM + Heparin | Whole blood | 2.0E+8 | 0 |
| SBA | 50 | Koxalate in MEM | Whole blood | Little settle | |
| UEAI | 50 | Koxalate in MEM | Whole blood | 3.2E+8 | 0 |
| MALII | 25 | LISS | Whole blood | 1.6E+8 | 0 |
| MALII | 30–75 | Koxalate in MEM | Whole blood | 3.5–7.0E+7 | 55–127 |
| MALII | 30 | LISS or PBE | Whole blood | No settle | |
| MALII | 30 | Koxalate in MEM | Whole blood | 2.5E+7 | 80 |

TABLE 6-continued

Recovery of nRBCs after sedimenting RBCs with lectin solutions.

| Lectins | Lectin added (ug/ml) | Buffers | Blood | Total cell remaining/ml | % nRBC recovery |
|---|---|---|---|---|---|
| MALII | 30 | Koxalate in MEM | Wash blood | No settle | |
| UEAI | 50 | Koxalate in MEM | Whole blood | 3.0E+7 | 40 |
| RCAI | 25 | Koxalate in MEM | Whole blood | 1.5E+8 | 0 |

Lectin abbreviations:
ConA: Concanavalin A
DBA: Dolichos biforus agglutinin
DSL: Datura Stramonium lectin
EBL: Sambucus Nigra lectin
ECL: Erythrina Cristagalli lectin
GSLI: Griffonia Simplicifolia lectin I
GSLII: Griffonia Simplicifolia lectin II
Jacalin: Artocarpus integrifolia agglutinin
LCA: Lens culinaris agglutinin
LEL: Lycopersicon esculentum lectin
MALII: Maackia amurensis lectin II
PHA: phaseolus vulgaris agglutinin
PHA-L: phaseolus vulgaris agglutinin leucoagglutinin
PHA-E: phaseolus vulgaris agglutinin erythroagglutinin
PNA: peanut agglutinin
PSA: Pisum Sativum Agglutinin
RCAI: Ricinus Communis Agglutinin I
SBA: Soybean Agglutinin
SJA: Sophora Japonica Agglutinin
STL: Solanum Tuberosum lectin
sWGA: Succinylated wheat germ agglutinin
URAI: Ulex europaeous agglutinin I
WGA: wheat germ agglutinin

Example 9

Use of Lectin Solutions for Isolating nRBCs

The following table summarizes the use of various lectin solutions for recovering nucleated RBCs and removing WBCs. Blood samples were first processed with Prepa-Cyte™ to remove RBCs and obtain WBC-enriched cell samples. Biotinylated lectins and streptavidin coated magnetic beads were then incubated with the samples and lectin positive cells were magnetically captured. The lectins were used to capture RBCs, including nucleated RBCs. Abbreviations for lectins are given in Example 8. Fetal liver cells (including fetal nucleated RBCs) were spiked into the sample being processed with lectin solutions and the nRBC recovery rate was determined after determining the number of nRBCs recovered.

TABLE 7

Summary of lectins used for isolating nRBCs.

| Lectins | Lectin added (ug/ml) | Cells | Cells processed | Cell isolated | % nRBC recovery |
|---|---|---|---|---|---|
| ConA | 0.1 | After Prepacyte | 2.7E+7 | 3.2E+6 | 8 |
| WGA | 0.1 | After Prepacyte | 2.7E+7 | 8.6E+6 | 8 |
| DBA | 0.1 | After Prepacyte | 2.7E+7 | 2.4E+5 | 0 |
| GSLII | 0.1 | After Prepacyte | 2.7E+7 | 2.0E+5 | 0 |
| DSL | 0.1 | After Prepacyte | 2.7E+7 | 4.0E+6 | 54 |
| ECL | 0.1 | After Prepacyte | 2.7E+7 | 2.0E+6 | 1 |
| Jacalin | 0.1 | After Prepacyte | 2.7E+7 | 3.0E+6 | 24 |
| LEL | 0.1 | After Prepacyte | 2.7E+7 | 2.0E+7 | 0 |
| STL | 0.1 | After Prepacyte | 2.7E+7 | 4.0E+6 | 1 |
| WEA | 0.1 | After Prepacyte | 2.7E+7 | 3.6E+6 | 3 |
| EBL | 0.1 | After Prepacyte | 2.7E+7 | 3.6E+6 | 9 |
| CD71 | 0.1 | After Prepacyte | 2.7E+7 | 4.0E+6 | 21 |
| DSL | 0.1 | After Prepacyte | 1.0E+8 | 7.7E+7 | 41 |
| Jacalin | 0.1 | After Prepacyte | 1.0E+8 | 2.3E+7 | 37 |

TABLE 7-continued

Summary of lectins used for isolating nRBCs.

| Lectins | Lectin added (ug/ml) | Cells | Cells processed | Cell isolated | % nRBC recovery |
|---|---|---|---|---|---|
| GSLI | 0.1 | After Prepacyte | 1.0E+8 | 7.2E+5 | 0 |
| PSA | 0.1 | After Prepacyte | 1.0E+8 | 2.3E+7 | 16 |
| LCA | 0.1 | After Prepacyte | 1.0E+8 | 4.0E+7 | 17 |
| PHA-E | 0.1 | After Prepacyte | 1.0E+8 | 4.2E+7 | 12 |
| PHA-L | 0.1 | After Prepacyte | 1.0E+8 | 1.6E+6 | 1 |
| SJA | 0.1 | After Prepacyte | 1.0E+8 | 1.5E+5 | 0 |
| sWGA | 0.1 | After Prepacyte | 1.0E+8 | 3.5E+7 | 0 |
| CD71 | 0.1 | After Prepacyte | 1.0E+8 | 1.5E+5 | 17 |

Example 10

Dextran Solutions for Selectively Sedimenting RBCs

Different compositions of dextran solutions were added in equal volume to blood containing a known amount of target cells to test their efficiency in removing red blood cells from the sample by sedimentation and allowing a high percentage of recovery of nucleated red blood cells from the supernatant.

We performed experiments by using saline (PBE) solutions containing dextran and various other components for aggregating RBCs. In order to evaluate the effect of dextran solutions on nRBC recovery, fetal liver (FL) cells containing fetal nucleated RBCs were spiked into washed maternal blood (MB) samples. The goals for these experiments were to aggregate as much as possible the RBCs, while avoiding nRBCs in the RBC aggregates.

TABLE 8

Efficiency of nRBC recovery after using dextran solutions for RBC sedimentation.

| | |
|---|---|
| Experiment | Precipitation of RBC and WBC with prepacyte or 7% Dextran68 K/16.6% sucrose/0.1% BSA 10% Dextran68 K/2% BSA/1 ug glycophorinA or 2.8% Dextran 68 K/0.128 M KOxalate or 7% Dextran68 K/0.128 M KOxalate |
| Samples | MB24365 (8 week), presurgery, drawn and arrived on Jan. 9, 2002 and spiked with FL23574 (20 weeks) |

| | samples | | | | |
|---|---|---|---|---|---|
| | 1 | 2 | 3 | 4 | 5 |
| Procedures and Results | | | | | |
| | Blood was washed one time with PBE in 50 ml tube at 1200 rpm for 10 min, brake off at 900 rpm. Blood was resuspended to original volume using PBE. FL (0.3 mls of $10^{\wedge}6$ cells per ml added to 3 mls of MB) was spiked into blood and 0.5 ml of mix was put into tubes. Standard was 0.3 mls of $10^{\wedge}6$ cells per ml in a tube with $10^{\wedge}7$ RBCs in 10 mls. | | | | |
| blood | 0.5 ml | 0.5 ml | 0.5 ml | 0.5 ml | 0.5 ml |
| tube | | | 5 ml culture | | |
| Media volume added | 0.5 ml | 0.5 ml | 0.5 ml | 0.5 ml | 0.5 ml |
| Media | PrepaCyte (cold) | 7% Dextran68 K + 16.6% Sucrose + 0.1% BSA | 10% Dextran 68 K + 2% BSA + 1 ug GpA (IgM) | 2.8% Dextran 500 K + 0 128 M KOxalate | 7% Dextran 500 K + 0 128 M KOxalate |
| Rock Time | | | 30 min | | |
| Stand time | | | 30 min | | |
| Standing tubes | | | 2 ml microcentrifuge tube | | |
| sup. Taken | 0.6 ml | 0.6 ml | 0.6 ml | 0.6 ml | 0.6 ml |
| total cells | 5.7E+06 | 4.2E+07 | 5.1E+06 | 7.9E+06 | 1.2E+07 |
| slide made | | | 2 each | | |
| WBC.RBC | 2:1 | 1:20 | 5:1 | 1:5 | 1:10 |
| WBC | 3.8E+06 | 2.0E+06 | 4.2E+06 | 1.3E+06 | 1.0E+06 |
| RBC | 1.9E+06 | 4.0E+07 | 9.0E+05 | 6.6E+06 | 1.0E+07 |
| nRBC avg (counts) | 78 (72, 84) | Hard to count due to blood clumps - but looks to have similar nRBCs compared to GpA or 2.8 Oxalate | 133.5 (128, 139) | 43.5 (39, 48) | 8 (9, 7) |
| corrected nRBC/sample | 4332 | | 6809 | 3437 | 900 |
| % recovery | 62.10% | | 97.60% | 49.30% | 12.90% |
| nRBC spike/sample | 6975 | | nRBCs avg (counts) | 418.5 | (375, 462) |

TABLE 9a

Efficiency of nRBC recovery after using RBC sedimenting solutions.

| Sample 1 2.8% Dex500/ 2% BSA/ 2 ug GpA | Sample 2 2.8% Dex500/ 2% BSA/ 10 ug PHA-E | Sample 3 2.8% Dex500/ 2% BSA/ 50 ug RCA | Sample 4 2.8% Dex500/ 16.3% Sucrose/ 2 ug GpA |
|---|---|---|---|
| Amount of each blood sample | | | |
| 1 ml | 1 ml | 1 ml | 1 ml |
| Amount of spiking (FL) cell suspension added to each sample | | | |
| 100 ul | 100 ul | 100 ul | 100 ul |
| Amount of sedimenting solution added to each sample | | | |
| 1 ml | 1 ml | 1 ml | 1 ml |
| Incubate sample on a lab quake for 30 minutes at room temperature | | | |
| Stand tube upright and after standing thirty minutes collect supernatant | | | |
| RECOVERY AFTER PRECIPITATION STEPS | | | |
| 6.30E+06 total cells recovered | 1.70E+06 total cells recovered | 1.50E+06 total cells recovered | 8.10E+06 total cells recovered |
| Number and percentage nRBCs RECOVERED | | | |
| 13 cells 62.03% nRBCs recovered | 2 cells 1.48% nRBCs recovered | 2 cells 1.48% nRBCs recovered | 16 cells 63.75% nRBCs recovered |
| Spiked control slide counts Slide 1 2033 | | | |

TABLE 9b

Efficiency of nRBC recovery after using RBC sedimenting solutions.

| Sample 5<br>10% Dex68/<br>2% BSA/<br>10 ug PHA-E | Sample 6<br>10% Dex68/<br>2% BSA/<br>50 ug RCA | Sample 7<br>PrepaCyte | Sample 8<br>PrepaCyte |
|---|---|---|---|
| Amount of each blood sample | | | |
| 1 ml | 1 ml | 1 ml | 1 ml |
| Amount of spiking (FL) cell suspension added to each sample | | | |
| 100 ul | 100 ul | 100 ul | none |
| Amount of sedimenting solution added to each sample | | | |
| 1 ml | 1 ml | 1 ml | 1 ml |
| Incubate sample on a lab quake for 30 minutes at room temperature | | | |
| Stand tube upright and after standing thirty minutes collect supernatant | | | |
| RECOVERY AFTER PRECIPITATION STEPS | | | |
| 9.70E+05<br>total cells<br>recovered | 2.10E+06<br>total cells<br>recovered | 1.00E+07<br>total cells<br>recovered | 1.00E+07<br>total cells<br>recovered |
| Number and percentage nRBCs RECOVERED | | | |
| 23 cells<br>15.84%<br>nRBCs recovered | 0 cells<br>0.00%<br>nRBCs recovered | 10 cells<br>49.19%<br>nRBCs recovered | 0 cells |

Example 11
Enrichment of nRBCs Using a Sedimenting Solution, Removal of WBCs, and Selection of nRBCs We performed experiments using a sedimenting solution with the following composition: PBS lacking magnesium and calcium, 5 millimolar EDTA, 2% dextran (MW from 10 to 114 kilodaltons), and 0.05 micrograms per milliliter of IgM antibodies to glycophorin A. In order to evaluate the effect of this dextran solution of nRBC recovery, fetal liver (FL) cells containing fetal nucleated RBC's were spiked into the washed blood samples. In addition, magnetic beads coated with CD50 antibody were added to the sample and incubated with the sample along with the sedimenting solution. The sample tubes were allowed to stand at room temperature alongside a magnet (Immunicon) as RBCs settled. The supernatant was removed and dispensed into a new tube that was again placed next to a magnet. The final supernatant was removed and cells counts of aliquots were performed.

After washing the cells of the supernatant, CD71 antibodies were added and incubated with the remaining cells. Streptavidin-coated magnetic beads from Miltenyi Biotec (MACs system) were added and captured with a magnet. The captured cells were counted.

The results, presented in Table 10 (below) indicate that this procedure can remove 99% of RBCs with a recovery rate of nRBCs of over 80%.

TABLE 10

Efficiency of nRBC recovery after using an RBC Sedimenting Solution.

| | Procedure & Results | | |
|---|---|---|---|
| Sedimenting Time | Sample 1 - 15 min | Sample 2 - 30 min | Sample 3 - 60 min |
| Experiment | Determine effect of time of 1st step incubation on WBC & nRBC recovery from MB | | |
| Samples | MBUCSD21 (8 weeks), presurgery, drawn and arrived on May 9, 2002, 0.5 × $1.0^7$ WBCs per ml | | |
| Sedimenting Time | | | |
| Start samples | 2 ml/tube, MBUCSD21, FL23842 spiked in 100 uls | | |
| Precoat beads | 4/25/02 neutravidin magnetic beads, 5 × $10^9$ beads/ml, use 30 beads/WBC, 30 ugs CD50/$10^9$ beads. Wash beads 3× with PBE, incubated w/ CD50 for 45 min w/ rotation, and wash 4× with PBE | | |
| Wash step | Wash 2× with PBE | | |
| | Incubate with sedimenting solution & precoated beads | | |
| Combined solution/bead incubation | 15 min | 30 min | 60 min |
| Stand | Twice 10 min at RT in 4 ml Immunicon magnet | | |
| mls supernatant recovered | 2.7 mls | | |
| Total cells/ml | 1.16E+07 | 1.11E+07 | 1.19E+07 |
| Total cells | 4.64E+07 | 4.44E+07 | 4.76E+07 |
| WBC enrichment | | | |
| Wash step | One wash with PBE | | |
| Step1: Incubation w/antibodies | | | |
| volume | 1 ml | | |
| CD71 | 0.1 μg | | |
| Time/Tem | 15 min at RT | | |
| Wash | twice with PBE for 10 minutes at 1200 rpms | | |
| Step 2: add beads | | | |
| volume | 1 ml | | |
| MACS beads | 0.1 ml | | |
| Time/Tem | 15 min at RT | | |

TABLE 10-continued

Efficiency of nRBC recovery after using an RBC Sedimenting Solution.

| | | | |
|---|---|---|---|
| Total Cells Remaining | 1.10E+05 | 1.30E+05 | 9.00E+04 |
| Approximate WBC.RBC | 1.05 | 1:10 | |
| nRBC counted per slide | 79 | 64 | 73 |
| Total nRBCs per sample | 79 | 64 | 73 |
| % nRBC recovered | 79.2% | 64.2% | 73.2% |

Number of nRBC on control slides

| Slide 1 | Slide 2 | Slide 3 | Average |
|---|---|---|---|

Example 12

A New Procedure for Enriching Fetal Nucleated RBCs from Maternal Blood

We developed a two-step procedure for enrichment of fetal nucleated RBCs from maternal blood.

Step One: Blood Debulking and WBC Removal.

(1) A combined reagent:

The combined reagent has two components:

a) RBC aggregation solution

2% Dextran (110,000 MW)

0.05 ugs/ml of IgM antibody to glycophorin A 5 mM EDTA

1×PBS without calcium and magnesium.

The RBC aggregation solution also works with a base solution of 1×Hanks balanced saline solution with 15 units/ml heparin instead of 1×PBS and EDTA.

b) WBC depletion solution

Magnetic beads (1.6 micron size from Bangs Laboratories, or 1.0 micron magnetic beads prepared by ourselves), precoated with antibody (20–60 ugs per $10^9$ beads)

The combined reagent has the RBC aggregation solution with 30–60 precoated magnetic beads per WBC.

(2) Use of the combined reagent:

The combined reagent was added to an equal volume of washed peripheral blood and incubated with rotation for 0.5–1 hour. The tube was settled for 0.5 hr upright against a magnet (Dynal, MPC-1). We have also tested a magnet on the bottom of the tube as well.

The solution from the top portion of the tube that did not include aggregated cells (on the side of the tube or at the bottom portion of the tube) was aspirated off and transferred to a new tube.

Step Two: Further Enrichment of nRBC and Removal of RBCs.

The aspirated solution can be then further processed to enrich for nucleated RBCs and remove RBCs by either a magnetic separation step (antibody to CD71 with MACS microbeads) or a microfiltration step. Table 10 (above) shows the results of using a sedimenting solution followed by CD71 antibody capture of nRBCs. Table 11 (below) shows the results of using a combined solution for sedimenting RBCs followed by microfiltraton.

TABLE 11

Testing Sedimenting Solution with Antibody Coated Beads.

| Samples<br>Procedure and Results | MB2086, 20 wk gestation presurgery, drawn and arrived on Aug. 29, 2002, FL 2073 | |
|---|---|---|
| | Sample 1 | Sample 2 |
| Sedimenting Solution | | |
| Number of times washed | 3 | 3 |
| Start samples in mls | 5 | 5 |
| PBS-EDTA | 4 | 4 |
| 10% Dextran in PBS-EDTA | 1 | 1 |
| IgM GpA | 0.25 µg | 0.25 µg |
| Lot of IgM Gpa | 905002 | 905002 |
| Date Received | Aug. 6, 2002 | Aug. 6, 2002 |
| Bead Manufacturer | Aviva | |
| WBCs per ml | 1.20E+07 | 1.20E+07 |
| Beads/WBC | 60 | 60 |
| Bead Lot | Aug. 9, 2002 NAV beads with 20 µg Ab/1 × $10^9$ beads | Aug. 9, 2002 NAV beads with 45 µg Ab/1 × $10^9$ beads |
| Rock | 30 min at RT in one 50 ml Conical tube | |
| Stand | 30 min at RT in one 50 ml Conical tubes | |
| Magnet | Dynal | |
| Microfiltration | | |
| Lot of Filter | Chip 3_1, parallel slots, 2.8 × 100 micron slots, ~40,000 slots | |
| Flow rate | 20 ml/hr | |
| Number of Cells remaining | 6.40E+05 | 9.00E+05 |

TABLE 11-continued

Testing Sedimenting Solution with Antibody Coated Beads.

| | | |
|---|---|---|
| Number of slide proposed to make | 6 | 9 |
| Number slides made | 6 | 9 |
| Number of WBC counted | 6.69E+03 | 7.99E+03 |
| Log Depletion of WBCs | 4.3 | 4.2 |
| Number of nRBCs recovered | 31, 20, 27, 25, 22, 21 | 10, 22, 18, 12, 14, 17, 13, 23, 18 |
| Total number of nRBCs | 146 | 147 |
| Percent of nRBCs recovered | 62% | 62% |

Number of nRBC on control slides

| Slide 1 | Slide 2 | Slide 3 |
|---|---|---|
| 208 | 243 | 255 |
| Average | 235 | |

Example 13

Process Flow Chart for Enriching Fetal Nucleated RBCs from Maternal Blood

Figure 13:
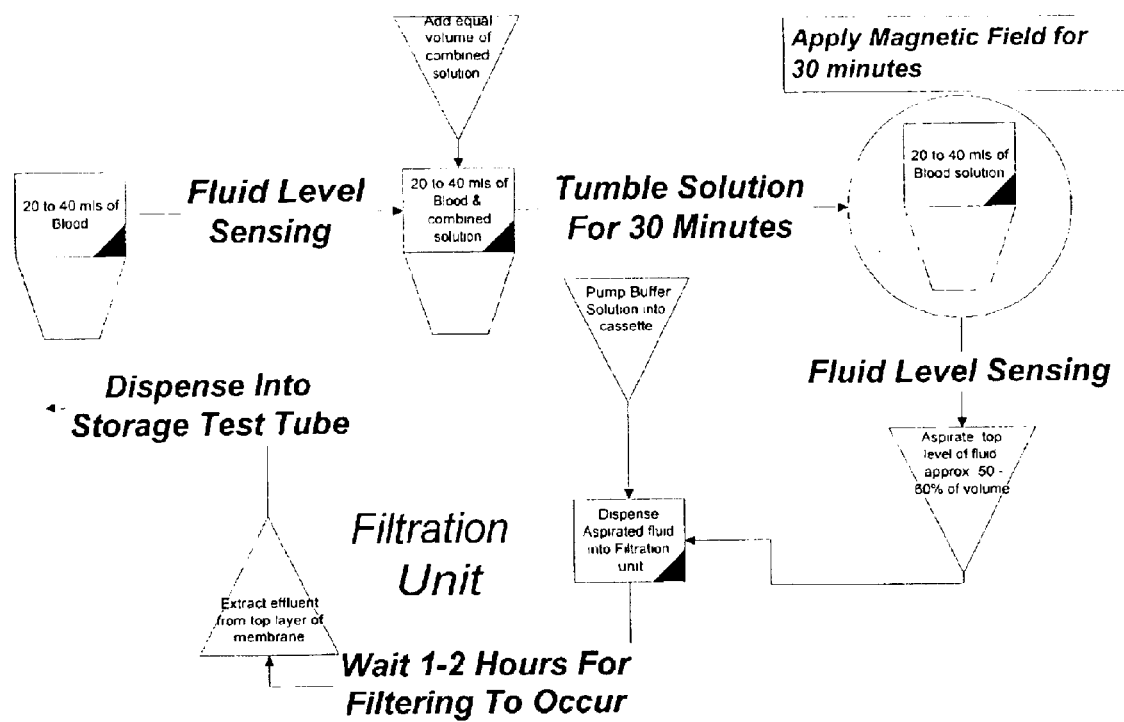
FIG. 13 shows a process flow chart for enriching fetal nucleated RBCs from maternal blood.

FIG. 13 shows a process flow chart for enriching fetal nucleated RBCs from maternal blood samples. The whole process comprises the flowing steps:

(1) The process starts with a volume of blood sample (20–40 ml) in a tube.
(1) Fluidic level sensing step is used to determine the exact volume of the blood sample in the tube to be processed.
(2) Add a volume of the combined reagent (for example, an equal volume of the reagent described in Example 10) to the blood sample in the tube.
(3) Rotate/shake/tumble the solution for a period of time (0.5–1 h).
(4) Let the solutions in the tube settle upright for 30 minutes so that the aggregated RBCs can settle to the bottom of the tube. Simultaneously during this 30 min period, magnetic field is applied to collect and attract WBC-magnetic bead aggregates to a side of tube.
(5) Another fluidic level sensing step is applied to determine what the volume of the "un-aggregated" cell suspension there is in the tube.
(6) Aspirate appropriate volume of the fluid from the tube into the fetal cell filtration chamber (or fetal cell cassette process).
(7) Filter the sample for 1–2 hr in the fetal cell filtration chamber/cassette (Further details of the filtration process are included in Example 14, below.)
(8) Extract solution from the top chamber of the filtration cassette and dispense into storage test tube.

Example 14

Process Flow Chart for Silicon Membrane Filtration Process

FIG. 14 provides a schematic diagram showing the microfiltration process. The simplified process steps include the followings:

(1) Close valves B&D, open valves A&C.
(2) Test sample (coming from the first step of the procedure in Example 10) is loaded into the 45 mL loading reservoir.
(3) Operate waste pump for 1 h so that the sample loaded in the storage reservoir is filtered through the microfabricated filter.
(4) Apply 10 mL wash solution to the Loading Reservoir.
(5) Close valve A, open valve B.
(6) Wash the bottom subchamber with 5 mL.
(7) Close valve C and open valve D.
(8) Rotate the Cassette and filtration chamber 90 degrees.
(9) Flush the filter from valve B.
(10) Collect volume from valve D.

Example 15

Cancer Cell Enrichment from Peripheral Blood Using Microfiltration

Whole peripheral blood (1–5 milliliters) was spiked with 100 microliters of Dulbecco's Modified Eagle's Media (DMEM) tissue culture media containing fluorescently-labeled breast cancer cells (MDA-MB-435s). The breast cancer cells were labeled by incubation of the cells with Hoechst 33342 for 15–20 minutes. The tube was filled with DMEM and centrifuged for 1000 rpm for 5 minutes. The labeled cancer cells were resuspended in DMEM.

The blood sample containing cancer cells was run through a microfabricated filter measuring 1 cm by 1 cm and having a filtration area of approximately 0.38 $cm^2$. The filter had approximately 150,000 slots arranged in a parallel configuration as shown in FIG. 2 with the slots having a taper of one to two degrees and dimensions of 4 microns×50 microns, within a 10% variation in each dimension. The thickness of the filter was 60 microns. The filter was positioned in a two piece filtration chamber with the top half being a cone-shaped filtration chamber measuring about 1 cm at the bottom of the antechamber near the filter and about 0.5 mm at the top where sample was dispensed, with a rectangular shape of 1.5 cm×1.5 cm and a width of 1 cm. The bottom subchamber was cone-shaped and measured about 1.5 cm at the top near the filter and about 0.5 mm at the bottom with a rectangular shape of 2 cm×2 cm and a width of 1 cm at the bottom outlet and having conduits leading in and out of the chamber. A syringe pump provided fluid flow of PBE through the chamber at a flow rate of 20 milliliters per hour.

The captured cells were recovered from the top of the chamber. The cells were put on slides and counted. One experimental result is shown in Table 12.

TABLE 12

Filtration of cancer cells from RBC (MB 29234)

| Procedure and Results Filtration | | Test 1 | Test 2 | Cancer control |
|---|---|---|---|---|
| | Start Sample | 5 ml blood, 100 cancer cells | 2 ml blood, 100 cancer cells | 2.0E+05 RBC, 200 cancer cells |
| | Chip | Taiwan #5_3 | Taiwan #5 3 | |
| | Pump rate | 20 ml/hour | 20 ml/hour | |
| | Capture cells | 2.00E+06 | 1.50E+06 | |
| Results | Slides proposed to make | 10 | 10 | 2 |
| | actual slides made | 6 | 6 | 2 |
| | cancer number (each slide) | 8, 7, 2, 5, 4, 7 | 8, 5, 6, 7, 7, 8 | 80, 85 |
| | total cancer number | 55 | 68 | 82.5 |
| | Capture efficiency | 67% | 82% | |

Figure 17A:
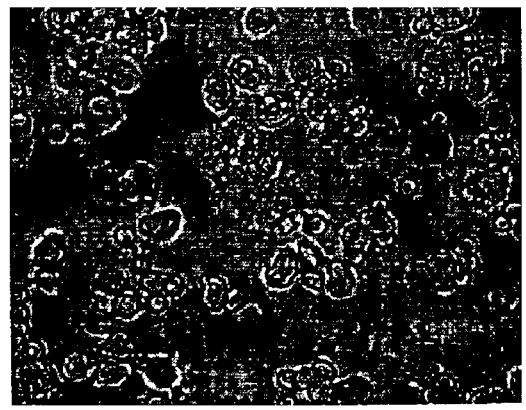
FIG. 17 depicts a fluorescently labeled breast cancer cell in a background of unlabeled blood cells after enrichment by microfiltration. A) phase contrast microscopy of filtered blood sample. B) fluorescence microscopy of the same field shown in A.
Figure 17B:
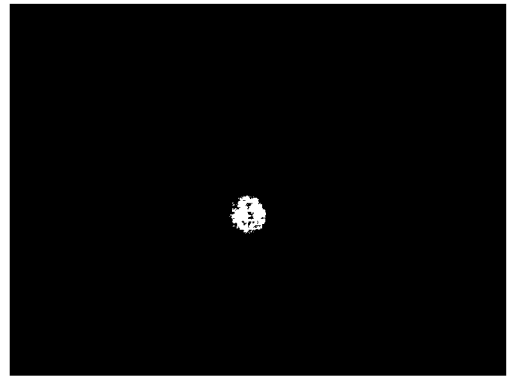
Figure 18A:
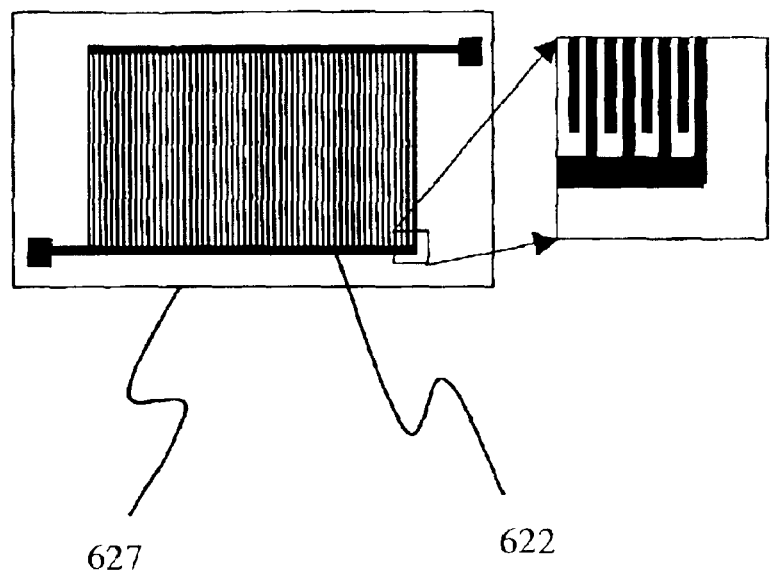
FIG. 18 depicts two configurations of dielectrophoresis chips of the present invention. A) chip with interdigitated electrode geometry; B) chip with castellated electrode geometry.
Figure 18B:
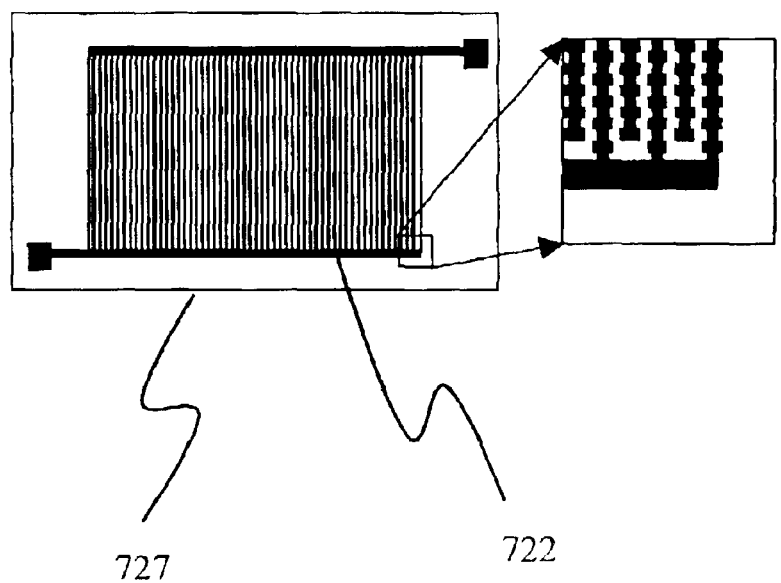
Figures 19A, 19B:
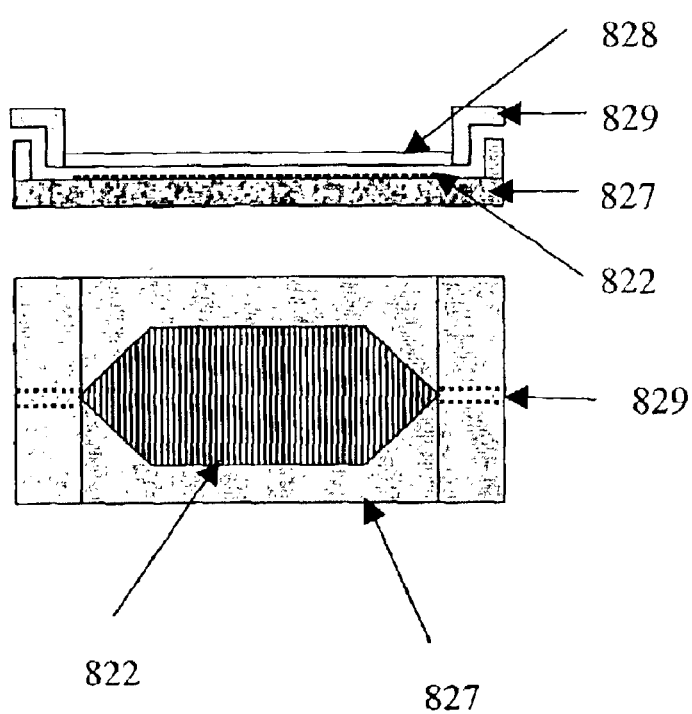
FIG. 19 depicts a separation chamber of the present invention comprising a dielectrophoresis chip. A) Cross-sectional view of the chamber, B) top view showing the chip.

A recovered cancer cell is shown in FIG. 17.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. An automated system for enriching rare cells of a fluid sample, comprising:
   a) at least one filtration chamber of that comprises or engages at least one microfabricated filter comprising one or more tapered pores;
   b) at least one power supply or signal source or control circuit for automated control and powering fluid flow through said at least one filtration chamber;
   c) at least one outlet or at least one vessel for collecting enriched rare cells.

2. The automated system of claim 1, wherein said at least one microfabricated filter comprises at least two tapered pores, wherein the variation in the size of said at least two tapered pores is less than about 20%.

3. The automated system of claim 2, wherein said at least one microfabricated filter comprises a polymer, glass, a ceramic, metal, silicon, or silicon dioxide.

4. The filtration chamber of claim 3, wherein said filtration chamber comprises glass, silicon, silicon dioxide, metal, a ceramic, at least one plastic, or at least one polymer.

5. The automated system of claim 4, wherein said filtration chamber has a volume of from about 0.01 ml to about 2 liters.

6. The automated system of claim 5, wherein said filtration chamber has a volume of from about 0.2 ml to about 80 ml.

7. The automated system of claim 6, wherein said at least one filtration chamber is one filtration chamber.

8. The automated system of claim 7, wherein said filtration chamber comprises one filter.

9. The automated system of claim 7, wherein said automated system comprises at least one valve that can control the flow of said fluid sample into or out of said filtration chamber.

10. The automated system of claim 9, wherein said at least one valve can be automatically opened and closed.

11. The automated system of claim 10, wherein said at least one valve is at least two valves.

12. The automated system of claim 11, further comprising an electrically powered pump or negative pressure system for producing fluid flow through said at least one filtration chamber.

13. The automated system of claim 12, further comprising automated means for transferring sample into said filtration chamber.

14. The automated system of claim 13, further comprising automated means for adding at least one solution or reagent to said fluid sample.

15. The automated system of claim 14, further comprising at least one positive or negative pressure device for transferring enriched cells into a collection vessel.

16. The automated system of claim 15, further comprising automated means for sensing the volume of a sample or a portion thereof.

17. The automated system of claim 16, further comprising means for securing and rocking fluid sample tubes.

18. The automated system of claim 17, comprising at least one tray for loading one or more sample tubes.

19. The automated system of claim 18, further comprising at least one magnet.

20. The automated system of claim 7, wherein said filtration chamber comprises two filters.

21. The automated system of claim 20, comprising at least one inlet for introducing a fluid sample into said automated system.

22. The automated system of claim 21, comprising conduits that can direct fluid through said automated system.

23. The automated system of claim 22, further comprising an electrically powered pump or negative pressure system for producing fluid flow through said at least one filtration chamber.

24. The automated system of claim 23, further comprising one or more active chips.

25. The automated system of claim 24, wherein at least one of said one or more active chips comprises one or more acoustic elements.

26. The automated system of claim 25, wherein at least one of said one or more active chips is a chip comprising at least two electrodes.

27. The automated system of claim 26, further comprising at least one separation chamber.

28. The automated system of claim 27, wherein at least one of said at least one separation chamber comprises a chip that comprises one or more electromagnetic units.

29. The automated system of claim 28, comprising at least one cartridge.

30. The automated system of claim 29, wherein said at least one cartridge is disposable.

31. The automated system of claim 30, wherein at least one of said at least one cartridges comprises at least one separation column.

32. A method of enriching rare cells from a fluid sample, comprising:

a) introducing a fluid sample into the automated system of claim 1;
b) filtering said fluid sample using at least one filtration chamber of the automated system; and
c) removing enriched rare cells from said at least one filtration chamber.

33. The method of claim 32, wherein said fluid sample is a biological sample.

34. The method of claim 33, wherein said sample from a human.

35. The method of claim 34, wherein said sample is a blood sample, an effusion, a urine sample, semen, fecal matter, bone marrow aspirate, spinal fluid, cell suspension from tissue, mucus, sputum, or saliva.

36. The method of claim 35, wherein said rare cells are non-hematopoietic cells or cancer cells.

37. The method of claim 35, wherein said sample is a blood sample.

38. The method of claim 37, wherein said rare cells are fetal cells or a subpopulation of blood cells.

39. The method of claim 38, wherein said at least one microfabricated filter comprises from 4 to 1,000,000 microfabricated slots having a length of from about 20 microns to about 200 microns in length and a width of from between 2.5 and 6 microns in width.

* * * * *